(12) United States Patent
Flores et al.

(10) Patent No.: US 7,375,203 B2
(45) Date of Patent: May 20, 2008

(54) CANINE COLD- AND MENTHOL-SENSITIVE RECEPTOR 1

(75) Inventors: Christopher M. Flores, Lansdale, PA (US); Yi Liu, Jenkintown, PA (US); Mary Lou Lubin, Norristown, PA (US); Ning Qin, Blue Bell, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 68 days.

(21) Appl. No.: 11/099,855

(22) Filed: Apr. 6, 2005

(65) Prior Publication Data

US 2006/0014246 A1  Jan. 19, 2006

Related U.S. Application Data

(60) Provisional application No. 60/621,223, filed on Oct. 22, 2004, provisional application No. 60/560,400, filed on Apr. 8, 2004.

(51) Int. Cl.
  *C07H 21/02*  (2006.01)
  *C07H 21/04*  (2006.01)
(52) U.S. Cl. .................. 536/23.1; 536/23.2; 536/23.4; 536/23.5

(58) Field of Classification Search ..................... None
See application file for complete search history.

(56) References Cited

FOREIGN PATENT DOCUMENTS

| WO | WO 00/40614 A | 7/2000 |
| WO | WO 03/087158 A | 10/2000 |

OTHER PUBLICATIONS

International Search Report dated Dec. 28, 2005 for corresponding Appln. No. PCT/US2005/011391.
Peier Andrea M. et al.: "A TRP Channel That Senses Cold Stimuli and Menthol" Mar. 8, 2002, Cell, Cell Press, Cambridge, NA, US pp. 705-715 XP002246274.
McKemy D.D. et al.: "Identification of a Cold Receptor Reveals a General Role for TRP Channels in Thermosensation" 2002, Nature, Nature Publishing Group, London, GB pp. 52-58, XP002250383.

*Primary Examiner*—Jeffrey Stucker
*Assistant Examiner*—Steve Standley
(74) *Attorney, Agent, or Firm*—Laura Donnelly

(57) ABSTRACT

The present invention provides nucleic acid and polypeptide sequences describing a novel canine cold- and menthol-sensitive receptor, herein named as canine CMR1 (cCMR1). The isolated nucleic acid or polypeptide molecule of the invention can be used in detection assays and screening assays.

6 Claims, 8 Drawing Sheets

SEQUENCE LISTING

```
<160> NUMBER OF SEQ ID NOS: 13

<210> SEQ ID NO 1
<211> LENGTH: 3815
<212> TYPE: DNA
<213> ORGANISM: Canis sp.
<220> FEATURE:
<221> NAME/KEY: CDS
<222> LOCATION: (69)..(3380)

<400> SEQUENCE: 1
acgcggggaa ggccggcagg atctttccag ggaaagcaaa tcctgcctca caaacctcaa         60 ccggagag atg tcc ttc gag ggg gcc agg ctc agc atg agg aac aga agg        110
         Met Ser Phe Glu Gly Ala Arg Leu Ser Met Arg Asn Arg Arg
           1               5                  10 aac ggc acg ctg gac agc acc cgg acc ctg tac tcc agc acg tct cgg        158
Asn Gly Thr Leu Asp Ser Thr Arg Thr Leu Tyr Ser Ser Thr Ser Arg
 15                  20                  25                  30 agc acc gac gtg tcc tac agc gaa agc gac ttg gtg aat ttt att caa        206
Ser Thr Asp Val Ser Tyr Ser Glu Ser Asp Leu Val Asn Phe Ile Gln
                 35                  40                  45 gca aat ttt aag aaa cga gaa tgt gtc ttc ttc acc aaa gat tcc aag        254
Ala Asn Phe Lys Lys Arg Glu Cys Val Phe Phe Thr Lys Asp Ser Lys
             50                  55                  60 gcc acg gaa aat gtg tgc aag tgt ggc tat gcc cag agc cag cac ata        302
Ala Thr Glu Asn Val Cys Lys Cys Gly Tyr Ala Gln Ser Gln His Ile
         65                  70                  75 gaa ggc acc cag atc aac tca aac gag aaa tgg aat tac aag aaa cac        350
Glu Gly Thr Gln Ile Asn Ser Asn Glu Lys Trp Asn Tyr Lys Lys His
     80                  85                  90 acc aag gaa ttt ccg act gac gcc ttt ggg gat att cag ttt gag act        398
Thr Lys Glu Phe Pro Thr Asp Ala Phe Gly Asp Ile Gln Phe Glu Thr
 95                 100                 105                 110
```

|   |   |
|---|---|
| ctg ggg aag aaa ggg aag tat atc cgc ctg tcc tgt gac acg gat gcg<br>Leu Gly Lys Lys Gly Lys Tyr Ile Arg Leu Ser Cys Asp Thr Asp Ala<br>                115                        120                      125 | 446 |
| gag acc ctc tat gag ctg ctg acc cag cac tgg cac ctg aaa acg ccc<br>Glu Thr Leu Tyr Glu Leu Leu Thr Gln His Trp His Leu Lys Thr Pro<br>130                        135                        140 | 494 |
| aac ctg gtc ata tct gtc acc ggc ggc gcc aag aac ttc gcc ctg aag<br>Asn Leu Val Ile Ser Val Thr Gly Gly Ala Lys Asn Phe Ala Leu Lys<br>                145                        150                        155 | 542 |
| ccg agg atg cgc aag atc ttc agc cgc ctc atc tac atc gcg cag tcc<br>Pro Arg Met Arg Lys Ile Phe Ser Arg Leu Ile Tyr Ile Ala Gln Ser<br>160                        165                        170 | 590 |
| aaa ggt gct tgg att ctc act gga gga acc cat tat ggc ctg atg aag<br>Lys Gly Ala Trp Ile Leu Thr Gly Gly Thr His Tyr Gly Leu Met Lys<br>175                        180                        185                        190 | 638 |
| tac atc ggg gag gtg gtg aga gac aac acc atc agc agg aat tca gag<br>Tyr Ile Gly Glu Val Val Arg Asp Asn Thr Ile Ser Arg Asn Ser Glu<br>                      195                        200                        205 | 686 |
| gag aac att gtg gcc att ggc ata gcg gct tgg ggc atg gtc tcc aac<br>Glu Asn Ile Val Ala Ile Gly Ile Ala Ala Trp Gly Met Val Ser Asn<br>                210                        215                        220 | 734 |
| agg gac act ctc ctc agg aat tgc gat gct gag gga tat ttt tca gct<br>Arg Asp Thr Leu Leu Arg Asn Cys Asp Ala Glu Gly Tyr Phe Ser Ala<br>         225                        230                        235 | 782 |
| cag tac ata atg gat gac ttc aag aga gac cct ctg tat atc ttg gac<br>Gln Tyr Ile Met Asp Asp Phe Lys Arg Asp Pro Leu Tyr Ile Leu Asp<br>240                        245                        250 | 830 |
| aac aac cac acc cat ctg ctg ctt gtg gac aac ggc tgc cat gga cat<br>Asn Asn His Thr His Leu Leu Leu Val Asp Asn Gly Cys His Gly His<br>255                        260                        265                        270 | 878 |
| cct aca gtt gaa gca aaa ctc cgg aat cag ctg gag aag tac atc tcc<br>Pro Thr Val Glu Ala Lys Leu Arg Asn Gln Leu Glu Lys Tyr Ile Ser<br>                        275                        280                        285 | 926 |
| gag cgc act att caa gat tcc aac tat ggt ggc aag atc ccc att gtg<br>Glu Arg Thr Ile Gln Asp Ser Asn Tyr Gly Gly Lys Ile Pro Ile Val<br>                290                        295                        300 | 974 |
| tgt ttt gcc caa gga ggt ggc aga gaa act ttg aaa gcc atc aac acc<br>Cys Phe Ala Gln Gly Gly Gly Arg Glu Thr Leu Lys Ala Ile Asn Thr<br>         305                        310                        315 | 1022 |
| tcc atc aaa agc aaa atc ccc tgt gtg gtg gaa ggc tca ggg cag<br>Ser Ile Lys Ser Lys Ile Pro Cys Val Val Glu Gly Ser Gly Gln<br>320                        325                        330 | 1070 |
| att gca gac gtg atc gcg agc ctg gtg gag gtg gag gac gtc ctg acg<br>Ile Ala Asp Val Ile Ala Ser Leu Val Glu Val Glu Asp Val Leu Thr<br>335                        340                        345                        350 | 1118 |
| tca tct gtg gtc aag gag aag ttg gtg cgc ttc tta ccc cgc aca gtg<br>Ser Ser Val Val Lys Glu Lys Leu Val Arg Phe Leu Pro Arg Thr Val<br>                355                        360                        365 | 1166 |
| tcc cgg ctg cct gag gag gag acc gag agt tgg atc aaa tgg ctc aaa<br>Ser Arg Leu Pro Glu Glu Glu Thr Glu Ser Trp Ile Lys Trp Leu Lys<br>                        370                        375                        380 | 1214 |
| gaa att ctc gaa agt tct cac cta tta aca gtt att aaa atg gaa gaa<br>Glu Ile Leu Glu Ser Ser His Leu Leu Thr Val Ile Lys Met Glu Glu<br>         385                        390                        395 | 1262 |
| gct gga gac gaa att gtg agc aat gct att tct tat gct ttg tac aaa<br>Ala Gly Asp Glu Ile Val Ser Asn Ala Ile Ser Tyr Ala Leu Tyr Lys<br>400                        405                        410 | 1310 |
| gcc ttt agc acc aat gaa caa gat aag gat aac tgg aat ggg cag ctg<br>Ala Phe Ser Thr Asn Glu Gln Asp Lys Asp Asn Trp Asn Gly Gln Leu<br>415                        420                        425                        430 | 1358 |

```
aag ctt ctg ctg gaa tgg aac cag ctg gac cta gcc aat gag gag ata    1406
Lys Leu Leu Leu Glu Trp Asn Gln Leu Asp Leu Ala Asn Glu Glu Ile
            435                 440                 445 ttc acc aac gac cgc cga tgg ggg tct gct gat ctg caa gag gtc atg    1454
Phe Thr Asn Asp Arg Arg Trp Gly Ser Ala Asp Leu Gln Glu Val Met
    450                 455                 460 ttt aca gct ctc ata aag gac aga ccc aag ttt gtc cgc ctc ttc ctg    1502
Phe Thr Ala Leu Ile Lys Asp Arg Pro Lys Phe Val Arg Leu Phe Leu
465                 470                 475 gag aat ggg ttg aac ctg cgc aag ttt ctc acc aat gac gtc ctc act    1550
Glu Asn Gly Leu Asn Leu Arg Lys Phe Leu Thr Asn Asp Val Leu Thr
        480                 485                 490 gaa ctc ttc tcc aac cac ttc agc acc ctt gtc tac cgg aac ctg cag    1598
Glu Leu Phe Ser Asn His Phe Ser Thr Leu Val Tyr Arg Asn Leu Gln
495                 500                 505                 510 att gcc aag aat tcc tat aac gat gcc ctc ctc aca ttc gtc tgg aaa    1646
Ile Ala Lys Asn Ser Tyr Asn Asp Ala Leu Leu Thr Phe Val Trp Lys
                515                 520                 525 ctg gtg gcc aac ttc cgg aga ggc ttc cga aag gaa gac aga agt agc    1694
Leu Val Ala Asn Phe Arg Arg Gly Phe Arg Lys Glu Asp Arg Ser Ser
            530                 535                 540 agg gat gac ata gat gta gaa ctt cac gat gtg tct cct atc act cgg    1742
Arg Asp Asp Ile Asp Val Glu Leu His Asp Val Ser Pro Ile Thr Arg
        545                 550                 555 cac ccg ctg caa gca cac ttc atc tgg gcc att ctt cag aac aag aag    1790
His Pro Leu Gln Ala His Phe Ile Trp Ala Ile Leu Gln Asn Lys Lys
    560                 565                 570 gaa ctg tcc aag gtc att tgg gag cag acc agg ggc tgc acg ttg gca    1838
Glu Leu Ser Lys Val Ile Trp Glu Gln Thr Arg Gly Cys Thr Leu Ala
575                 580                 585                 590 gcc ctg gga gcc agc aag ctt ctg aag act ctg gcc aag gtg aag aat    1886
Ala Leu Gly Ala Ser Lys Leu Leu Lys Thr Leu Ala Lys Val Lys Asn
                595                 600                 605 gac atc aat gct gca ggg gag tcc gag gag ctg gca aat gag tat gag    1934
Asp Ile Asn Ala Ala Gly Glu Ser Glu Glu Leu Ala Asn Glu Tyr Glu
            610                 615                 620 acc cgt gca gtt gag ctg ttc acg gag tgc tac agc agc gac gag gac    1982
Thr Arg Ala Val Glu Leu Phe Thr Glu Cys Tyr Ser Ser Asp Glu Asp
        625                 630                 635 ctg gcc gag cag ctg ctg gtg tac tcc tgc gaa gcc tgg ggc ggg agc    2030
Leu Ala Glu Gln Leu Leu Val Tyr Ser Cys Glu Ala Trp Gly Gly Ser
    640                 645                 650 aac tgc ttg gag ctg gcg gtg gag gcc acg gac cag cac ttc atc gcc    2078
Asn Cys Leu Glu Leu Ala Val Glu Ala Thr Asp Gln His Phe Ile Ala
655                 660                 665                 670 cag ccc ggg gtc cag aat ttt ctt tcc aag caa tgg tat gga gag att    2126
Gln Pro Gly Val Gln Asn Phe Leu Ser Lys Gln Trp Tyr Gly Glu Ile
                675                 680                 685 tcc cga gac acc aag aac tgg aag att atc ctg tgt ttg ttt att ata    2174
Ser Arg Asp Thr Lys Asn Trp Lys Ile Ile Leu Cys Leu Phe Ile Ile
            690                 695                 700 ccc ttg gtg ggc tgt ggc ttt gta tcc ttt agg aag agg ccc atc gac    2222
Pro Leu Val Gly Cys Gly Phe Val Ser Phe Arg Lys Arg Pro Ile Asp
        705                 710                 715 aag cac aag aag atc ctg tgg tac tac gtg gcg ttc ttc acc tcc ccc    2270
Lys His Lys Lys Ile Leu Trp Tyr Tyr Val Ala Phe Phe Thr Ser Pro
    720                 725                 730 ttt gtg gtc ttc gcc tgg aac gtg gtc ttc tac atc gcc ttc ctc ctg    2318
Phe Val Val Phe Ala Trp Asn Val Val Phe Tyr Ile Ala Phe Leu Leu
```

-continued

```
                735                 740                 745                 750
ctc ttt gcc tac gtg ctg ctc atg gat ttt cac tca gtg cca cac tcc    2366
Leu Phe Ala Tyr Val Leu Leu Met Asp Phe His Ser Val Pro His Ser
                    755                 760                 765 ccc gag ctg gtc ctc tac gca ctg gtc ttt gtc ctg ttc tgt gat gaa    2414
Pro Glu Leu Val Leu Tyr Ala Leu Val Phe Val Leu Phe Cys Asp Glu
            770                 775                 780 gtg aga cag tgg tac atg aat ggg gtg aat tat ttt acc gac ctg tgg    2462
Val Arg Gln Trp Tyr Met Asn Gly Val Asn Tyr Phe Thr Asp Leu Trp
        785                 790                 795 aat gtc atg gac aca ctt ggg ctt ttt tac ttc ata gca ggc att gtg    2510
Asn Val Met Asp Thr Leu Gly Leu Phe Tyr Phe Ile Ala Gly Ile Val
    800                 805                 810 ttt cgg ctc cac cct tct aat aaa acc tct ttg tat tcc gga cga gtc    2558
Phe Arg Leu His Pro Ser Asn Lys Thr Ser Leu Tyr Ser Gly Arg Val
815                 820                 825                 830 atc ttt tgc ctg gat tac att ata ttc acc cta agg ttg atc cac att    2606
Ile Phe Cys Leu Asp Tyr Ile Ile Phe Thr Leu Arg Leu Ile His Ile
                    835                 840                 845 ttc acc gta agc aga aat ttg gga ccg aag att ata atg ttg cag agg    2654
Phe Thr Val Ser Arg Asn Leu Gly Pro Lys Ile Ile Met Leu Gln Arg
            850                 855                 860 atg ctg atc gac gtg ttc ttc ctg ttt ctg ttt gcc gtg tgg atg        2702
Met Leu Ile Asp Val Phe Phe Phe Leu Phe Leu Phe Ala Val Trp Met
        865                 870                 875 gtg gcc ttc ggc gtg gcc agg caa ggg atc ctc agg caa aat gag cat    2750
Val Ala Phe Gly Val Ala Arg Gln Gly Ile Leu Arg Gln Asn Glu His
    880                 885                 890 cgc tgg agg tgg ata ttc cgc tcg gtt atc tac gag ccc tac ctg gcc    2798
Arg Trp Arg Trp Ile Phe Arg Ser Val Ile Tyr Glu Pro Tyr Leu Ala
895                 900                 905                 910 atg ttc ggc caa gtg ccc agc gac gtg gat ggt acc aca tat gac ttt    2846
Met Phe Gly Gln Val Pro Ser Asp Val Asp Gly Thr Thr Tyr Asp Phe
                    915                 920                 925 gcc cac tgc act ttc act ggg aat gag tcc aag ccg ctg tgt gtg gag    2894
Ala His Cys Thr Phe Thr Gly Asn Glu Ser Lys Pro Leu Cys Val Glu
            930                 935                 940 ctg gat gag cac aac ctc ccc cgg ttc ccc gag tgg atc acc atc cct    2942
Leu Asp Glu His Asn Leu Pro Arg Phe Pro Glu Trp Ile Thr Ile Pro
        945                 950                 955 ctg gtg tgc atc tac atg ctc tcc acc aac atc ctg ctg gtc aat ctg    2990
Leu Val Cys Ile Tyr Met Leu Ser Thr Asn Ile Leu Leu Val Asn Leu
    960                 965                 970 ctc gtt gcc atg ttt ggc tac aca gtg gga acg gtc cag gag aac aac    3038
Leu Val Ala Met Phe Gly Tyr Thr Val Gly Thr Val Gln Glu Asn Asn
975                 980                 985                 990 gat cag gtc tgg aag ttc cag agg tac ttc ttg gtg cag gag tac tgc    3086
Asp Gln Val Trp Lys Phe Gln Arg Tyr Phe Leu Val Gln Glu Tyr Cys
                    995                 1000                1005 aac cgc ctg aac atc ccc ttc ccc ttt gtg gtc ttc gcc tac ttc tac    3134
Asn Arg Leu Asn Ile Pro Phe Pro Phe Val Val Phe Ala Tyr Phe Tyr
            1010                1015                1020 atg gtg gtc aag aag tgc ttc gga tgc tgc tgc agg gag aaa cac gcc    3182
Met Val Val Lys Lys Cys Phe Gly Cys Cys Cys Arg Glu Lys His Ala
        1025                1030                1035 gag cct tct gcc tgc tgt ttc aga aat gaa gac aat gag act ctg gca    3230
Glu Pro Ser Ala Cys Cys Phe Arg Asn Glu Asp Asn Glu Thr Leu Ala
    1040                1045                1050 tgg gag ggt gtc atg aaa gaa aat tac ctt gtc aag atc aac acg gag    3278
```

```
Trp Glu Gly Val Met Lys Glu Asn Tyr Leu Val Lys Ile Asn Thr Glu
1055                1060                1065                1070 gcc aat gac acc tca cag gaa atg agg cat cgg ttt aga cag ctg gat    3326
Ala Asn Asp Thr Ser Gln Glu Met Arg His Arg Phe Arg Gln Leu Asp
            1075                1080                1085 aca aag att aat gat ctc aag ggc ctt ctg aaa gag atc gct aat aaa    3374
Thr Lys Ile Asn Asp Leu Lys Gly Leu Leu Lys Glu Ile Ala Asn Lys
                1090                1095                1100 atc aaa tagaacttca tggactgtac tggagaaaaa cctaattata gcaaggtgac     3430
Ile Lys accagaaatc gaagtgggaa ccagtcaaga aaagctgatg aacagttttg ttactgactg  3490
ctcagtaaga actgttcagg ccgtgggtat ttagcagatg gctttcatca ccccagtgtg  3550
ctcaaatctg ggaaacagac gtgtgattgg tttcccccga agatagac acccaggaag    3610 agcttcccct gaaggccacc ctgttacttc ctgagtctcc accactcata cccactgcgg  3670
gtcatcttag agtgtgttcc tgcactcttc ttctttcttc acttttccta cttctaactc  3730
tgtgcatatt acatctctcc tgcaaggggg tcatgccttc cctcccataa aaagaaaaa   3790 aaaaaaaaaa aaaaaaaaaa aaaaa                                        3815

<210> SEQ ID NO 2
<211> LENGTH: 1104
<212> TYPE: PRT
<213> ORGANISM: Canis sp.

<400> SEQUENCE: 2

Met Ser Phe Glu Gly Ala Arg Leu Ser Met Arg Asn Arg Arg Asn Gly
 1               5                  10                  15

Thr Leu Asp Ser Thr Arg Thr Leu Tyr Ser Ser Thr Ser Arg Ser Thr
            20                  25                  30

Asp Val Ser Tyr Ser Glu Ser Asp Leu Val Asn Phe Ile Gln Ala Asn
        35                  40                  45

Phe Lys Lys Arg Glu Cys Val Phe Phe Thr Lys Asp Ser Lys Ala Thr
    50                  55                  60

Glu Asn Val Cys Lys Cys Gly Tyr Ala Gln Ser Gln His Ile Glu Gly
65                  70                  75                  80

Thr Gln Ile Asn Ser Asn Glu Lys Trp Asn Tyr Lys Lys His Thr Lys
                85                  90                  95

Glu Phe Pro Thr Asp Ala Phe Gly Asp Ile Gln Phe Glu Thr Leu Gly
            100                 105                 110

Lys Lys Gly Lys Tyr Ile Arg Leu Ser Cys Asp Thr Asp Ala Glu Thr
        115                 120                 125

Leu Tyr Glu Leu Leu Thr Gln His Trp His Leu Lys Thr Pro Asn Leu
    130                 135                 140

Val Ile Ser Val Thr Gly Gly Ala Lys Asn Phe Ala Leu Lys Pro Arg
145                 150                 155                 160

Met Arg Lys Ile Phe Ser Arg Leu Ile Tyr Ile Ala Gln Ser Lys Gly
                165                 170                 175

Ala Trp Ile Leu Thr Gly Gly Thr His Tyr Gly Leu Met Lys Tyr Ile
            180                 185                 190

Gly Glu Val Val Arg Asp Asn Thr Ile Ser Arg Asn Ser Glu Glu Asn
        195                 200                 205

Ile Val Ala Ile Gly Ile Ala Ala Trp Gly Met Val Ser Asn Arg Asp
    210                 215                 220

Thr Leu Leu Arg Asn Cys Asp Ala Glu Gly Tyr Phe Ser Ala Gln Tyr
```

```
            225                 230                 235                 240
Ile Met Asp Asp Phe Lys Arg Asp Pro Leu Tyr Ile Leu Asp Asn Asn
                245                 250                 255

His Thr His Leu Leu Val Asp Asn Gly Cys His Gly His Pro Thr
        260                 265                 270

Val Glu Ala Lys Leu Arg Asn Gln Leu Glu Lys Tyr Ile Ser Glu Arg
        275                 280                 285

Thr Ile Gln Asp Ser Asn Tyr Gly Gly Lys Ile Pro Ile Val Cys Phe
        290                 295                 300

Ala Gln Gly Gly Gly Arg Glu Thr Leu Lys Ala Ile Asn Thr Ser Ile
305                 310                 315                 320

Lys Ser Lys Ile Pro Cys Val Val Glu Gly Ser Gly Gln Ile Ala
                325                 330                 335

Asp Val Ile Ala Ser Leu Val Glu Val Glu Asp Val Leu Thr Ser Ser
                340                 345                 350

Val Val Lys Glu Lys Leu Val Arg Phe Leu Pro Arg Thr Val Ser Arg
        355                 360                 365

Leu Pro Glu Glu Glu Thr Glu Ser Trp Ile Lys Trp Leu Lys Glu Ile
370                 375                 380

Leu Glu Ser Ser His Leu Leu Thr Val Ile Lys Met Glu Glu Ala Gly
385                 390                 395                 400

Asp Glu Ile Val Ser Asn Ala Ile Ser Tyr Ala Leu Tyr Lys Ala Phe
                405                 410                 415

Ser Thr Asn Glu Gln Asp Lys Asp Asn Trp Asn Gly Gln Leu Lys Leu
        420                 425                 430

Leu Leu Glu Trp Asn Gln Leu Asp Leu Ala Asn Glu Glu Ile Phe Thr
        435                 440                 445

Asn Asp Arg Arg Trp Gly Ser Ala Asp Leu Gln Glu Val Met Phe Thr
        450                 455                 460

Ala Leu Ile Lys Asp Arg Pro Lys Phe Val Arg Leu Phe Leu Glu Asn
465                 470                 475                 480

Gly Leu Asn Leu Arg Lys Phe Leu Thr Asn Asp Val Leu Thr Glu Leu
                485                 490                 495

Phe Ser Asn His Phe Ser Thr Leu Val Tyr Arg Asn Leu Gln Ile Ala
                500                 505                 510

Lys Asn Ser Tyr Asn Asp Ala Leu Leu Thr Phe Val Trp Lys Leu Val
        515                 520                 525

Ala Asn Phe Arg Arg Gly Phe Arg Lys Glu Asp Arg Ser Ser Arg Asp
        530                 535                 540

Asp Ile Asp Val Glu Leu His Asp Val Ser Pro Ile Thr Arg His Pro
545                 550                 555                 560

Leu Gln Ala His Phe Ile Trp Ala Ile Leu Gln Asn Lys Lys Glu Leu
                565                 570                 575

Ser Lys Val Ile Trp Glu Gln Thr Arg Gly Cys Thr Leu Ala Ala Leu
        580                 585                 590

Gly Ala Ser Lys Leu Leu Lys Thr Leu Ala Lys Val Lys Asn Asp Ile
        595                 600                 605

Asn Ala Ala Gly Glu Ser Glu Glu Leu Ala Asn Glu Tyr Glu Thr Arg
        610                 615                 620

Ala Val Glu Leu Phe Thr Glu Cys Tyr Ser Ser Asp Glu Asp Leu Ala
625                 630                 635                 640

Glu Gln Leu Leu Val Tyr Ser Cys Glu Ala Trp Gly Gly Ser Asn Cys
                645                 650                 655
```

-continued

Leu Glu Leu Ala Val Glu Ala Thr Asp Gln His Phe Ile Ala Gln Pro
            660                 665                 670

Gly Val Gln Asn Phe Leu Ser Lys Gln Trp Tyr Gly Glu Ile Ser Arg
            675                 680                 685

Asp Thr Lys Asn Trp Lys Ile Ile Leu Cys Leu Phe Ile Ile Pro Leu
            690                 695                 700

Val Gly Cys Gly Phe Val Ser Phe Arg Lys Arg Pro Ile Asp Lys His
705                 710                 715                 720

Lys Lys Ile Leu Trp Tyr Tyr Val Ala Phe Phe Thr Ser Pro Phe Val
                725                 730                 735

Val Phe Ala Trp Asn Val Val Phe Tyr Ile Ala Phe Leu Leu Leu Phe
            740                 745                 750

Ala Tyr Val Leu Leu Met Asp Phe His Ser Val Pro His Ser Pro Glu
            755                 760                 765

Leu Val Leu Tyr Ala Leu Val Phe Val Leu Phe Cys Asp Glu Val Arg
            770                 775                 780

Gln Trp Tyr Met Asn Gly Val Asn Tyr Phe Thr Asp Leu Trp Asn Val
785                 790                 795                 800

Met Asp Thr Leu Gly Leu Phe Tyr Phe Ile Ala Gly Ile Val Phe Arg
                805                 810                 815

Leu His Pro Ser Asn Lys Thr Ser Leu Tyr Ser Gly Arg Val Ile Phe
            820                 825                 830

Cys Leu Asp Tyr Ile Ile Phe Thr Leu Arg Leu Ile His Ile Phe Thr
            835                 840                 845

Val Ser Arg Asn Leu Gly Pro Lys Ile Ile Met Leu Gln Arg Met Leu
850                 855                 860

Ile Asp Val Phe Phe Phe Leu Phe Leu Phe Ala Val Trp Met Val Ala
865                 870                 875                 880

Phe Gly Val Ala Arg Gln Gly Ile Leu Arg Gln Asn Glu His Arg Trp
                885                 890                 895

Arg Trp Ile Phe Arg Ser Val Ile Tyr Glu Pro Tyr Leu Ala Met Phe
            900                 905                 910

Gly Gln Val Pro Ser Asp Val Asp Gly Thr Thr Tyr Asp Phe Ala His
            915                 920                 925

Cys Thr Phe Thr Gly Asn Glu Ser Lys Pro Leu Cys Val Glu Leu Asp
            930                 935                 940

Glu His Asn Leu Pro Arg Phe Pro Glu Trp Ile Thr Ile Pro Leu Val
945                 950                 955                 960

Cys Ile Tyr Met Leu Ser Thr Asn Ile Leu Leu Val Asn Leu Leu Val
                965                 970                 975

Ala Met Phe Gly Tyr Thr Val Gly Thr Val Gln Glu Asn Asn Asp Gln
            980                 985                 990

Val Trp Lys Phe Gln Arg Tyr Phe Leu Val Gln Glu Tyr Cys Asn Arg
            995                 1000                1005

Leu Asn Ile Pro Phe Pro Phe Val Val Phe Ala Tyr Phe Tyr Met Val
    1010                1015                1020

Val Lys Lys Cys Phe Gly Cys Cys Cys Arg Glu Lys His Ala Glu Pro
1025                1030                1035                1040

Ser Ala Cys Cys Phe Arg Asn Glu Asp Asn Glu Thr Leu Ala Trp Glu
                1045                1050                1055

Gly Val Met Lys Glu Asn Tyr Leu Val Lys Ile Asn Thr Glu Ala Asn
            1060                1065                1070

Asp Thr Ser Gln Glu Met Arg His Arg Phe Arg Gln Leu Asp Thr Lys
        1075                1080                1085

Ile Asn Asp Leu Lys Gly Leu Leu Lys Glu Ile Ala Asn Lys Ile Lys
        1090                1095                1100

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttcatctggg ccattcttca g                                              21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cacagtggct tggactcatt                                                20

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcccatcgac aagcacaaga agatc                                          25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatcttcttg tgcttgtcga tgggc                                          25

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccatcctaat acgactcact atagggc                                        27

<210> SEQ ID NO 8
<211> LENGTH: 44
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 8
aagcttcata tgtccttcga gggggccagg ctcagcatga ggaa                           44

<210> SEQ ID NO 9
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctcgagctat ttgattttat tagcgatctc tttcagaagg ccc                            43

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (50)
<223> OTHER INFORMATION: g, a or c
<220> FEATURE:
<221> NAME/KEY: modified_base
<222> LOCATION: (51)
<223> OTHER INFORMATION: g, a, c or t

<400> SEQUENCE: 10
ttctagaatt cagcggcgct tttttttttt tttttttttt tttttttttn n                   51

<210> SEQ ID NO 11
<211> LENGTH: 1104
<212> TYPE: PRT
<213> ORGANISM: Homo sapiens

<400> SEQUENCE: 11

Met Ser Phe Arg Ala Ala Arg Leu Ser Met Arg Asn Arg Arg Asn Asp
 1               5                  10                  15

Thr Leu Asp Ser Thr Arg Thr Leu Tyr Ser Ser Ala Ser Arg Ser Thr
            20                  25                  30

Asp Leu Ser Tyr Ser Glu Ser Asp Leu Val Asn Phe Ile Gln Ala Asn
        35                  40                  45

Phe Lys Lys Arg Glu Cys Val Phe Phe Ile Lys Asp Ser Lys Ala Thr
    50                  55                  60

Glu Asn Val Cys Lys Cys Gly Tyr Ala Gln Ser Gln His Met Glu Gly
65                  70                  75                  80

Thr Gln Ile Asn Gln Ser Glu Lys Trp Asn Tyr Lys Lys His Thr Lys
                85                  90                  95

Glu Phe Pro Thr Asp Ala Phe Gly Asp Ile Gln Phe Glu Thr Leu Gly
            100                 105                 110

Lys Lys Gly Lys Tyr Ile Arg Leu Ser Cys Asp Thr Asp Ala Glu Ile
        115                 120                 125

Leu Tyr Glu Leu Leu Thr Gln His Trp His Leu Lys Thr Pro Asn Leu
    130                 135                 140

Val Ile Ser Val Thr Gly Gly Ala Lys Asn Phe Ala Leu Lys Pro Arg
145                 150                 155                 160

Met Arg Lys Ile Phe Ser Arg Leu Ile Tyr Ile Ala Gln Ser Lys Gly
                165                 170                 175

-continued

```
Ala Trp Ile Leu Thr Gly Gly Thr His Tyr Gly Leu Met Lys Tyr Ile
            180                 185                 190
Gly Glu Val Val Arg Asp Asn Thr Ile Ser Arg Ser Glu Glu Asn
        195                 200                 205
Ile Val Ala Ile Gly Ile Ala Ala Trp Gly Met Val Ser Asn Arg Asp
        210                 215                 220
Thr Leu Ile Arg Asn Cys Asp Ala Glu Gly Tyr Phe Leu Ala Gln Tyr
225                 230                 235                 240
Leu Met Asp Asp Phe Thr Arg Asp Pro Leu Tyr Ile Leu Asp Asn Asn
                245                 250                 255
His Thr His Leu Leu Leu Val Asp Asn Gly Cys His Gly His Pro Thr
                260                 265                 270
Val Glu Ala Lys Leu Arg Asn Gln Leu Glu Lys Tyr Ile Ser Glu Arg
            275                 280                 285
Thr Ile Gln Asp Ser Asn Tyr Gly Gly Lys Ile Pro Ile Val Cys Phe
        290                 295                 300
Ala Gln Gly Gly Gly Lys Glu Thr Leu Lys Ala Ile Asn Thr Ser Ile
305                 310                 315                 320
Lys Asn Lys Ile Pro Cys Val Val Glu Gly Ser Gly Gln Ile Ala
                325                 330                 335
Asp Val Ile Ala Ser Leu Val Glu Val Glu Asp Ala Leu Thr Ser Ser
            340                 345                 350
Ala Val Lys Glu Lys Leu Val Arg Phe Leu Pro Arg Thr Val Ser Arg
        355                 360                 365
Leu Pro Glu Glu Glu Thr Glu Ser Trp Ile Lys Trp Leu Lys Glu Ile
    370                 375                 380
Leu Glu Cys Ser His Leu Leu Thr Val Ile Lys Met Glu Glu Ala Gly
385                 390                 395                 400
Asp Glu Ile Val Ser Asn Ala Ile Ser Tyr Ala Leu Tyr Lys Ala Phe
                405                 410                 415
Ser Thr Ser Glu Gln Asp Lys Asp Asn Trp Asn Gly Gln Leu Lys Leu
            420                 425                 430
Leu Leu Glu Trp Asn Gln Leu Asp Leu Ala Asn Asp Glu Ile Phe Thr
        435                 440                 445
Asn Asp Arg Arg Trp Glu Ser Ala Asp Leu Gln Glu Val Met Phe Thr
    450                 455                 460
Ala Leu Ile Lys Asp Arg Pro Lys Phe Val Arg Leu Phe Leu Glu Asn
465                 470                 475                 480
Gly Leu Asn Leu Arg Lys Phe Leu Thr His Asp Val Leu Thr Glu Leu
                485                 490                 495
Phe Ser Asn His Phe Ser Thr Leu Val Tyr Arg Asn Leu Gln Ile Ala
            500                 505                 510
Lys Asn Ser Tyr Asn Asp Ala Leu Leu Thr Phe Val Trp Lys Leu Val
        515                 520                 525
Ala Asn Phe Arg Arg Gly Phe Arg Lys Glu Asp Arg Asn Gly Arg Asp
    530                 535                 540
Glu Met Asp Ile Glu Leu His Asp Val Ser Pro Ile Thr Arg His Pro
545                 550                 555                 560
Leu Gln Ala Leu Phe Ile Trp Ala Ile Leu Gln Asn Lys Lys Glu Leu
                565                 570                 575
Ser Lys Val Ile Trp Glu Gln Thr Arg Gly Cys Thr Leu Ala Ala Leu
            580                 585                 590
```

-continued

```
Gly Ala Ser Lys Leu Leu Lys Thr Leu Ala Lys Val Lys Asn Asp Ile
        595                 600                 605

Asn Ala Ala Gly Glu Ser Glu Glu Leu Ala Asn Glu Tyr Glu Thr Arg
610                 615                 620

Ala Val Glu Leu Phe Thr Glu Cys Tyr Ser Ser Asp Glu Asp Leu Ala
625                 630                 635                 640

Glu Gln Leu Leu Val Tyr Ser Cys Glu Ala Trp Gly Gly Ser Asn Cys
                645                 650                 655

Leu Glu Leu Ala Val Glu Ala Thr Asp Gln His Phe Ile Ala Gln Pro
            660                 665                 670

Gly Val Gln Asn Phe Leu Ser Lys Gln Trp Tyr Gly Glu Ile Ser Arg
        675                 680                 685

Asp Thr Lys Asn Trp Lys Ile Ile Leu Cys Leu Phe Ile Ile Pro Leu
    690                 695                 700

Val Gly Cys Gly Phe Val Ser Phe Arg Lys Lys Pro Val Asp Lys His
705                 710                 715                 720

Lys Lys Leu Leu Trp Tyr Tyr Val Ala Phe Phe Thr Ser Pro Phe Val
                725                 730                 735

Val Phe Ser Trp Asn Val Val Phe Tyr Ile Ala Phe Leu Leu Leu Phe
            740                 745                 750

Ala Tyr Val Leu Leu Met Asp Phe His Ser Val Pro His Pro Pro Glu
        755                 760                 765

Leu Val Leu Tyr Ser Leu Val Phe Val Leu Phe Cys Asp Glu Val Arg
    770                 775                 780

Gln Trp Tyr Val Asn Gly Val Asn Tyr Phe Thr Asp Leu Trp Asn Val
785                 790                 795                 800

Met Asp Thr Leu Gly Leu Phe Tyr Phe Ile Ala Gly Ile Val Phe Arg
                805                 810                 815

Leu His Ser Ser Asn Lys Ser Ser Leu Tyr Ser Gly Arg Val Ile Phe
            820                 825                 830

Cys Leu Asp Tyr Ile Ile Phe Thr Leu Arg Leu Ile His Ile Phe Thr
        835                 840                 845

Val Ser Arg Asn Leu Gly Pro Lys Ile Ile Met Leu Gln Arg Met Leu
    850                 855                 860

Ile Asp Val Phe Phe Phe Leu Phe Leu Phe Ala Val Trp Met Val Ala
865                 870                 875                 880

Phe Gly Val Ala Arg Gln Gly Ile Leu Arg Gln Asn Glu Gln Arg Trp
                885                 890                 895

Arg Trp Ile Phe Arg Ser Val Ile Tyr Glu Pro Tyr Leu Ala Met Phe
            900                 905                 910

Gly Gln Val Pro Ser Asp Val Asp Gly Thr Thr Tyr Asp Phe Ala His
        915                 920                 925

Cys Thr Phe Thr Gly Asn Glu Ser Lys Pro Leu Cys Val Glu Leu Asp
    930                 935                 940

Glu His Asn Leu Pro Arg Phe Pro Glu Trp Ile Thr Ile Pro Leu Val
945                 950                 955                 960

Cys Ile Tyr Met Leu Ser Thr Asn Ile Leu Leu Val Asn Leu Leu Val
                965                 970                 975

Ala Met Phe Gly Tyr Thr Val Gly Thr Val Gln Glu Asn Asn Asp Gln
            980                 985                 990

Val Trp Lys Phe Gln Arg Tyr Phe Leu Val Gln Glu Tyr Cys Ser Arg
        995                 1000                1005

Leu Asn Ile Pro Phe Pro Phe Ile Val Phe Ala Tyr Phe Tyr Met Val
```

```
                1010                1015                1020
Val Lys Lys Cys Phe Lys Cys Cys Lys Glu Lys Asn Met Glu Ser
1025                1030                1035                1040

Ser Val Cys Cys Phe Lys Asn Glu Asp Asn Glu Thr Leu Ala Trp Glu
                1045                1050                1055

Gly Val Met Lys Glu Asn Tyr Leu Val Lys Ile Asn Thr Lys Ala Asn
            1060                1065                1070

Asp Thr Ser Glu Glu Met Arg His Arg Phe Arg Gln Leu Asp Thr Lys
        1075                1080                1085

Leu Asn Asp Leu Lys Gly Leu Leu Lys Glu Ile Ala Asn Lys Ile Lys
    1090                1095                1100

<210> SEQ ID NO 12
<211> LENGTH: 1104
<212> TYPE: PRT
<213> ORGANISM: Mus sp.

<400> SEQUENCE: 12

Met Ser Phe Glu Gly Ala Arg Leu Ser Met Arg Ser Arg Arg Asn Gly
 1               5                  10                  15

Thr Met Gly Ser Thr Arg Thr Leu Tyr Ser Ser Val Ser Arg Ser Thr
            20                  25                  30

Asp Val Ser Tyr Ser Asp Ser Asp Leu Val Asn Phe Ile Gln Ala Asn
        35                  40                  45

Phe Lys Lys Arg Glu Cys Val Phe Phe Thr Arg Asp Ser Lys Ala Met
    50                  55                  60

Glu Asn Ile Cys Lys Cys Gly Tyr Ala Gln Ser Gln His Ile Glu Gly
65                  70                  75                  80

Thr Gln Ile Asn Gln Asn Glu Lys Trp Asn Tyr Lys Lys His Thr Lys
                85                  90                  95

Glu Phe Pro Thr Asp Ala Phe Gly Asp Ile Gln Phe Glu Thr Leu Gly
            100                 105                 110

Lys Lys Gly Lys Tyr Leu Arg Leu Ser Cys Asp Thr Asp Ser Glu Thr
        115                 120                 125

Leu Tyr Glu Leu Leu Thr Gln His Trp His Leu Lys Thr Pro Asn Leu
    130                 135                 140

Val Ile Ser Val Thr Gly Gly Ala Lys Asn Phe Ala Leu Lys Pro Arg
145                 150                 155                 160

Met Arg Lys Ile Phe Ser Arg Leu Ile Tyr Ile Ala Gln Ser Lys Gly
                165                 170                 175

Ala Trp Ile Leu Thr Gly Gly Thr His Tyr Gly Leu Met Lys Tyr Ile
            180                 185                 190

Gly Glu Val Val Arg Asp Asn Thr Ile Ser Arg Asn Ser Glu Glu Asn
        195                 200                 205

Ile Val Ala Ile Gly Ile Ala Ala Trp Gly Met Val Ser Asn Arg Asp
    210                 215                 220

Thr Leu Ile Arg Ser Cys Asp Asp Glu Gly His Phe Ser Ala Gln Tyr
225                 230                 235                 240

Ile Met Asp Asp Phe Thr Arg Asp Pro Leu Tyr Ile Leu Asp Asn Asn
                245                 250                 255

His Thr His Leu Leu Val Asp Asn Gly Cys His Gly His Pro Thr
            260                 265                 270

Val Glu Ala Lys Leu Arg Asn Gln Leu Glu Lys Tyr Ile Ser Glu Arg
        275                 280                 285
```

```
Thr Ser Gln Asp Ser Asn Tyr Gly Gly Lys Ile Pro Ile Val Cys Phe
290                 295                 300

Ala Gln Gly Gly Gly Arg Glu Thr Leu Lys Ala Ile Asn Thr Ser Val
305                 310                 315                 320

Lys Ser Lys Ile Pro Cys Val Val Glu Gly Ser Gly Gln Ile Ala
            325                 330                 335

Asp Val Ile Ala Ser Leu Val Glu Val Asp Val Leu Thr Ser Ser
            340                 345                 350

Met Val Lys Glu Lys Leu Val Arg Phe Leu Pro Arg Thr Val Ser Arg
        355                 360                 365

Leu Pro Glu Glu Glu Ile Glu Ser Trp Ile Lys Trp Leu Lys Glu Ile
370                 375                 380

Leu Glu Ser Ser His Leu Leu Thr Val Ile Lys Met Glu Glu Ala Gly
385                 390                 395                 400

Asp Glu Ile Val Ser Asn Ala Ile Ser Tyr Ala Leu Tyr Lys Ala Phe
            405                 410                 415

Ser Thr Asn Glu Gln Asp Lys Asp Asn Trp Asn Gly Gln Leu Lys Leu
            420                 425                 430

Leu Leu Glu Trp Asn Gln Leu Asp Leu Ala Ser Asp Glu Ile Phe Thr
        435                 440                 445

Asn Asp Arg Arg Trp Glu Ser Ala Asp Leu Gln Glu Val Met Phe Thr
450                 455                 460

Ala Leu Ile Lys Asp Arg Pro Lys Phe Val Arg Leu Phe Leu Glu Asn
465                 470                 475                 480

Gly Leu Asn Leu Gln Lys Phe Leu Thr Asn Glu Val Leu Thr Glu Leu
            485                 490                 495

Phe Ser Thr His Phe Ser Thr Leu Val Tyr Arg Asn Leu Gln Ile Ala
            500                 505                 510

Lys Asn Ser Tyr Asn Asp Ala Leu Leu Thr Phe Val Trp Lys Leu Val
        515                 520                 525

Ala Asn Phe Arg Arg Ser Phe Trp Lys Glu Asp Arg Ser Ser Arg Glu
530                 535                 540

Asp Leu Asp Val Glu Leu His Asp Ala Ser Leu Thr Thr Arg His Pro
545                 550                 555                 560

Leu Gln Ala Leu Phe Ile Trp Ala Ile Leu Gln Asn Lys Lys Glu Leu
            565                 570                 575

Ser Lys Val Ile Trp Glu Gln Thr Lys Gly Cys Thr Leu Ala Ala Leu
            580                 585                 590

Gly Ala Ser Lys Leu Leu Lys Thr Leu Ala Lys Val Lys Asn Asp Ile
        595                 600                 605

Asn Ala Ala Gly Glu Ser Glu Glu Leu Ala Asn Glu Tyr Glu Thr Arg
610                 615                 620

Ala Val Glu Leu Phe Thr Glu Cys Tyr Ser Asn Asp Glu Asp Leu Ala
625                 630                 635                 640

Glu Gln Leu Leu Val Tyr Ser Cys Glu Ala Trp Gly Gly Ser Asn Cys
            645                 650                 655

Leu Glu Leu Ala Val Glu Ala Thr Asp Gln His Phe Ile Ala Gln Pro
            660                 665                 670

Gly Val Gln Asn Phe Leu Ser Lys Gln Trp Tyr Gly Glu Ile Ser Arg
        675                 680                 685

Asp Thr Lys Asn Trp Lys Ile Ile Leu Cys Leu Phe Ile Ile Pro Leu
690                 695                 700

Val Gly Cys Gly Leu Val Ser Phe Arg Lys Lys Pro Ile Asp Lys His
```

```
                705                 710                 715                 720
Lys Lys Leu Leu Trp Tyr Tyr Val Ala Phe Phe Thr Ser Pro Phe Val
                    725                 730                 735
Val Phe Ser Trp Asn Val Val Phe Tyr Ile Ala Phe Leu Leu Leu Phe
                740                 745                 750
Ala Tyr Val Leu Leu Met Asp Phe His Ser Val Pro His Thr Pro Glu
                755                 760                 765
Leu Ile Leu Tyr Ala Leu Val Phe Val Leu Phe Cys Asp Glu Val Arg
            770                 775                 780
Gln Trp Tyr Met Asn Gly Val Asn Tyr Phe Thr Asp Leu Trp Asn Val
785                 790                 795                 800
Met Asp Thr Leu Gly Leu Phe Tyr Phe Ile Ala Gly Ile Val Phe Arg
                        805                 810                 815
Leu His Ser Ser Asn Lys Ser Ser Leu Tyr Ser Gly Arg Val Ile Phe
                    820                 825                 830
Cys Leu Asp Tyr Ile Ile Phe Thr Leu Arg Leu Ile His Ile Phe Thr
                835                 840                 845
Val Ser Arg Asn Leu Gly Pro Lys Ile Ile Met Leu Gln Arg Met Leu
            850                 855                 860
Ile Asp Val Phe Phe Phe Leu Phe Leu Phe Ala Val Trp Met Val Ala
865                 870                 875                 880
Phe Gly Val Ala Arg Gln Gly Ile Leu Arg Gln Asn Glu Gln Arg Trp
                        885                 890                 895
Arg Trp Ile Phe Arg Ser Val Ile Tyr Glu Pro Tyr Leu Ala Met Phe
                    900                 905                 910
Gly Gln Val Pro Ser Asp Val Asp Ser Thr Thr Tyr Asp Phe Ser His
                915                 920                 925
Cys Thr Phe Ser Gly Asn Glu Ser Lys Pro Leu Cys Val Glu Leu Asp
            930                 935                 940
Glu His Asn Leu Pro Arg Phe Pro Glu Trp Ile Thr Ile Pro Leu Val
945                 950                 955                 960
Cys Ile Tyr Met Leu Ser Thr Asn Ile Leu Leu Val Asn Leu Leu Val
                        965                 970                 975
Ala Met Phe Gly Tyr Thr Val Gly Ile Val Gln Glu Asn Asn Asp Gln
                    980                 985                 990
Val Trp Lys Phe Gln Arg Tyr Phe Leu Val Gln Glu Tyr Cys Asn Arg
                995                 1000                1005
Leu Asn Ile Pro Phe Pro Phe Val Phe Ala Tyr Phe Tyr Met Val
            1010                1015                1020
Val Lys Lys Cys Phe Lys Cys Cys Cys Lys Glu Lys Asn Met Glu Ser
1025                1030                1035                1040
Asn Ala Cys Cys Phe Arg Asn Glu Asp Asn Glu Thr Leu Ala Trp Glu
                        1045                1050                1055
Gly Val Met Lys Glu Asn Tyr Leu Val Lys Ile Asn Thr Lys Ala Asn
                    1060                1065                1070
Asp Asn Ser Glu Glu Met Arg His Arg Phe Arg Gln Leu Asp Ser Lys
                1075                1080                1085
Leu Asn Asp Leu Lys Ser Leu Leu Lys Glu Ile Ala Asn Asn Ile Lys
            1090                1095                1100
```

<210> SEQ ID NO 13
<211> LENGTH: 1104
<212> TYPE: PRT
<213> ORGANISM: Rattus sp.

<400> SEQUENCE: 13

```
Met Ser Phe Glu Gly Ala Arg Leu Ser Met Arg Ser Arg Arg Asn Gly
  1               5                  10                  15

Thr Leu Gly Ser Thr Arg Thr Leu Tyr Ser Ser Val Ser Arg Ser Thr
             20                  25                  30

Asp Val Ser Tyr Ser Glu Ser Asp Leu Val Asn Phe Ile Gln Ala Asn
         35                  40                  45

Phe Lys Lys Arg Glu Cys Val Phe Phe Thr Arg Asp Ser Lys Ala Met
     50                  55                  60

Glu Ser Ile Cys Lys Cys Gly Tyr Ala Gln Ser Gln His Ile Glu Gly
 65                  70                  75                  80

Thr Gln Ile Asn Gln Asn Glu Lys Trp Asn Tyr Lys Lys His Thr Lys
                 85                  90                  95

Glu Phe Pro Thr Asp Ala Phe Gly Asp Ile Gln Phe Glu Thr Leu Gly
            100                 105                 110

Lys Lys Gly Lys Tyr Leu Arg Leu Ser Cys Asp Thr Asp Ser Glu Thr
        115                 120                 125

Leu Tyr Glu Leu Leu Thr Gln His Trp His Leu Lys Thr Pro Asn Leu
    130                 135                 140

Val Ile Ser Val Thr Gly Gly Ala Lys Asn Phe Ala Leu Lys Pro Arg
145                 150                 155                 160

Met Arg Lys Ile Phe Ser Arg Leu Ile Tyr Ile Ala Gln Ser Lys Gly
                165                 170                 175

Ala Trp Ile Leu Thr Gly Gly Thr His Tyr Gly Leu Met Lys Tyr Ile
            180                 185                 190

Gly Glu Val Val Arg Asp Asn Thr Ile Ser Arg Asn Ser Glu Glu Asn
        195                 200                 205

Ile Val Ala Ile Gly Ile Ala Ala Trp Gly Met Val Ser Asn Arg Asp
    210                 215                 220

Thr Leu Ile Arg Asn Cys Asp Asp Glu Gly His Phe Ser Ala Gln Tyr
225                 230                 235                 240

Ile Met Asp Asp Phe Met Arg Asp Pro Leu Tyr Ile Leu Asp Asn Asn
                245                 250                 255

His Thr His Leu Leu Val Asp Asn Gly Cys His Gly His Pro Thr
            260                 265                 270

Val Glu Ala Lys Leu Arg Asn Gln Leu Glu Lys Tyr Ile Ser Glu Arg
        275                 280                 285

Thr Ser Gln Asp Ser Asn Tyr Gly Gly Lys Ile Pro Ile Val Cys Phe
    290                 295                 300

Ala Gln Gly Gly Gly Arg Glu Thr Leu Lys Ala Ile Asn Thr Ser Val
305                 310                 315                 320

Lys Ser Lys Ile Pro Cys Val Val Glu Gly Ser Gly Gln Ile Ala
                325                 330                 335

Asp Val Ile Ala Ser Leu Val Glu Val Glu Asp Val Leu Thr Ser Ser
            340                 345                 350

Met Val Lys Glu Lys Leu Val Arg Phe Leu Pro Arg Thr Val Ser Arg
        355                 360                 365

Leu Pro Glu Glu Glu Ile Glu Ser Trp Ile Lys Trp Leu Lys Glu Ile
    370                 375                 380

Leu Glu Ser Pro His Leu Leu Thr Val Ile Lys Met Glu Glu Ala Gly
385                 390                 395                 400

Asp Glu Val Val Ser Ser Ala Ile Ser Tyr Ala Leu Tyr Lys Ala Phe
```

-continued

```
                405                 410                 415
Ser Thr Asn Glu Gln Asp Lys Asp Asn Trp Asn Gly Gln Leu Lys Leu
                420                 425                 430

Leu Leu Glu Trp Asn Gln Leu Asp Leu Ala Ser Asp Glu Ile Phe Thr
            435                 440                 445

His Asp Arg Arg Trp Glu Ser Ala Asp Leu Gln Glu Val Met Phe Thr
        450                 455                 460

Ala Leu Ile Lys Asp Arg Pro Lys Phe Val Arg Leu Phe Leu Glu Asn
465                 470                 475                 480

Gly Leu Asn Leu Gln Lys Phe Leu Thr Asn Glu Val Leu Thr Glu Leu
                485                 490                 495

Phe Ser Thr His Phe Ser Thr Leu Val Tyr Arg Asn Leu Gln Ile Ala
            500                 505                 510

Lys Asn Ser Tyr Asn Asp Ala Leu Leu Thr Phe Val Trp Lys Leu Val
        515                 520                 525

Ala Asn Phe Arg Arg Ser Phe Trp Lys Glu Asp Arg Ser Ser Arg Glu
530                 535                 540

Asp Leu Asp Val Glu Leu His Asp Ala Ser Leu Thr Thr Arg His Pro
545                 550                 555                 560

Leu Gln Ala Leu Phe Ile Trp Ala Ile Leu Gln Asn Lys Lys Glu Leu
            565                 570                 575

Ser Lys Val Ile Trp Glu Gln Thr Lys Gly Cys Thr Leu Ala Ala Leu
        580                 585                 590

Gly Ala Ser Lys Leu Leu Lys Thr Leu Ala Lys Val Lys Asn Asp Ile
        595                 600                 605

Asn Ala Ala Gly Glu Ser Glu Glu Leu Ala Asn Glu Tyr Glu Thr Arg
    610                 615                 620

Ala Val Glu Leu Phe Thr Glu Cys Tyr Ser Ser Asp Glu Asp Leu Ala
625                 630                 635                 640

Glu Gln Leu Leu Val Tyr Ser Cys Glu Ala Trp Gly Gly Ser Asn Cys
                645                 650                 655

Leu Glu Leu Ala Val Glu Ala Thr Asp Gln His Phe Ile Ala Gln Pro
            660                 665                 670

Gly Val Gln Asn Phe Leu Ser Lys Gln Trp Tyr Gly Glu Ile Ser Arg
        675                 680                 685

Asp Thr Lys Asn Trp Lys Ile Ile Leu Cys Leu Phe Ile Ile Pro Leu
    690                 695                 700

Val Gly Cys Gly Leu Val Ser Phe Arg Lys Lys Pro Ile Asp Lys His
705                 710                 715                 720

Lys Lys Leu Leu Trp Tyr Tyr Val Ala Phe Phe Thr Ser Pro Phe Val
                725                 730                 735

Val Phe Ser Trp Asn Val Val Phe Tyr Ile Ala Phe Leu Leu Leu Phe
            740                 745                 750

Ala Tyr Val Leu Leu Met Asp Phe His Ser Val Pro His Thr Pro Glu
        755                 760                 765

Leu Ile Leu Tyr Ala Leu Val Phe Val Leu Phe Cys Asp Glu Val Arg
    770                 775                 780

Gln Trp Tyr Met Asn Gly Val Asn Tyr Phe Thr Asp Leu Trp Asn Val
785                 790                 795                 800

Met Asp Thr Leu Gly Leu Phe Tyr Phe Ile Ala Gly Ile Val Phe Arg
                805                 810                 815

Leu His Ser Ser Asn Lys Ser Ser Leu Tyr Ser Gly Arg Val Ile Phe
            820                 825                 830
```

```
Cys Leu Asp Tyr Ile Ile Phe Thr Leu Arg Leu Ile His Ile Phe Thr
            835                 840                 845

Val Ser Arg Asn Leu Gly Pro Lys Ile Ile Met Leu Gln Arg Met Leu
        850                 855                 860

Ile Asp Val Phe Phe Leu Phe Leu Phe Ala Val Trp Met Val Ala
865             870                 875                 880

Phe Gly Val Ala Arg Gln Gly Ile Leu Arg Gln Asn Glu Gln Arg Trp
                885                 890                 895

Arg Trp Ile Phe Arg Ser Val Ile Tyr Glu Pro Tyr Leu Ala Met Phe
            900                 905                 910

Gly Gln Val Pro Ser Asp Val Asp Ser Thr Thr Tyr Asp Phe Ser His
            915                 920                 925

Cys Thr Phe Ser Gly Asn Glu Ser Lys Pro Leu Cys Val Glu Leu Asp
            930                 935                 940

Glu Tyr Asn Leu Pro Arg Phe Pro Glu Trp Ile Thr Ile Pro Leu Val
945             950                 955                 960

Cys Ile Tyr Met Leu Ser Thr Asn Ile Leu Leu Val Asn Leu Leu Val
                965                 970                 975

Ala Met Phe Gly Tyr Thr Val Gly Ile Val Gln Glu Asn Asn Asp Gln
                980                 985                 990

Val Trp Lys Phe Gln Arg Tyr Phe Leu Val Gln Glu Tyr Cys Asn Arg
            995                 1000                1005

Leu Asn Ile Pro Phe Pro Phe Val Val Phe Ala Tyr Phe Tyr Met Val
            1010                1015                1020

Val Lys Lys Cys Phe Lys Cys Cys Cys Lys Glu Lys Asn Thr Glu Ser
1025                1030                1035                1040

Ser Ala Cys Cys Phe Arg Asn Glu Asp Asn Glu Thr Leu Ala Trp Glu
                1045                1050                1055

Gly Val Met Lys Glu Asn Tyr Leu Val Lys Ile Asn Thr Lys Ala Asn
                1060                1065                1070

Asp Asn Ala Glu Glu Met Arg His Arg Phe Arg Gln Leu Asp Thr Lys
            1075                1080                1085

Leu Asn Asp Leu Lys Gly Leu Leu Lys Glu Ile Ala Asn Lys Ile Lys
            1090                1095                1100
```

CANINE COLD- AND MENTHOL-SENSITIVE RECEPTOR 1

CROSS-REFERENCE TO RELATED APPLICATIONS

This application claims priority to U.S. Application Nos. 60/560,400 filed on Apr. 8, 2004 and 60/621,223 filed on Oct. 22, 2004, the entire contents of which are incorporated by reference herein.

FIELD OF THE INVENTION

The present invention relates to thermal receptor ion channel proteins. In particular, the present invention relates to isolated nucleic acid molecules and polypeptides of a novel canine cold- and menthol-sensitive receptor, CMR1, and uses thereof.

BACKGROUND

Considerable efforts have been put into elucidating the biochemical mechanisms involved in the detection, transduction and transmission of hot and cold sensations in neuronal tissues. Thermal stimuli activate specialized receptors located on sensory neurons, such as those deriving from the dorsal root ganglion (DRG) and the trigeminal ganglion (TG). When these stimuli are in the noxious range (i.e, very hot or cold), they activate a certain subset of thermal receptors on a sub-population of sensory neurons called nociceptors (pain-sensing neurons). Upon activation, the thermal receptors (e.g., ion channels) transduce the noxious stimulus into an electrical signal that is propagated along the sensory neuron to the spinal cord, where it is relayed to the brain, ultimately leading to the perception of pain. Accordingly, these thermal receptors represent highly promising targets for developing drugs for the treatment of various painful conditions.

Several temperature-activated receptors have been implicated in sensing heat. TRPV1 (VR1: a capsaicin- and heat-activated channel) is activated near 43° C., a temperature most mammals perceive as noxious. Other TRPV channels with greater than 40% amino acid level identity to TRPV1 also have been cloned and characterized as thermosensors. These channels are activated at various heat thresholds, ranging from 39° C. (warm) for TRPV3 to 55° C. (high-threshold noxious heat) for TRPV2/VRL1 (See Story et al., Cell, 2003, 112:819-829, and references therein). In contrast, TRPV4 is constitutively opened at room temperature being activated at temperatures greater than approximately 27° C. (Güler et al., J. Neurosci. 2002). These temperature-activated receptors belong to the transient receptor potential (TRP) family of non-selective cation channels, which in *C. elegans* and *D. melanogaster* are involved in mechano- and osmoregulation. TRP channels are divided into three subfamilies designated TRPC (canonical or capacitive subfamily), TRPV (vanilloid subfamily), and TRPM (melanostatin subfamily). All have six putative transmembrane domains with a proposed pore region between transmembrane domains five and six. TRP channels are thought to have cytoplasmic N- and C termini (See Story et al., supra, and references therein).

More recently, proteins have been discovered that fall within the TRP family of proteins and modulate responses to cold stimuli. A rat CMR1 protein (for "cold- and menthol-sensitive receptor"; McKemy, D. D., et al., Nature, 416:52-58, 2002) and a mouse TRPM8 protein (for "transient receptor potential channel, melanostatin subfamily, type 8"; Peier, A. M. et al., Cell 108:705-715, 2002) appear to function as excitatory ion channels that are activated upon exposure to relatively low temperatures. The threshold of TRPM8 activation is approximately about 23° C. The rat CMR1 and mouse TRPM8 are also sensitive to compounds that provoke cold sensations, such as menthol and icilin. Interestingly, the rat CMR1 and mouse TRPM8 share over 90% sequence identity over the entire length of their amino acid sequences.

There is a need to identify additional thermal receptors, as they are potential targets for the treatment of pain. There is also a need to identify thermal receptors in different species, as they can be used as model systems to investigate the effects of test compounds. Particularly, there is a need for systems that can be used to test compounds that potentially increase or decrease the activity of a thermal receptor responding to cold stimuli. Identification and testing of such compounds would enable the treatment of various disorders associated with chronic pain or for uses in other conditions in which tissue cooling is desirable.

SUMMARY

It has now been discovered that a canine protein, designated canine CMR1 (cCMR1) herein, modulates responses to cold stimuli and belongs to the TRP family of proteins.

In one general aspect, the invention provides an isolated nucleic acid molecule comprising a nucleotide sequence that encodes a polypeptide capable of detecting and transducing cold stimuli and having at least 96% sequence identity to SEQ ID NO: 2. In one embodiment, the invention provides an isolated nucleic acid molecule comprising a nucleotide sequence encoding a cCMR1 protein having an amino acid sequence of SEQ ID NO: 2. The invention also provides expression vectors or recombinant host cells comprising a nucleic acid molecule of the invention. The invention further provides a nucleic acid probe that selectively hybridizes to the nucleic acid molecule of the invention under stringent hybridization conditions, and a kit comprising such a probe.

In another general aspect, the invention provides a substantially purified polypeptide capable of detecting and transducing cold stimuli and having at least 96% sequence identity to SEQ ID NO: 2. In one embodiment, the invention provides a substantially purified polypeptide comprising a cCMR1 protein having an amino acid sequence of SEQ ID NO: 2. The invention also provides a method of expressing the polypeptide of the invention, comprising the steps of: a) introducing an expression vector capable of encoding a polypeptide of the invention into a cell; and b) culturing the cells under conditions that allow expression of the polypeptide from the expression vector. The invention further provides an antibody that binds selectively to a polypeptide of the invention, and a kit comprising such an antibody.

The invention provides methods of detecting a nucleic acid molecule or polypeptide of the invention, comprising the step of contacting the nucleic acid molecule or polypeptide with an agent capable of binding specifically to the nucleic acid molecule or polypeptide.

The invention provides a method of identifying a compound that increases or decreases the expression of a cCMR1 protein, comprising the steps of:
(a) contacting a test compound with a cell comprising a mechanism for regulating the expression of the cCMR gene; and (b) determining whether the test compound increases or decreases the expression of a gene controlled by said mechanism from the cell.

The invention also provides a method of identifying a compound that increases or decreases the conductivity of a cCMR1 ion channel, comprising the steps of: (a) contacting a test compound with the ion channel; and (b) determining whether the test compound increases or decreases the conductivity of the ion channel.

Other aspects of the invention include a method of identifying a compound that increases or decreases the conductivity of a mammalian CMR1 ion channel, comprising the steps of: (a) incubating the ion channel in a buffer solution containing a sub-inactivating amount of calcium; (b) activating the ion channel; (c) contacting the ion channel with a test compound; (d) increasing the amount of calcium in the buffer solution; and c) determining the intracellular amount of calcium, and comparing the amount with that of a control wherein the ion channel was not contacted with the test compound.

In addition, the invention provides a method of identifying a compound useful for treating pain, comprising the steps of: (a) contacting a test compound with a cCMR1 ion channel; and (b) determining whether the test compound increases or decreases the conductivity of the ion channel. In some embodiments, the method further comprises the steps of: (a) administering the test compound to an animal; and (b) determining the extent to which the test compound alters the nociceptive/nocifensive response of the animal.

Other aspects, features and advantages of the invention will be apparent from the following disclosure, including the detailed description of the invention and its preferred embodiments and the appended claims.

DETAILED DESCRIPTION

Figure 1:
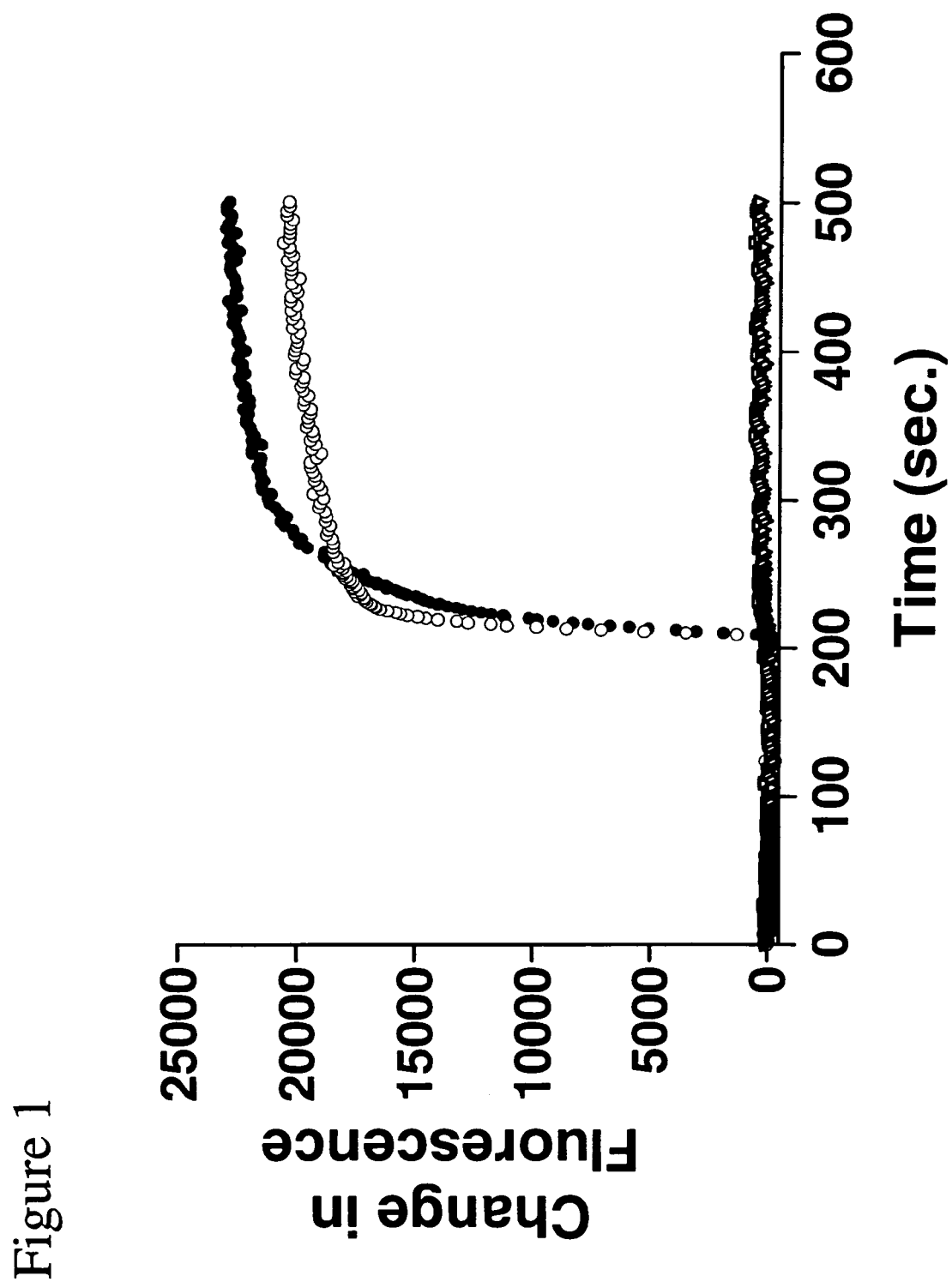
FIG. 1 illustrates results of a cell-based calcium influx assay on recombinant cells stably transfected with a canine CMR1 expression vector. The cells showed an increase in calcium-mediated fluorescence in response to 10 µM of icilin (filled circle); or 100 µM of (−)-menthol (open circle). The compounds were added to the cells at time point 200 seconds. No calcium influx was observed upon the addition of buffer only to the cells (open triangle).

All publications cited herein are hereby incorporated by reference. Unless defined otherwise, all technical and scientific terms used herein have the same meaning as commonly understood to one of ordinary skill in the art to which this invention pertains.

As used herein, the terms "comprising", "containing", "having" and "including" are used in their open, non-limiting sense.

The following are abbreviations that are at times used in this specification:

bp=base pair
cDNA=complementary DNA
CMR1=cold- and menthol-sensitive receptor 1;
cCMR1=canine cold- and menthol-sensitive receptor 1;
DRG=dorsal root ganglion
ELISA=enzyme-linked immunoabsorbent assay
FLIPR=fluorescence imaging plate reader
kb=kilobase; 1000 base pairs
nt=nucleotide
PAGE=polyacrylamide gel electrophoresis
PCR=polymerase chain reaction
RT-PCR=Reverse transcription polymerase chain reaction
SDS=sodium dodecyl sulfate
SSC=sodium chloride/sodium citrate
TG=trigeminal ganglion
TRPM8=transient receptor potential channel, melanostatin subfamily, type 8
UTR=untranslated region "An activity", "a biological activity", or "a functional activity" of a polypeptide or nucleic acid refers to an activity exerted by a polypeptide or nucleic acid molecule as determined in vivo, or in vitro, according to standard techniques. Such activities can be a direct activity, such as an ion channel activity, an association with or an enzymatic activity on a second protein, or an indirect activity, such as a cellular signaling activity mediated by interaction of the protein with one or more than one additional protein or other molecule(s), including but not limited to, interactions that occur in a multi-step, serial fashion.

A "biological sample" as used herein refers to a sample containing or consisting of cell or tissue matter, such as cells or biological fluids isolated from a subject. The "subject" can be a mammal, such as a rat, a mouse, a monkey, or a human, that has been the object of treatment, observation or experiment. Examples of biological samples include, for example, sputum, blood, blood cells (e.g., white blood cells), amniotic fluid, plasma, semen, bone marrow, tissue or fine-needle biopsy samples, urine, peritoneal fluid, pleural fluid, and cell cultures. Biological samples may also include sections of tissues such as frozen sections taken for histological purposes. A test biological sample is the biological sample that has been the object of analysis, monitoring, or observation. A control biological sample can be either a positive or a negative control for the test biological sample. Often, the control biological sample contains the same type of tissues, cells and/or biological fluids of interest as that of the test biological sample.

A "cell" refers to at least one cell or a plurality of cells appropriate for the sensitivity of the detection method. Cells suitable for the present invention may be bacterial, but are preferably eukaryotic, and are most preferably mammalian.

A "clone" is a population of cells derived from a single cell or common ancestor by mitosis. A "cell line" is a primary cell, that derives clonal expansion of cells and is capable of stable growth in vitro for many generations.

A "cold- and menthol-sensitive receptor", a "CMR1", a "transient receptor potential channel, melanostatin subfamily, type 8", or a "TRPM8" protein, each refers to a protein that is capable of sensing and transducing cold stimuli, such as cold temperatures or compounds that provoke cold sensations including, but not limited to, menthol and icilin. A "CMR1" can form an excitory ion channel, the CMR1 channel, which can be activated by low temperature or compounds that provoke cold sensations. An activated CMR1 channel gates the influx of $Ca^{++}$ ions through the channel, resulting in membrane depolarization. A CMR1 protein can, (1) have greater than about 80% amino acid sequence identity to a canine CMR1 (cCMR1) protein depicted in SEQ ID NO: 2; or (2) bind to antibodies, e.g., polyclonal or monoclonal antibodies, raised against a cCMR1 protein depicted in SEQ ID NO: 2. In some embodiments, the CMR1 has greater than about 85, 90, or 95 percent amino acid sequence identity to SEQ ID NO: 2. Exemplary CMR1 includes cCMR1, which includes structural and functional polymorphisms of the cCMR1 protein depicted in SEQ ID NO: 2. "Polymorphism" refers to a set of genetic variants at a particular genetic locus among individuals in a population. CMR1 also includes orthologs of the canine CMR1 in other animals including human, rat, mouse, pig, dog and monkey, for example, the structural and functional polymorphisms of the rat CMR1 (GenBank protein ID: NP_599198), or mouse TRPM8 (GenBank protein ID: NP_599013). CMR1 genes are naturally expressed in certain neuronal tissues, such as DRG and TG.

"CMR1 activation temperature" is the temperature at which a CMR1 channel exhibits at least a 10% increase in its conductivity compared to the baseline. A person skilled in the art can experimentally determine the activation temperature for a CMR1 channel. In some embodiments, "CMR1 activation temperature" is the temperature at which a CMR1 channel exhibits at least a 15%, 20%, 25%, 30%, 35%, 40%, 45%, or 50% increase in its conductivity compared to the baseline. "CMR1 activation temperature" is typically of about 6° C.-28° C. In some embodiments, the CMR1 activation temperature is about 15° C.-28° C., 19° C.-28° C., 23° C.-28° C., or, 19° C.-24° C.

"CMR1 non-activation temperature" is the temperature that falls outside of the range for a "CMR1 activation temperature". An exemplary CMR1 non-activation temperature is 37° C.

A "gene" is a segment of DNA involved in producing a peptide, polypeptide, or protein, and the mRNA encoding such protein species, including the coding region, non-coding regions preceding ("5' UTR") and following ("3' UTR") the coding region. A "gene" may also include intervening non-coding sequences ("introns") between individual coding segments ("exons"). "Promoter" means a regulatory sequence of DNA that is involved in the binding of RNA polymerase to initiate transcription of a gene. Promoters are often upstream ("5' to") the transcription initiation site of the gene. A "regulatory sequence" refers to the portion of a gene that can control the expression of the gene. A "regulatory sequence" can include promoters, enhancers and other expression control elements such as polyadenylation signals, ribosome binding site (for bacterial expression), and/or, an operator. An "enhancer" means a regulatory sequence of DNA that can regulate the expression of a gene in a distance- and orientation-dependent fashion. A "coding region" refers to the portion of a gene that encodes amino acids and the start and stop signals for the translation of the corresponding polypeptide via triplet-base codons.

"Nucleic acid sequence" or "nucleotide sequence" refers to the arrangement of either deoxyribonucleotide or ribonucleotide residues in a polymer in either single- or double-stranded form. Nucleic acid sequences can be composed of natural nucleotides of the following bases: thymidine, adenine, cytosine, guanine, and uracil; abbreviated T, A, C, G, and U, respectively, and/or synthetic analogs.

The term "oligonucleotide" refers to a single-stranded DNA or RNA sequence of a relatively short length, for example, less than 100 residues long. For many methods, oligonucleotides of about 16-25 nucleotides in length are useful, although longer oligonucleotides of greater than about 25 nucleotides may sometimes be utilized. Some oligonucleotides can be used as "primers" for the synthesis of complimentary nucleic acid strands. For example, DNA primers can hybridize to a complimentary nucleic acid sequence to prime the synthesis of a complimentary DNA strand in reactions using DNA polymerases. Oligonucleotides are also useful for hybridization in several methods of nucleic acid detection, for example, in Northern blotting or in situ hybridization.

A "polypeptide sequence" or "protein sequence" refers to the arrangement of amino acid residues in a polymer. Polypeptide sequences can be composed of the standard 20 naturally occurring amino acids, in addition to rare amino acids and synthetic amino acid analogs. Shorter polypeptides are generally referred to as peptides.

An "isolated" nucleic acid molecule is one that is separated from other nucleic acid molecules present in the natural source of the nucleic acid. An "isolated" nucleic acid molecule can be, for example, a nucleic acid molecule that is free of at least one of the nucleotide sequences that naturally flank the nucleic acid molecule at its 5' and 3' ends in the genomic DNA of the organism from which the nucleic acid is derived. Isolated nucleic acid molecules include, without limitation, separate nucleic acid molecules (e.g., cDNA or genomic DNA fragments produced by PCR or restriction endonuclease treatment) independent of other sequences, as well as nucleic acid molecules that are incorporated into a vector, an autonomously replicating plasmid, a virus (e.g., a retrovirus, adenovirus, or herpes virus), or into the genomic DNA of a prokaryote or eukaryote. In addition, an isolated nucleic acid molecule can include a nucleic acid molecule that is part of a hybrid or fusion nucleic acid molecule. An isolated nucleic acid molecule can be a nucleic acid sequence that is: (i) amplified in vitro by, for example, polymerase chain reaction (PCR); (ii) synthesized by, for example, chemical synthesis; (iii) recombinantly produced by cloning; or (iv) purified, as by cleavage and electrophoretic or chromatographic separation.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals that are involved in the synthesis of the protein. Accordingly such preparations of the protein have less than about 30%, 20%, 10%, 5% (by dry weight) of chemical precursors or compounds other than the polypeptide of interest. Isolated biologically active polypeptide can have several different physical forms. The isolated polypeptide can exist as a full-length nascent or unprocessed polypeptide, or as a partially processed polypeptide or as a combination of processed polypeptides. The full-length nascent polypeptide can be postranslationally modified by specific proteolytic cleavage events that result in the formation of fragments of the full-length nascent polypeptide. A fragment, or physical association of fragments can have the biological activity associated with the full-length polypeptide; however, the degree of biological activity associated with individual fragments can vary. An isolated or substantially purified polypeptide, can be a polypeptide encoded by an isolated nucleic acid sequence, as well as a polypeptide synthesized by, for example, chemical synthetic methods, and a polypeptide separated from biological materials, and then purified, using conventional protein analytical or preparatory procedures, to an extent that permits it to be used according to the methods described herein.

"Recombinant" refers to a nucleic acid, a protein encoded by a nucleic acid, a cell, or a viral particle, that has been modified using molecular biology techniques to something other than its natural state. For example, recombinant cells can contain nucleotide sequence that is not found within the native (non-recombinant) form of the cell or can express native genes that are otherwise abnormally expressed, under-expressed, or not expressed at all. Recombinant cells can also contain genes found in the native form of the cell wherein the genes are modified and re-introduced into the cell by artificial means. The term also encompasses cells that contain an endogenous nucleic acid that has been modified without removing the nucleic acid from the cell; such modifications include those obtained, for example, by gene replacement, and site-specific mutation.

A "recombinant host cell" is a cell that has had introduced into it a recombinant DNA sequence. Recombinant DNA sequence can be introduced into host cells using any suitable method including, for example, electroporation, calcium phosphate precipitation, microinjection, transformation, biolistics and viral infection. Recombinant DNA may or may not be integrated (covalently linked) into chromosomal DNA making up the genome of the cell. For example, the recombinant DNA can be maintained on an episomal element, such as a plasmid. Alternatively, with respect to a stably transformed or transfected cell, the recombinant DNA has become integrated into the chromosome so that it is inherited by daughter cells through chromosome replication. This stability is demonstrated by the ability of the stably transformed or transfected cell to establish cell lines or clones comprised of a population of daughter cells containing the exogenous DNA. Recombinant host cells may be prokaryotic or eukaryotic, including bacteria such as *E. coli*, fungal cells such as yeast, mammalian cells such as cell lines of human, bovine, porcine, monkey and rodent origin, and insect cells such as *Drosophila*- and silkworm-derived cell lines. It is further understood that the term "recombinant host cell" refers not only to the particular subject cell, but also to the progeny or potential progeny of such a cell. Because certain modifications can occur in succeeding generations due to either mutation or environmental influences, such progeny may not, in fact, be identical to the parent cell, but are still included within the scope of the term as used herein.

As used herein, "operably linked", refers to a functional relationship between two nucleic acid sequences. For example, a promoter sequence that controls expression (for example, transcription) of a coding sequence is operably linked to that coding sequence. Operably linked nucleic acid sequences can be contiguous, typical of many promoter sequences, or non-contiguous, in the case of, for example, nucleic acid sequences that encode repressor proteins. Within a recombinant expression vector, "operably linked" is intended to mean that the coding sequence of interest is linked to the regulatory sequence(s) in a manner that allows for expression of the coding sequence, e.g., in an in vitro transcription/translation system or in a host cell when the vector is introduced into the host cell.

"Vector" or "construct" refers to a nucleic acid molecule into which a heterologous nucleic acid can be or is inserted. Some vectors can be introduced into a host cell allowing for replication of the vector or for expression of a protein that is encoded by the vector or construct. Vectors typically have selectable markers, for example, genes that encode proteins allowing for drug resistance, origins of replication sequences, and multiple cloning sites that allow for insertion of a heterologous sequence. Vectors are typically plasmid-based and are designated by a lower case "p" followed by a combination of letters and/or numbers. Starting plasmids disclosed herein are either commercially available, publicly available on an unrestricted basis, or can be constructed from available plasmids by application of procedures known in the art. Many plasmids and other cloning and expression vectors that can be used in accordance with the present invention are well-known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

"Sequence" means the linear order in which monomers occur in a polymer, for example, the order of amino acids in a polypeptide or the order of nucleotides in a polynucleotide.

"Sequence identity or similarity", as known in the art, is the relationship between two or more polypeptide sequences or two or more polynucleotide sequences, as determined by comparing the sequences. As used herein, "identity", in the context of the relationship between two or more nucleic acid sequences or two or more polypeptide sequences, refers to the percentage of nucleotide or amino acid residues, respectively, that are the same when the sequences are optimally aligned and analyzed. For purposes of comparing a queried sequence against, for example, the amino acid sequence SEQ ID NO 2, the queried sequence is optimally aligned with SEQ ID NO 2 and the best local alignment over the entire length of SEQ ID NO 2 (1104 amino acids) is obtained.

Analysis can be carried out manually or using sequence comparison algorithms. For sequence comparison, typically one sequence acts as a reference sequence, to which a queried sequence is compared. When using a sequence comparison algorithm, test and reference sequences are input into a computer, sub-sequence coordinates are designated, if necessary, and sequence algorithm program parameters are designated.

Optimal alignment of sequences for comparison can be conducted, for example, by using the homology alignment algorithm of Needleman & Wunsch, J Mol. Biol., 48:443 (1970). Software for performing Needleman & Wunsch analyses is publicly available through the Institut Pasteur (France) Biological Software website. The NEEDLE program uses the Needleman-Wunsch global alignment algorithm to find the optimum alignment (including gaps) of two sequences when considering their entire length. The identity is calculated along with the percentage of identical matches between the two sequences over the reported aligned region, including any gaps in the length. Similarity scores are also provided wherein the similarity is calculated as the percentage of matches between the two sequences over the reported aligned region, including any gaps in the length. Standard comparisons utilize the EBLOSUM62 matrix for protein sequences and the EDNAFULL matrix for nucleotide sequences. The gap open penalty is the score taken away when a gap is created; the default setting using the gap open penalty is 10.0. For gap extension, a penalty is added to the standard gap penalty for each base or residue in the gap; the default setting is 0.5.

Hybridization can also be used as a test to indicate that two polynucleotides are substantially identical to each other. Polynucleotides that share a high degree of identity will hybridize to each other under stringent hybridization conditions. "Stringent hybridization conditions" has the meaning known in the art, as described in Sambrook et al., *Molecular Cloning: A Laboratory Manual*, Second Edition, Cold Spring Harbor Laboratory, Cold Spring Harbor, N.Y., (1989). An exemplary stringent hybridization condition comprises hybridization in 6× sodium chloride/sodium citrate (SSC) at about 45° C., followed by one or more washes in 0.2×SSC and 0.1% SDS at 50-65° C., depending upon the length over which the hybridizing polynucleotides share complementarity.

A "reporter gene" refers to a nucleic acid sequence that encodes a reporter gene product. As is known in the art, reporter gene products are typically easily detectable by standard methods. Exemplary suitable reporter genes include, but are not limited to, genes encoding luciferase (lux), β-galactosidase (lacZ), green fluorescent protein (GFP), chloramphenicol acetyltransferase (CAT), β-glucuronidase, neomycin phosphotransferase, and guanine xanthine phosphoribosyl-transferase proteins.

A "compound that increases the conductivity of a CMR1 channel" includes any compound that results in increased passage of ions through the CMR1 channel. In one embodiment, such a compound is an agonist for the CMR channel that binds to the CMR1 channel to increase its conductivity. In another embodiment, such a compound is a positive allosteric modulator, which interacts with the CMR1 channel at allosteric sites different from the agonist binding-site, but potentiates the response of the channel to an agonist.

A "compound that decreases the conductivity of a CMR1 channel" includes any compound that results in decreased passage of ions through the CMR1 channel. In one embodiment, such a compound is an antagonist for the CMR channel that binds to the CMR1 channel to counter, decrease or limit the action of an agonist in either a competitive or non-competitive fashion. In another embodiment, such a compound is a negative allosteric modulator, which interacts with the CMR1 channel at allosteric sites different from the agonist or antagonist binding-site, and decreases the response of the channel to an agonist. In yet another embodiment, such a compound is an inverse agonist that binds to the CMR1 channel and decreases the conductivity of the channel in the absence of any other compound, such as an agonist.

"Membrane potential", "transmembrane potential" or "transmembrane potential difference" as used herein, each refers to the electrical potential difference across the plasma membrane, the external, limiting lipid bilayer membrane of cells. Almost all animal cells are negative inside, with resting potentials in the range −20 to −100 mV. "Resting potential" as used herein refers to the electrical potential of the inside of a cell relative to its surroundings when the cell is at rest.

"Depolarization" as used herein refers to the tendency of the cell membrane potential to become more positive, for example from −90 mV to −50 mV.

"Hyperpolarization" as used herein refers to the tendency of the cell membrane potential to become more negative, for example from −50 mV to −90 mV. In practicing the present invention, many conventional techniques in molecular biology, microbiology and recombinant DNA are used. These techniques are well-known and are explained in, for example, Current Protocols in Molecular Biology, Vols. I, II, and III, F. M. Ausubel, ed. (1997); and Sambrook et al., Molecular Cloning: A Laboratory Manual, Cold Spring Harbor Laboratory Press, Cold Spring Harbor, N.Y. (2001).

In one aspect, the present invention relates to novel cCMR1 (cCMR1) nucleic acids, polypeptides encoded by these nucleic acids, recombinant cCMR1 materials, and methods involving the production, detection, and utilization of these materials.

The CMR1 nomenclature was established by McKemy, D. D., et al. (Nature, 416:52-58, 2002) and was used to describe a cold- and menthol-sensitive receptor expressed in DRG and TG neurons of rats. The human CMR1 (also known as human TRPM8) is 92% identical to the amino acid sequence of rat CMR1 and has previously been identified as a prostate-specific transcript and has also been found to be expressed in various tumor tissue, including prostate, melanoma, colorectal and breast carcinoma (Tsavaler, L., et al. Cancer Res. 61:3760-3769, 2002). Mouse CMR1 (also known as mouse TRPM8) was cloned from a mouse DRG cDNA preparation and was shown to be 93% identical to the human CMR1 amino acid sequence (Peier, A. M. et al., Cell 108:705-715, 2002).

In the present invention, the canine cCMR1 gene was cloned from a cDNA library prepared from canine DRG tissue. The cCMR1 cDNA was sequenced, including the cCMR1 open reading frame (ORF) and 5' and 3' untranslated regions of the corresponding mRNA. The cCMR1 cDNA sequence is shown as SEQ ID NO: 1 (Table 1). SEQ ID NO: 1 encodes a 1104 residue polypeptide (SEQ ID NO: 2), also shown in Table 1, which is aligned with the CMR1 protein sequences from human, mouse, and rat (see Table 2). Based on this alignment, the cCMR1 polypeptide shares the greatest amino acid identity with the human CMR1 at 95.23%.

In the present invention, the cCMR1 nucleic acid was also subcloned into an expression vector and transformed into a host cell for expression of the cCMR1 protein. This recombinant cCMR1 cell system was shown to express a functional cCMR1 protein that allowed influx of $Ca^{++}$ ions when the recombinant cCMR1 cells were incubated at low temperatures or exposed to menthol or icilin. The recombinant cCMR1 system is useful for screening and for identifying compounds that modulate cCMR1 function or expression. Compounds that modulate CMR1 function or expression can be therapeutically useful. These compounds can be identified using, for example, a recombinant system expressing the cCMR1 protein and then tested in vivo in dogs or any other suitable mammals, to establish dosing parameters that can be useful in humans.

Modulation of the function or expression of CMR1 proteins can be advantageous for the treatment of various painful conditions. Since the CMR1 receptor is responsive to cold and compounds, such as menthol and icilin, that mimic a cold-like sensation, it is anticipated that modulation of cCMR1 activity is also relevant for therapeutic applications where cold or menthol treatment is used as a method of pain relief or other relief, such as congestive rhinitis, cough or asthmatic bronchitis. For example, modulation of function or expression of CMR1 proteins can be useful for patients having dermal or mucus membrane conditions, such as skin inflammation and dermal burns, including sunburn and razor burn, or sore throat. Modulation of CMR1 activity can also be relevant in patients suffering from hypersensitivity to cold that causes cold allodynia. Modulation of CMR1 activity can also be relevant for treating acute pain, for example, toothache (odontalgia) and other trigeminally distributed pains, such as trigeminal neuralgia (tic douleureux) and temperomandibular joint pain.

In addition, since human CMR1 has been identified as a marker that is associated with tumor growth (Tsavaler, L., et al. Cancer Res. 61:3760-3769, 2002), cCMR1 can also be useful for the diagnosis of various cellular proliferation disorders in dogs.

In attempts to clone the cCMR1 homologue, a PCR-based strategy was employed. Oligonucleotide primers were synthesized according to the sequences set forth in SEQ ID NO: 3 (cmr1-23) and SEQ ID NO: 4 (cmr1-26). These primers were able to successfully amplify a portion of the cCMR1 sequence from position 1761 to position 2886 of SEQ ID NO: 1. The PCR product, which was approximately 1.1 kb in size, was purified and then subcloned into a sequencing vector. Based on the sequence of the 1.1 kb cCMR1 fragment, new primers were developed and used in separate PCR reactions with RACE (rapid amplification of cDNA ends)-modified canine DRG cDNA. The complete sequence of the cCMR1 cDNA, including both 5' and 3' untranslated regions, was obtained (SEQ ID NO: 1). The open reading frame of cCMR1 encodes a 1104 residue polypeptide (SEQ ID NO: 2), as shown in Tables 1.

Therefore, in one embodiment, the invention provides an isolated nucleic acid sequence comprising a sequence from position 69 to 3380 of SEQ ID NO: 1. Position 69 to 3380 of SEQ ID NO 1 is an open-reading frame sequence (coding region), which can encode a CMR1 polypeptide according to SEQ ID NO: 2. The invention also provides isolated nucleic acids sequences corresponding to the region upstream from the cCMR1 open-reading frame, for example, from position 1 to 69 of SEQ ID NO: 1 and isolated nucleic acid sequences corresponding to the region downstream from the cCMR1 open-reading frame, for example, from position 3380 to 3815 of SEQ ID NO: 1. Therefore, in another embodiment, the invention provides an isolated nucleic acid sequence that includes a sequence from position 1 to 69 of SEQ ID NO: 1, and in another embodiment from position 3380 to 3815 of SEQ ID NO: 1.

Isolated nucleic acids comprising fragments of SEQ ID NO: 1 are useful for a variety of purposes. For example, these sequences can be used as oligonucleotide probes for the detection of CMR1 nucleic acids or for the detection of sequences that flank CMR1 nucleic acids. They can be used as oligonucleotide primers for the amplification of CMR1 nucleic acids. They can also be used for the preparation of chimeric nucleic acids that encode a portion or all of the cCMR1 polypeptide fused to another polypeptide sequence, for example, one or more motifs or domains of the cCMR1 sequence recombined with one or more motifs or domains from one or more heterologous sequences. Further, they can be used for manipulating the structure of the cCMR1 gene.

In yet another embodiment, the invention provides an isolated nucleic acid comprising a nucleic acid sequence that encodes a polypeptide comprising SEQ ID NO: 2. Due to the degeneracy of the genetic code, more than one codon may be used to encode a particular amino acid, and therefore, a cCMR1 amino acid sequence (for example, SEQ ID NO: 2) can be encoded by any one of a plurality of nucleic acid sequences. Isolated nucleic acid includes sequences wherein one or more codons in the sequence are replaced by codons of a different sequence but that code for the same amino acid residue are herein referred to as "conservative codon substitutions". Therefore, the invention encompasses nucleic acid sequences encoding SEQ ID NO: 2 that have one or more than one conservative codon substitution. One of skill in the art would be able to determine a particular nucleic acid sequence having one or more than one conservative codon substitution and encoding SEQ ID NO: 2, based on the sequence information provided herein. Conservative codon substitutions can be made in the nucleic acid sequence encoding the CMR1 polypeptide, for example, the codons TTT and TTC (collectively referred to as TTT/C) can encode a Phe (phenylalanine) residue; other codon substitutions are as follows: TTA/G and CTT/C/A/G: Leu; ATT/C: Ile; ATG: Met; GTT/C/A/G: Val; TCT/C/A/G: Ser; CCT/C/A/G: Pro; ACT/C/A/G: Thr; GCT/C/A/G: Ala; TAT/C: Tyr; CAT/C: His; CAA/G: Gln; AAT/C: Asn; AAA/G: Lys; GAT/C: Asp; GAA/G Glu; TGT/C: Cys; CGT/C/A/G: Arg; AGT/C: Ser; AGA/G; Arg; GGT/C/A/G:Gly. Conservative codon substitutions can be made at any position in the nucleic acid sequence that encodes the cCMR1 polypeptide.

As shown herein, position 69 to position 3380 of SEQ ID NO: 1 encodes a 1104 amino acid residue polypeptide (SEQ ID NO: 2), which is the predicted sequence of the canine CMR1 as naturally expressed. As shown in Table 2, SEQ ID NO: 2 was aligned to the human, mouse and rat CMR1 protein sequences. By alignment, cCMR1 polypeptide sequence (SEQ ID NO: 2) is most identical to the human CMR1 protein sequence, sharing 1052 out of 1104 residues (95.23% identity). The cCMR1 protein sequence shares a lower degree of identity with the mouse (1042/1104: 94.38% identity) and rat (1043/1104: 94.47% identity) CMR1 polypeptide sequences.

As indicated, the dog, human, mouse and rat CMR1 sequences, as shown in Table 2, generally share greater than 90% amino acid identity. However, at certain amino acid positions, the canine sequence differs from one or more of the human, mouse or rat sequences. The amino acid positions wherein the canine residue differs from one or more than one other species are more variable as compared to positions wherein the residue is identical in the human, dog, mouse and rat sequences. For example, based on the sequence alignment, the amino acid residues at positions 1, 2 and 3 of SEQ ID NO: 2 are identical to those of the human, mouse and rat sequence. However, the amino acid residues at position 4 and 5 of SEQ ID NO: 2 vary with regard to the human sequence, and the amino acid residue at position 28 of SEQ ID NO: 2 varies with regard to human, mouse and rat sequences. Amino acid positions wherein there is at least one difference between the canine sequence and any one of the human, mouse or rat CMR1 sequences are herein referred to as "CMR-family variant positions". A list of CMR-family variant positions is provided in Table 3.

Based on this analysis, a cCMR1 polypeptide having a substitution of one or more CMR-family variant amino acids is anticipated to have CMR1 biological activity. That is, SEQ ID NO: 2 can be substituted at one or more CMR-family variant amino acid positions with an amino acid selected from amino acid residues found in the human, mouse, or rat sequences, or an equivalent amino acid, at that same position. The amino acid that replaces a cCMR1 amino acid is herein referred to as a "CMR-family variant amino acid". A "CMR-family variant amino acid" consists of an amino acid that differs from the cCMR1 amino acid and that is the amino acid present in the CMR1 sequence of other mammals, such as human, mouse or rat. A list of suitable CMR-family variant amino acids, any of which can be use to replace an original cCMR1 amino acid residue can also be found in Table 3. For example, a CMR-family variant amino acid at position 4 suitable for the replacement of the glutamic acid (E) of SEQ ID NO: 2, is arginine (R, as occurs in human CMR1).

At some CMR-family variant amino acid positions, the canine, human, mouse and rat amino acid residues share a common chemical property. For example, CMR-family variant amino acids at positions 18 and 34 of SEQ ID NO: 2 can include a hydrophobic amino acid residue, for example, methionine (M) or leucine (L). Other hydrophobic amino acids include glycine, valine, isoleucine and proline. Other amino acid groups include "basic amino acids," which include histidine, lysine, and arginine; "acidic amino acids," which include glutamic acid and aspartic acid; "aromatic amino acids," which include phenylalanine, tryptophan, and tyrosine; "small amino acids," which include glycine and alanine; "nucleophilic amino acids," which include serine, threonine, and cysteine; and "amide amino acids," which include aparagine and glutamine.

Therefore, in another aspect, the invention provides a nucleic acid encoding a CMR1 polypeptide according to SEQ ID NO: 2 that includes a CMR-family variant amino acid. In some embodiments, cCMR1 polypeptides include CMR-family variant amino acids in less than 4% of the original cCMR1 amino acid residues. Preferably the cCMR1 polypeptides include CMR-family variants in less than about 2% of the original cCMR1 amino acid residues, and most preferably less than about 1% of the original cCMR1 amino acid residues.

The invention also provides isolated nucleic acid molecules that are complementary to any isolated nucleic acid molecules, as described herein.

The isolated nucleic acid of the invention can also include nucleic acid sequences that encode the cCMR1 polypeptide having additional amino acid residues. In some embodiments, the additional amino acids are present at the amino terminus, the carboxyl terminus, within the cCMR1 sequence or combinations of these locations. cCMR1 polypeptides having these types of additional amino acid sequences can be referred to as "cCMR1 fusion proteins". In some cases, it may be more appropriate to refer to them otherwise as "chimeric" or "tagged" cCMR1 proteins, or the like, depending on the nature of the additional amino acid sequences. Nonetheless, one will be able to discern a CMR1 polypeptide having additional amino acid sequences given the sequence information provided herein. The additional amino acid residues can be short, for example, from one to about 20 additional amino acid residues, or longer, for example, greater than about 20 additional amino acid residues. The additional amino acid residues can serve one or more functions or purposes including, for example, serving as epitopes for protein (e.g., antibody) or small molecule binding; serving as tags for intracellular and extracellular trafficking; providing additional enzymatic or other activity; or providing a detectable signal.

For example, a nucleic acid sequence can encode a cCMR1 fusion protein, which can include additional amino acid residues providing coordinates for bonding (such as ionic, covalent, coordinative, hydrogen or Van der Waals bonding or combinations thereof with organic or inorganic compounds. Useful additional amino acid sequences include, for example, poly-histidine residues useful for protein purification via $Ni^{+}$-coupled residue, constant domains of immunoglobulins (IgA, IgE, IgG, IgM) or portions thereof (CH1, CH2, CH3), albumin, hemagluttinin (HA) or myc affinity epitope tags useful for the formation of immuno-complexes for detection or purification (antibodies against these moieties can be obtained commercially), polypeptides useful for detection such as the green fluorescent protein (GFP), enzymes such as beta-galactosidase (B-Gal) chloramphenicol acetyltransferase (CAT), luciferase, and alkaline phosphatase (A), signal sequences for protein trafficking and protease cleavage sequences useful for separating additional amino acid sequences from the cCMR1 sequence, if desired.

In another aspect, diagnostic assays are provided which are capable of detecting the expression of cCMR1, such as cCMR1 protein or nucleic acid. Expression of the cCMR1 proteins can be detected by a probe, which is detectably labeled or which can be subsequently labeled. Typically, the probe is an antibody that recognizes the expressed protein, as described above, especially a monoclonal antibody. Accordingly, in one embodiment, an assay capable of detecting the expression of cCMR1 protein comprises contacting a canine tissue sample with one or more than one monoclonal and/or polyclonal antibody that binds to cCMR1.

cCMR1 nucleic acids and proteins, antibodies directed against CMR1 and biological systems containing any of these components can be labeled with a detectable reagent, or a compound having specificity for cCMR1 can be labeled with a detectable reagent and used to detect the cCMR1 entity. Detectable reagents include compounds and compositions that can be detected by spectroscopic, biochemical, photochemical, bioelectronic, immunochemical, electrical, optical or chemical techniques. Examples of detectable moieties include, but are not limited to, radioisotopes (e.g., $^{32}P$ $^{33}P$, $^{35}S$), chemiluminescent compounds, labeled binding proteins, heavy metal atoms, spectroscopic markers, such as fluorescent markers and dyes, linked enzymes, mass spectrometry tags and magnetic labels.

Immunoassay methods that utilize antibodies include, but are not limited to, dot blotting, Western blotting, competitive and non-competitive protein binding assays, enzyme-linked immunosorbant assays (ELISA), immunohistochemistry, fluorescence-activated cell sorting (FACS), immuno-PCR, immunoprecipitation and others commonly used.

The level of expression of mRNA corresponding to the cCMR1 gene can be detected utilizing commonly used molecular biological methods, for example, Northern blotting, in situ hybridization, nuclease protection assays, RT-PCR (including real-time, quantitative PCR), high density arrays and other hybridization methods. Accordingly, in another embodiment, an assay capable of detecting the expression of one or more than one cCMR1 gene in a sample of canine tissue is provided, which comprises contacting a canine tissue sample with an oligonucleotide capable of hybridizing to a cCMR1 nucleic acid. The oligonucleotide primer is generally from 10-20 nucleotides in length for PCR/primer extension experiments. Longer oligonucleotides of approximately 40-50 nucleotides are more regularly utilized for in situ or blot hybridizations. Sequences even longer than 50 nucleotides can also be employed for the detection experiment. RNA can be isolated from the tissue sample by methods well-known to those skilled in the art as described, for example, in Ausubel et al., Current Protocols in Molecular Biology, John Wiley and Sons, Inc. (1996). One preferred method for detecting the level of mRNA transcribed from the cCMR1 genes is by RT-PCR. Details of RT-PCR techniques are well known and also described herein.

Another preferred method for detecting the level of mRNA transcripts obtained from more than one of the disclosed genes involves hybridization of labeled mRNA to an ordered array of oligonucleotides or tissue. Such a method allows the level of transcription of a plurality of these genes to be determined simultaneously to generate gene expression profiles or patterns.

The oligonucleotides utilized in this hybridization method typically are bound to a solid support. Examples of solid supports include, but are not limited to, membranes, filters, slides, paper, nylon, wafers, fibers, magnetic or nonmagnetic beads, gels, tubing, polymers, polyvinyl chloride dishes, etc. Any solid surface to which the oligonucleotides can be bound, either directly or indirectly, either covalently or noncovalently, can be used. A particularly preferred solid substrate is a high-density array or DNA chip. These high-density arrays contain a particular oligonucleotide probe in a preselected location on the array. Each pre-selected location can contain more than one molecule of the particular probe. Because the oligonucleotides are at specified locations on the substrate, the hybridization patterns and intensities (which together result in a unique expression profile or pattern) can be interpreted in terms of expression levels of particular genes.

The oligonucleotide probes are preferably of sufficient length to specifically hybridize only to complementary transcripts of the above identified gene(s) of interest.

Optionally, all or a portion of the cCMR1 nucleic acid sequence can be used to probe nucleic acid preparations from other species to determine the presence of similar sequences. For example, all or a portion of the cCMR1 nucleic acid can be used as a probed to identify cDNA or genomic nucleic acid sequences from other species that are similar to the cCMR1 sequence. Positive clones can be identified as those that hybridize to the cCMR1 probe.

In addition, all or a portion of the cCMR1 nucleic acid or polypeptide sequence as provided by the invention can be used in computer-aided programs to identify other useful information, for example, proteins having homology to the cCMR1 sequence or molecules that bind to the cCMR1 sequence. For example, all or portions of the cCMR1 sequence can be used to screen various electronic databases to determine whether a member of the electronic database has homology to the cCMR1 sequence. Numerous genetic databases that are species-specific can be queried using any portion of the canine nucleic acid or polypeptide sequences as set forth herein. Either or both nucleic acid and protein searches can be performed.

In another aspect, a three-dimensional model of the cCMR1 polypeptide can be determined and used to identify molecules that bind to various portions of the protein structure. For example, using an isolated cCMR1 nucleic acid as described herein, the cCMR1 protein can be expressed in a cell system, purified and then crystallized in order to obtain information regarding the structure of the protein. Structural information can be obtained by performing, for example, X-ray diffraction or nuclear magnetic resonance spectroscopy. The location of amino acid residues and their side chains can be expressed as coordinates in a three-dimensional model. This information can then be provided to a computer program.

Molecular modeling programs can be used to determine whether a small molecule can fit into a functionally relevant portion, for example, an active site, of the cCMR1 polypeptide. Basic information on molecular modeling is provided in, for example, M. Schlecht, Molecular Modeling on the PC, 1998, John Wiley & Sons; Gans et al., Fundamental Principals of Molecular Modeling, 1996, Plenum Pub. Corp.; N. C. Cohen (editor), Guidebook on Molecular Modeling in Drug Design, 1996, Academic Press; and W. B. Smith, Introduction to Theoretical Organic Chemistry and Molecular Modeling, 1996. U.S. patents that provide detailed information on molecular modeling include U.S. Pat. Nos. 6,093,573; 6,080,576; 5,612,894; and 5,583,973.

Programs that can be useful for molecular modeling studies include, for example, GRID (Goodford, P. J., "A Computational Procedure for Determining Energetically Favorable Binding Sites on Biologically Important Macromolecules" J. Med. Chem., 28, pp. 849-857, 1985), available from Oxford University, Oxford, UK; MCSS (Miranker, A. and M. Karplus, "Functionality Maps of Binding Sites: A Multiple Copy Simultaneous Search Method." Proteins: Structure, Function and Genetics, 11, pp. 29-34, 1991), available from Molecular Simulations, Burlington, Mass.; AUTODOCK (Goodsell, D. S. and A. J. Olsen, "Automated Docking of Substrates to Proteins by Simulated Annealing" Proteins: Structure. Function, and Genetics, 8, pp. 195-202, 1990); available from Scripps Research Institute, La Jolla, Calif.; and DOCK (Kuntz, I. D. et al., "A Geometric Approach to Macromolecule-Ligand Interactions" J. Mol. Biol., 161, pp. 269-288, 1982), available from University of California, San Francisco, Calif.

In addition to nucleic acid sequences encoding cCMR1 polypeptides, the invention also includes cCMR1 polypeptides, cCMR1 polypeptide variants, fragments of cCMR1 polypeptides and cCMR1 polypeptides having additional amino acids. Aspects of cCMR1 polypeptides encoded by nucleic acids are described herein, and these aspects can also apply to cCMR1 polypeptides.

In one embodiment, the invention provides an isolated polypeptide that includes the sequence of SEQ ID NO: 2.

In another embodiment, the invention provides an isolated polypeptide that includes the sequence of SEQ ID NO: 2 having CMR-family variant amino acids in less than 4% of the original cCMR1 amino acid residues. Preferably the cCMR1 polypeptides include CMR-family variants in less than about 2% of the original cCMR1 amino acid residues, and most preferably less than about 1% of the original cCMR1 amino acid residues.

As described herein, the cCMR1 polypeptide can also have additional amino acid residues at its amino terminus, its carboxyl terminus or both. Such additional residues are useful for a variety or purposes, including, for example, immunodetection, purification, cellular trafficking, enzymatic activity, etc.

The invention also provides fragments of the cCMR1 polypeptide. Fragments of the cCMR1 polypeptide can be useful for a number of purposes including, for example, antibody production. Portions of the cCMR1 polypeptide sequence, or the entire sequence itself, can be used to generate anti-CMR1 antibodies.

In another aspect, the present invention relates to antibodies that specifically recognize epitopes within the amino acid sequence of SEQ ID NO: 2. Useful antibodies include, but are not limited to, polyclonal antibodies, monoclonal antibodies, humanized or chimeric antibodies, and biologically functional antibody fragments that are able to bind to a portion of the cCMR1 protein. Antibodies specific for proteins encoded by the aforementioned sequences have utilities in several types of applications. These antibodies can be used in diagnostic kits, for example, for any sort of assay wherein detection of cCMR1 is desired. They can also be used in the preparation of therapeutic agents, for example, wherein the anti-cCMR1 antibody itself is therapeutic or wherein the anti-cCMR1 antibody is coupled to a therapeutic agent. It is anticipated that anti-cCMR1 antibodies could be used for treating pain. In these cases an anti-cCMR1 antibody could modulate the activity of cCMR1, for example, providing either an agonistic (e.g., catalytic) or antagonistic activity.

The invention also provides methods for the production of canine-specific monoclonal anti-CMR1 antibodies. For the production of these monoclonal antibodies, peptides that provide unique anti-cCMR1 determinants can be used. Monoclonal antibodies are homogeneous clonal populations of antibodies that are directed to a specific antigen (i.e., epitope). To prepare anti-cCMR1 monoclonal antibodies, a peptide having cCMR1-specific sequence or a "cCMR1 epitope" is used. A cCMR1 sequence is one that is different at one or more positions relative to the dog, mouse and rat CMR1 sequences. In order to determine a cCMR1 specific sequence, one can refer to Table 2 provided herein.

Monoclonal antibodies (mAbs) can be obtained by any technique that provides for the production of antibody molecules by continuous cell lines in culture. These include, for example, the hybridoma technique (Kohler and Milstein, Nature, 256:495-497, 1975); the human B-cell hybridoma technique (Kosbor et al., Immunology Today, 4:72, 1983); and the EBV-hybridoma technique (Cole et al., Monoclonal Antibodies and Cancer Therapy, Alan R. Liss, Inc., pp. 77-96, 1985). Such antibodies may be of any immunoglobulin class including IgG, IgM, IgE, IgA, IgD or any subclass thereof. The hybridoma producing the mAb of this invention may be cultivated in vitro or in vivo.

For the production of antibodies to the CMR1 protein, various host animals can be immunized by injection with the cCMR1 polypeptide, or a portion thereof. If the entire cCMR1 polypeptide is used, antibodies specific to cCMR1 along with anti-CMR antibodies that are cross-reactive with other CMR1 proteins from different species may be generated. For example, polyclonal antibody preparations are a heterogeneous population of antibody molecules derived from the sera of animals immunized with an antigen, such as the CMR1 polypeptide. In this polyclonal population, antibodies will be cross-reactive with different portions of the CMR1 polypeptide, with some of those antibodies being specifically reactive with cCMR1 and others being cross-reactive with CMR1 polypeptides of other species. For the production of polyclonal antibodies, host animals are immunized with the cCMR1 protein, or a portion thereof, typically repeatedly to boost antibody titer in the animal and typically supplemented with adjuvants as described herein. Commonly used host animals for the production of anti-CMR1 antibodies include rabbits, mice and rats; however, other animals can be used if desired. Various adjuvants may be used to increase the immunological response, depending on the host species, for example, Freund's (complete and incomplete) adjuvant and mineral gels such as aluminum hydroxide. Conjugates (e.g., KLH) can also be included for the immunization, especially in cases where shorter cCMR1 peptides are used for the purposes of immunization and antibody production.

cCMR1 polypeptides or cCMR1 polypeptide fragments can be generated using any sort of synthetic or molecular biological technique. Standard synthetic peptide techniques can be used to generate smaller cCMR1 polypeptide fragments, for example peptide fragments that are 30 amino acids in length or shorter. Techniques for the synthesis of peptides fragments are well known and are described in, for example, Barany and Merrifield, Solid-Phase *Peptide Synthesis*; pp. 3-284 in The Peptides: Analysis, Synthesis, Biology. Vol. 2: Special Methods in *Peptide Synthesis*, Part A., Merrifield, et al., J. Am. Chem. Soc., 85: 2149-2156 (1963), and Stewart et al., Solid Phase *Peptide Synthesis*, 2nd ed. Pierce Chem. Co., Rockford, Ill. (1984).

Recombinant techniques can be used for the expression of cCMR1, including, for example, portions of cCMR1, variants and fusions from prokaryotic or eukaryotic host cells transformed with a cCMR1 nucleic acid. These methods include, for example, in vitro recombinant DNA techniques and in vivo genetic recombination (see, for example, the techniques described in Sambrook et al., Molecular Cloning, A Laboratory Manual, 3'd Edition, Cold Spring Harbor Press, NY (2001); and Ausubel et al., eds., Short Protocols in Molecular Biology, 4th Edition, John Wiley & Sons, Inc., NY (1999)).

Therefore, cCMR1 can be produced by (a) providing a nucleic acid comprising a cCMR1 sequence, (b) inserting the nucleic acid into a host cell and (c) maintaining the host cell under conditions that allow for the expression of the cCMR1 polypeptide. When a purified cCMR1 polypeptide is desired, a step can also be performed to isolate and, if desired, purify the cCMR1 polypeptide.

In another embodiment, the invention provides a heterologous nucleic acid construct that includes the entire or a portion of the cCMR1 coding sequence operably linked to a regulatory sequence. These heterologous nucleic acid constructs include recombinant expression vectors suitable for expression of the cCMR1 nucleic acid in a host cell. Recombinant expression vectors include one or more regulatory sequences, which can be selected based on the type of host cells used for cCMR1 expression, operably linked to the cCMR1 nucleic acid sequence. Regulatory sequences include promoters, enhancers and other expression control elements, for example, poly (A)+ sequences. Regulatory sequences can be specific for prokaryotic cells, for example, bacterial cells, such as *E. coli*, or for eukaryotic cells, such as yeast cells, insect cells or mammalian cells (for example, HEK, CHO or COS cells). Regulatory sequences can be located cis or trans relative to the cCMR1 nucleic acid sequence. Regulatory sequences can include constitutive expression sequences that typically drive expression of the nucleic acid under a wide variety of growth conditions and in a wide variety of host cells, tissue-specific regulatory sequences that drive expression in particular host cells or tissues and inducible regulatory sequences that drive expression in response to a secondary factor. Choice and design of the expression vector can depend on such factors as the particular host cell utilized and the desired levels of polypeptide expression. Other expression vector components can include, but are not limited to, one or more of the following: a signal sequence, an origin of replication, one or more selection genes and a transcription termination sequence. Selection genes encode proteins that (a) confer resistance to antibiotics or other toxins, for example, ampicillin, neomycin, methotrexate or tetracycline, (b) complement auxotrophic deficiencies or (c) supply critical nutrients not available from complex media.

Heterologous nucleic acid constructs used for expression of the cCMR1 polypeptide can also include constructs that can be transcribed and translated in vitro, for example, constructs having a T7 promoter regulatory sequence.

Vectors suitable for the expression of cCMR1 are known in the art and commercially available. Suitable vectors include, for example, pET-14b, pCDNAIAmp and pVL1392, which are available from Novagen and Invitrogen and can be used for expression in *E. Coli*, COS cells and baculovirus infected insect cells, respectively.

In another embodiment, the invention provides a recombinant cell that includes a cCMR1 nucleic acid. Recombinant cells include those wherein a nucleic acid sequence has been introduced. Typically, recombinant cells are created by introducing a particular nucleic acid into cells using molecular biological techniques. However, recombinant cells also include cells that have been manipulated in other ways to promote the expression of a desired nucleic acid sequence. For example, regions that are proximal to a target nucleic acid sequence can be altered to promote expression of the target nucleic acid, or genes that act to regulate the expression of a target nucleic acid can be introduced into a cell.

Recombinant cells, after periods of growth and division, may not be identical to the starting parent cell; however, these cells are still referred to as recombinant cells and are included within the scope of the term as used herein.

Host cells suitable for harboring and providing the machinery for cCMR1 expression include both prokaryotic and eukaryotic cells. Examples of suitable prokaryotic host cells are eubacteria, such as Gram-negative or Gram-positive organisms, for example, Enterobacteriaceae such as *Escherichia*, for example, *E. coli, Enterobacter, Salmonella*, for example, *Salmonella typhimurium*, as well as *Bacilli* such as *B. subtilis, Pseudomonas*, and *Streptomyces*.

Eukaryotic cells, such as filamentous fungi or yeast, are suitable cloning or expression hosts for cCMR1 expression vectors. *Saccharomyces cerevisiae*, also known as baker's yeast, is a commonly used expression system and offers a variety of promoter and selectable marker sequences. Other fungi or yeast useful as host cells include *Schizosaccharomyces pombe, Kluyveromyces lactis, Pichia pastoris, Candida, Neurospora crassa* and *Aspergillus nidulans*.

Many higher eukaryotic host cells can be used, including insect cells, such as *Drosophila* S2 and *Spodoptera* Sf9 cells, mammalian cells, such as Chinese Hampster Ovary (CHO) cells, monkey kidney (COS) cells, canine kidney (MDCK) cells, human cervical carcinoma (HeLa) cells, and human embryonic kidney (HEK) cells as well as plant cells.

Growth of the transformed host cells can occur under conditions that are known in the art. The conditions will generally depend upon the host cell and the type of vector used. Suitable induction conditions, such as temperature and chemicals, may be used and will depend on the type of promoter utilized. Examples of suitable media include Minimal Essential Medium ((MEM), RPMI-1640 and Dulbecco's Modified Eagle's Medium (DMEM).

Nucleic acids, including expression constructs, can be introduced into prokaryotic or eukaryotic cells via conventional transformation or transfection techniques. As used herein, the terms "transformation" and "transfection" are intended to refer to a variety of art-recognized techniques for introducing a foreign nucleic acid molecule (e.g., DNA) into a host cell, including calcium phosphate or calcium chloride co-precipitation, DEAE-dextran-mediated transfection, lipofection, biolistics or electroporation. Suitable methods for transforming or transfecting host cells can be found in Sambrook, et al. (supra), and other laboratory manuals.

Mammalian cells can be stably transfected with an expression construct having a selectable marker and with the gene of interest. Typically selectable markers for mammalian cells include antibiotic-resistance genes, for example, genes that allow the transformed cell to grow in the presence of compounds such as G418, hygromycin or methotrexate.

Recombinant cells can be useful for the production of a cCMR1 polypeptide for purification purposes or for functional studies involving the cCMR1 polypeptide. For example, a recombinant cCMR1 cell can be used to test a number of compounds for their ability to alter the activity of the cCMR1 polypeptide. The recombinant cCMR1 cell can also be used to test how altering various properties of the cCMR1 polypeptide, for example, altering the amino acid sequence of the cCMR1 polypeptide, affects cCMR1 activity.

Recombinant cells having a cCMR1 nucleic acid sequence can also be used to produce non-human transgenic animals. A transgene is exogenous DNA which is integrated into the genome of a cell from which a transgenic animal develops and which remains in the genome of the mature animal, thereby directing the expression of an encoded gene product in one or more cell types or tissues of the transgenic animal. For example, a nucleic acid containing a cCMR1 nucleic acid sequence can be introduced into a host cell such as a fertilized oocyte or an embryonic stem cell, using a suitable technique, such as microinjection. These cCMR1-containing host cells can then be used to create non-human transgenic animals. Particularly useful animals include transgenic mice or rats having a cCMR1 gene, which can also have physical or genetic characteristics making them useful for study as, for example, a pain model.

cCMR1 transgenic animals can be used to identify, screen or test potentially useful compounds, or known compounds that modulate cCMR1 function or expression. These transgenic animals can also be used to study the function of the cCMR1 polypeptide by altering its amino acid sequence.

Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, Manipulating the Mouse Embryo (Cold Spring Harbor Laboratory Press, Cold Spring Harbor, N.Y., 1986). Methods for constructing homologous recombination vectors and homologous recombinant animals are described further in Bradley (Current Opinion in Bio/Technology, 2:823-829, 1991) and in PCT Publication Nos. WO 90/11354, WO 91/01140, WO 92/0968, and WO 93/04169. Clones of the non-human transgenic animals described herein can also be produced according to the methods described in Wilmut et al. (Nature, 385:810-813, 1997) and PCT Publication Nos. WO 97/07668 and WO 97/07669.

In some cases, it can be desirable to reduce the amount of CMR1 present in a system, for example, in order to test the specificity of compounds that are suspected of being CMR1 modulators. The recombinant cells or transgenic animals, as described herein, can be manipulated in order to reduce the amount of CMR1 expressed or present on its surface. For example, the cell can include molecules that reduce the amount of cCMR1 RNA present in the cell, thereby reducing cCMR1 protein expression. Suitable molecules include antisense nucleotides, ribozymes, double-stranded RNAs, interfering RNA (iRNA) and antagonists or agonists.

A variety of methods can be used for purification of the cCMR1 polypeptide. For example, crude purification can be performed using ammonium sulfate precipitation, centrifugation or other known techniques. A higher degree of purification can be achieved by suitable chromatographic techniques, including, for example, anion exchange, cation exchange, high performance liquid chromatography (HPLC), gel filtration, hydrophobic interaction chromatography and affinity chromatography, for example, immunoaffinity chromatography using antibodies directed against the cCMR1 protein. If needed, steps for refolding the cCMR1 proteins may be used to obtain the active conformation of the protein when the protein is denatured during intracellular synthesis, isolation or purification.

The invention also encompasses kits for detecting the presence of a polypeptide or nucleic acid of the invention in a biological sample (a test sample). Such a kit preferably comprises a compartmentalized carrier suitable to hold in close confinement at least one container. The carrier can contain a means for detection such as labeled antigen or enzyme substrates or the like. For example, the kit can comprise a labeled compound or agent capable of detecting the polypeptide or mRNA encoding the polypeptide and means for determining the amount of the polypeptide or mRNA in a sample (e.g., an antibody which binds the polypeptide or an oligonucleotide probe which binds to DNA or mRNA encoding the polypeptide). The kits can also include instructions for determining whether a test subject is suffering from or is at risk of developing a disorder associated with aberrant expression of the polypeptide if the amount of the polypeptide or mRNA encoding the polypeptide is above or below a normal level.

For antibody-based kits, the kit can comprise, for example: (1) a first antibody (for example, an antibody attached to a solid support), which binds selectively to a polypeptide comprising an amino acid sequence having at least 96% sequence identity to SEQ ID NO: 2; and, optionally; (2) a second antibody which binds to either the first antibody or the polypeptide that the first antibody binds to, but at a different epitope, and which is conjugated to a detectable agent; and (3) a purified recombinant cCMR1 protein as a positive control. Preferably, the first antibody only binds to a cCMR1, but not a CMR1 from other species, such as human, rat, or mouse.

For oligonucleotide-based kits, the kit can comprise, for example: (1) an oligonucleotide, e.g., a detectably labeled oligonucleotide, which hybridizes under stringent condition to SEQ ID NO: 1, or (2) a pair of primers useful for amplifying a nucleic acid molecule encoding a polypeptide having at least 96% sequence identity to SEQ ID NO: 2. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample. Each component of the kit is usually enclosed within an individual container and all of the various containers are preferably contained within a single package.

Because CMR1 is activated at cool to cold temperatures and is expressed in nerve tissue, this gene can serve as a therapeutic target for the identification of drugs useful in treating pain, inflammation and skin disorders, for example, those associated with sunburn and other sensitized states. Therefore, in another general aspect, the present invention relates to the use of cCMR1 nucleic acids and proteins in methods for identifying therapeutic compounds, for example, compounds useful in treating pain, modulating responses to cold temperature and compounds that provide a cool sensation to the skin. These types of compounds can be identified using a system that includes a cCMR1 polypeptide or a cCMR1 nucleic acid. Compounds can also be tested directly in vivo in an animal model system, for example, a rat, mouse or canine model system. Particularly useful systems include animal models of pain. These methods comprise assaying for the ability of various compounds to increase or decrease the expression of the cCMR1 protein, the conductivity of the cCMR1 channel or the nociceptive behaviors of an animal.

The compound identification methods can be performed using conventional laboratory formats or in assays adapted for high throughput. The term "high throughput" refers to an assay design that allows easy screening of multiple samples simultaneously and/or in rapid succession, and can include the capacity for robotic manipulation. Another desired feature of high throughput assays is an assay design that is optimized to reduce reagent usage, or minimize the number of manipulations in order to achieve the analysis desired. Examples of assay formats include 96-well or 384-well plates, levitating droplets, and "lab on a chip" microchannel chips used for liquid handling experiments. It is well known by those in the art that as miniaturization of plastic molds and liquid handling devices are advanced, or as improved assay devices are designed, greater numbers of samples can be processed using the design of the present invention.

Candidate compounds encompass numerous chemical classes, including but not limited to, small organic or inorganic compounds, natural or synthetic molecules, such as antibodies, proteins or fragments thereof, antisense nucleotides, interfering RNA (iRNA) and ribozymes. Preferably, they are small organic compounds, i.e., those having a molecular weight of more than 50 yet less than about 2500. Candidate compounds comprise functional chemical groups necessary for structural interactions with polypeptides, and typically include at least an amine, carbonyl, hydroxyl or carboxyl group, preferably at least two of the functional chemical groups and more preferably at least three of the functional chemical groups. The candidate compounds can comprise cyclic carbon or heterocyclic structure and/or aromatic or polyaromatic structures substituted with one or more of the above-identified functional groups. Candidate compounds also can be biomolecules such as peptides, saccharides, fatty acids, sterols, isoprenoids, purines, pyrimidines, derivatives or structural analogs of the above, or combinations thereof and the like. Where the compound is a nucleic acid, the compound typically is a DNA or RNA molecule, although modified nucleic acids having non-natural bonds or subunits are also contemplated.

Candidate compounds are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Candidate compounds can also be obtained using any of the numerous approaches in combinatorial library methods known in the art, including biological libraries; spatially addressable parallel solid phase or solution phase libraries: synthetic library methods requiring deconvolution; the "one-bead one-compound" library method; and synthetic library methods using affinity chromatography selection (Lam (1997) *Anticancer Drug Des.* 12:145). Alternatively, libraries of natural compounds in the form of bacterial, fungal, plant and animal extracts are available or readily produced. Additionally, natural and synthetically produced libraries and compounds can be readily modified through conventional chemical, physical, and biochemical means.

Further, known pharmacological agents can be subjected to directed or random chemical modifications such as acylation, alkylation, esterification, amidation, etc. to produce structural analogs of the agents. Candidate compounds can be selected randomly or can be based on existing compounds that bind to and/or modulate the function of CMR1 activity. Therefore, a source of candidate agents is one or more than one library of molecules based on one or more than one known compound that increases or decreases CMR1 channel conductivity in which the structure of the compound is changed at one or more positions of the molecule to contain more or fewer chemical moieties or different chemical moieties. The structural changes made to the molecules in creating the libraries of analog activators/inhibitors can be directed, random, or a combination of both directed and random substitutions and/or additions. One of ordinary skill in the art in the preparation of combinatorial libraries can readily prepare such libraries based on the existing compounds.

A variety of other reagents also can be included in the mixture. These include reagents such as salts, buffers, neutral proteins (e.g., albumin), detergents, etc. that can be used to facilitate optimal protein-protein and/or protein-nucleic acid binding. Such a reagent can also reduce non-specific or background interactions of the reaction components. Other reagents that improve the efficiency of the assay such as nuclease inhibitors, antimicrobial agents, and the like can also be used.

Examples of methods for the synthesis of molecular libraries can be found in the art, for example in: Zuckermann et al. (1994). *J. Med. Chem.* 37:2678. Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (U.S. Pat. No. 5,223,409), spores (U.S. Pat. No. 5,571, 698), plasmids (Cull et al. (1992) *Proc. Natl. Acad. Sci. USA* 89:1865-1869) orphage (see e.g., Scott and Smith (1990) *Science* 249:3 86-390).

In one aspect, the invention provides a method of identifying a compound that increases or decreases the expression of a cCMR1 protein, comprising the steps of: (a) contacting a test compound with a cell comprising a mechanism for regulating the expression of a cCMR gene; and (b) determining whether the test compound increases or decreases the expression of a gene controlled by said mechanism from the cell. The mechanism for regulating the expression of a cCMR gene includes the mechanism by which nuclear, cytoplasmic, or intracellular factors influence the control of gene action at the level of transcription or translation. For example, the mechanism includes gene activation or gene repression. The cell comprising a mechanism for regulating the expression of a cCMR gene can be a native host cell that expresses cCMR endogenously, such as a canine DRG cell. The cell can also be a recombinant cell containing a recombinant DNA sequence having a regulatory sequence for a cCMR gene, and the regulatory sequence is operably linked to a gene, preferably a reporter gene.

The effect of the compound on the expression of a gene controlled by the regulatory sequence of CMR1 can be measured by a variety of means. For example, the effect can be measured by the amount of mRNA or protein of the gene from the cell, or by the activity of the gene product from the cell. When a reporter gene is used, the effect can be measured as the level of reporter gene product from the cell. For example, when the CMR1 regulatory sequence is operably linked to a GFP gene, the effect of the compound on gene expression can be measured as the effect of the compound on emissions of green fluorescence from the cell using a fluorometer. When an endogenous cCMR 1 cell is used, the effect of the compound on gene expression can be measured by the amount of cCMR1 mRNA or protein inside the cell using methods described infra (i.e., Northern Blot, RT-PCR, SDS-PAGE, Western Blot, immunohisto- or immunocytochemistry, radioreceptor ligand binding, etc). Alternatively, the conductivity of the cCMR1 channel can be used to measure the effect of the compound on the expression of the cCMR1 protein.

The cell-based method described herein not only identifies compounds that regulate cCMR1 expression directly via binding to one or more than one regulatory sequence of the cCMR1 gene, but also identifies compounds that regulate cCMR1 expression indirectly via binding to other cellular components whose activities influence cCMR1 expression or protein stability. For example, compounds that regulate the activity of a transcriptional activator or inhibitor for cCMR1 genes can be identified using the method described herein. Compounds that regulate the activity of a protease that degrades the cCMR1 protein in vivo can also be identified.

The invention also provides a method of identifying a compound that increases or decreases the conductivity of a cCMR1 ion channel, comprising the steps of: (a) contacting a test compound with the ion channel; and (b) determining whether the test compound increases or decreases the conductivity of the ion channel. In some embodiments, the cCMR1 ion channel is expressed on the surface of a host cell. The cell can be a native host cell for cCMR1 that expresses the cCMR1 endogenously, for example, a dog DRG or TG cell. The cell can also be a recombinant host cell for cCMR1, for example, a CHO or COS cell expressing a cCMR1 recombinantly.

In some other embodiments, the cCMR1 ion channel is associated with an isolated membrane preparation. The membrane preparation can be isolated from a native host cell that expresses cCMR1 on its cell surface, or from a recombinant host cell that expresses cCMR1 on its cell surface. It can also be prepared from the biological membranes, such as the tissue membrane, plasma membrane, cell membrane, or internal organelle membrane comprising the cCMR1 channel. Methods are known to those skilled in the art for isolation and preparation of biological membrane preparations. For example, such a method can include the steps of mechanical or enzymic disruption of the tissue or cells, centrifugation to separate the membranes from other components, and resuspending the membrane fragments or vesicles in suitable buffer solution. Alternatively, the membrane-containing preparation can also be derived from artificial membranes. Purified cCMR1 protein can be reconstituted into lipid bilayers to form the artificial membrane vesicles (see Chen et al., 1996, *J. Gen. Physiol.* 108:237-250). Such type of membrane vesicle can be very specific to the channel of interest, avoiding the problem of contamination with other channels. Methods are known to those skilled in the art to prepare artificial membrane vesicles.

In some embodiments, membrane vesicles comprising the cCMR1 can provide an easier format for the inventive assays and methods, because cell lysis and/or shear is not as much of a concern during the assay. In other embodiments, however, cells expressing the cCMR1 are preferred, for example, when the cell membrane preparation procedure destroys or inactivates the channel of interest.

The test compound can be evaluated for its ability to increase or decrease the ion conductivity of a cCMR1 channel. Known to those skilled in the are methods for measuring a CMR1 channel conductivity, for example, via the stimulation of cellular depolarization or an increase in intracellular calcium ion levels. The level of intracellular calcium can be assessed using a calcium ion-sensitive fluorescent indicator, such as a calcium ion-sensitive fluorescent dye. Suitable calcium ion-sensitive fluorescent dyes include, for example, quin-2 (see, e.g., Tsien et al., J. Cell Biol., 94:325, 1982), fura-2 (see, e.g., Grynkiewicz et al., J. Biol. Chem., 260:3440, 1985), fluo-3 (see, e.g., Kao et al., J. BioL—43 Chem., 264:8179, 1989) and rhod-2 (see, e.g., Tsien et al., J. Biol. Chem., Abstract 89a, 1987). Suitable calcium ion-sensitive fluorescent dyes are commercially available from, for example, Molecular Probes (Eugene, Oreg.). Cellular fluorescence can also be monitored using a fluorometer or a flow cytometer having a fluorescence lamp and detector.

The cCMR1 cation channels function to transport not only divalent cations, for example, $Ca^{++}$, but also monovalent cations, for example, $Na^+$ or $K^+$. Therefore, assays for determining changes in the transport of monovalent cation can also be performed to measure the conductivity of a cCMR1 channel. $Na^+$- and $K^+$-sensitive dyes are known in the art and commercially available from, for example, Molecular Probes (Eugene, Oreg.).

The conductivity of a cCMR1 channel can also be measured by electrophysiologic techniques such as patch-clamp. Patch-clamp techniques are routinely used for studying electrical activities in cells, cell membranes, and isolated tissues. It involves forming an electrically tight, high-resistance seal between a micropipette and the plasma membrane. The current flowing through individual ion channels within the plasma membrane can then be measured. Different variants on the techniques allow different surfaces of the plasma membrane to be exposed to the bathing medium. The four most common variants include on-cell patch, inside-out patch, outside-out patch, and whole-cell clamp.

A patch-clamp method is commonly used with a voltage clamp that controls the voltage across the membrane and measures current flow. During the voltage clamp process, a microelectrode is inserted into a cell and current injected through the electrode so as to hold the cell membrane potential at some predefined level. A patch-clamp method can also be used with current-clamp methods, in which the current is controlled and the voltage is measured.

The assays to identify a compound that decreases cCMR1 channel conductivity are preferably performed under conditions in which the particular ion channel is activated. For example, such assays can be performed at a temperature at which CMR1 is activated . . . Studies from whole-cell patch clamp recordings indicated that cCMR1 is activated at cool temperatures at or below about 17° C. (Example 7 infra). Alternatively, such assays can be performed in the presence of a compound that activates the cCMR1, such as the cool compound menthol or icilin, or the pungent compound mustard oil. In addition, such assay can be performed at conditions when the cCMR1 channel is depolarized, such as by clamping the channel at a depolarized potential.

Conversely, when seeking to identify a compound that increases cCMR1 channel conductivity, test conditions are preferably adjusted wherein the cCMR1 channel is not active or is otherwise blocked. For example, such assays can be performed at a CMR1 non-activation temperature. Unlike the rat CMR1 that is still active at room temperature, cCMR1 is inactivated at room temperature (Example 7 infra). Alternatively, such assays can be performed in the presence of a compound that decreases the conductivity of the cCMR1 channel. In addition, such assays can be performed in the presence of extracellular $Ca^{2+}$ that is sufficient to desensitize the cCMR1 channel. A person of ordinary skill in the art is able to determine the appropriate concentration of extracellular $Ca^{2+}$ that is sufficient to desensitize the cCMR1 channel by routine experimentation. Furthermore, such assays can be performed at conditions when the cCMR1 channel is hyperpolarized, such as by clamping the channel at a hyperpolarized potential.

Assays for the identification of cCMR1 modulators can be carried out manually or using an automated system. Automated systems are preferred if high throughput screenings are performed. For example, one type of automated system utilizes multi-well culture plates, for example, 96-well, 384-well or 1536-well culture plates, wherein each well contains recombinant cells having a nucleic acid encoding the cCMR1 protein. The plate is loaded into a fluorometer, for example, the FlexStation™ (from Molecular Devices Corp., Sunnyvale, Calif.), that can measure the calcium flux and/or membrane potential of the cells in each of the wells. Solutions containing the calcium ion-sensitive fluorescent indicator dye or test compounds can be automatically added to each of the wells. The temperature in the fluorometer can be controlled according to the type of assay that is performed, for example, temperatures can be adjusted to a temperature above the CMR-activating temperature, for example, above 28° C., to test compounds suspected of being CMR1 agonists. Likewise, temperatures can be adjusted to a CMR-activating temperature, for example, at or below 28° C., to test compounds suspected of being CMR1 antagonists.

After the CMR1 channel has been activated and allows the influx of cations (such as $Ca^{++}$ ions), the intracellular accumulation of the $Ca^{++}$ ions promotes a negative feedback and inactivation of the CMR1 channel. The CMR1 becomes reactivated after intracellular $Ca^{++}$ levels decrease by, for example, $Ca^{++}$ being pumped out of the cell or taken up into intracellular organelles.

Although the CMR1 channel can allow the influx of $Ca^{++}$ ions in response to cool to cold temperatures, it is somewhat of a leaky ion channel. Some CMR1 channels will permit the influx of $Ca^{++}$ ions even at non-activating temperatures, for example, at above 28° C. In conventional assay systems, extracellular $Ca^{++}$ concentrations in the mM range are typically used, which can lead to the intracellular accumulation of calcium even at non-activating temperatures, causing the negative feedback inactivation of CMR1.

Therefore, another aspect of the invention is a method of identifying a compound that increases or decreases the conductivity of a mammalian CMR1 ion channel, comprising the steps of: (a) incubating the ion channel in a buffer solution containing a sub-inactivating amount of calcium; (b) activating the ion channel; (c) contacting the ion channel with a test compound; (d) increasing the amount of calcium in the buffer solution; and e) determining the intracellular amount of calcium, and comparing the amount with that of a control wherein the ion channel was not contacted with the test compound. A "sub-inactivating amount of calcium" is the amount of extracellular $Ca^{++}$ that would not cause intracellular accumulation of the $Ca^{++}$ ions to an extent that promotes a negative feedback and inactivation of the CMR1 channel. A person skilled in the art can determine the "sub-inactivating amount of calcium" for a particular CMR1 channel experimentally. In some embodiments, the "sub-inactivating amount of calcium' is essentially zero calcium in the buffer solution. In other embodiments, the "sub-inactivating amount of calcium' is in the µM range of calcium in the buffer solution. The method of the invention includes a method comprising steps (a) to (e) as described herein, wherein step (c) precedes step (b).

After a compound has been identified that meets the desired criteria for modulating CMR1 activity or expression, the compound can then be administered to live animal. This can be useful to establish toxicity and other pharmacological parameters important for establishing dosing regimens. For example, after a compound is identified using an ex vivo system that contains a cCMR1 polypeptide, the compound can be administered to a dog to examine various pharmacological aspects of the compound in the dog. The cCMR1 systems as described herein are particularly advantageous for identifying and establishing dosing regimens in humans, because dogs, particularly large breeds, are closer in weight to humans as compared to rats or mice and therefore provide a more suitable animal model for estimating human dosing.

The compound can also be administered to animals to assess the ability of the compound to alter nociceptive processes. Various animal models of pain exist, for example, the spinal nerve ligation (SNL) model of nerve injury, which is a neuropathic pain model in rats developed by Kim and Chung (Pain, 50:355-363, 1992).

Other suitable animal models of pain can be utilized in connection with the teachings herein. Commonly studied rodent models of neuropathic pain include the chronic constriction injury (CCI) or Bennett model; neuroma or axotomy model; and the partial sciatic transection or Seltzer model (Shir et al., *Neurosci. Lett.*, 115:62-67, 1990). Exemplary neuropathic pain models include several traumatic nerve injury preparations (Bennett et al., *Pain* 33: 87-107, 1988; Decosterd et al., *Pain* 87: 149-58, 2000; Kim et al., *Pain* 50: 355-363, 1992; Shir et al., *Neurosci Lett* 115: 62-7, 1990), neuroinflammation models (Chacur et al., *Pain* 94: 231-44, 2001; Milligan et al., *Brain Res* 861: 105-16, 2000) diabetic neuropathy (Calcutt et al., *Br J Pharmacol* 122: 1478-82, 1997), virus-induced neuropathy (Fleetwood-Walker et al., *J Gen Virol* 80: 2433-6, 1999), vincristine neuropathy (Aley e t al., *Neuroscience* 73: 259-65, 1996; Nozaki-Taguchi et al., *Pain* 93: 69-76, 2001), and paclitaxel neuropathy (Cavaletti et al., *Exp Neurol* 133: 64-72, 1995), as well as acute nociceptive tests models and inflammatory models (Brennan, T. J. et al. *Pain* 64:493, 1996; D'Amour, F. E. and Smith, D. L. *J Pharmacol* 72: 74-79, 1941; Eddy, N. B. et al. *J Pharmacol Exp Ther* 98:121, 1950; Haffner, F. *Dtsch Med Wochenschr* 55:731, 1929; Hargreaves, K. et al. *Pain* 32: 77-88, 1988; Hunskaar, S. et al. *J Neurosci Meth* 14:69, 1985; Randall, L. O. and Selitto, J. J. *Arch. Int. Pharmacodyn* 111: 409-419, 1957; Siegmund, E. et al. *Proc Soc Exp Bio Med* 95:729, 1957).

Therefore, in another embodiment, the invention provides a method of identifying a compound useful for treating pain, comprising the steps of: (a) contacting a test compound with a cCMR1 ion channel; and (b) determining whether the test compound increases or decreases the conductivity of the ion channel. In some embodiments, the method further comprises the steps of: (a) administering the test compound to an animal; and (b) determining the extent to which the test compound alters the nociceptive/nocifensive response of the animal.

In some embodiments, the animal model of pain involves a rodent, for example, a rat or mouse; in another aspect the animal model of pain involves a dog, for example, the skin twitch test (Kamerling et al. *Pharmacol. Biochem. Behav.* 17:733-740, 1982; also, see Burns J C et al. *Perspect Biol Med. Autumn;* 35(1): 68-73, 1991).

Therapeutic efficacy and toxicity may be determined by standard pharmaceutical procedures in cell cultures or experimental animals by calculating, for example, the $ED_{50}$ (the dose therapeutically effective in 50% of the population) and the $LD_{50}$ (the dose lethal to 50% of the population). The dose ratio between toxic and therapeutic effects is the therapeutic index, and it can be expressed as the ratio, $LD_{50}/ED_{50}$. The data obtained from cell culture assays using recombinant CMR1 and animal studies, such as canine studies, is used in formulating a range of dosage for human use. The dosage contained in such compositions preferably gives rise to a range of circulating concentrations that include the $ED_{50}$ with little or no toxicity. The dosage varies within this range depending upon the dosage form employed, sensitivity of the patient and the route of administration. The exact dosage will be determined by the one administering the dose, in light of factors related to the subject requiring treatment. Dosage and administration are adjusted to provide sufficient levels of the active agent or to maintain the desired effect, for example, effective pain relief. Factors that may be taken into account include the severity of the pain and other factors, including the general health of the subject, age, weight and gender of the subject, diet, time and frequency of administration, drug combination(s), reaction sensitivities and tolerance/response to therapy.

The pharmaceutical compositions containing a compound that has been identified as modulating CMR1 activity can be administered by any number of routes including, but not limited to, oral, intravenous, intramuscular, intraarticular, intraarterial, intramedullary, intrathecal, epidural, intraventricular, transdermal, subcutaneous, intraperitoneal, intranasal, enteral, topical, sublingual, inhalational, intraocular, intra-aural or rectal means.

In addition to the active ingredients, these pharmaceutical compositions may contain suitable, pharmaceutically acceptable carriers comprising excipients and auxiliaries which facilitate processing of the active compounds into preparations that can be used pharmaceutically or which facilitate absorption or distribution of the active compounds. Further details on techniques for formulation and administration may be found in Remington's Pharmaceutical Sciences, Maack Publishing Co., Easton, Pa.

Pharmaceutical compositions for oral administration can be formulated using pharmaceutically acceptable carriers well-known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

TABLE 1

```
      ACGCGGGGAAGGCCGGCAGGATCTTTCCAGGGAAAGCAAATCCTGCCTCACAAACCTCAA          SEQ1
  1 ---------+---------+---------+---------+---------+---------+  60
      TGCGCCCCTTCCGGCCGTCCTAGAAAGGTCCCTTTCGTTTAGGACGGAGTGTTTGGAGTT

CCGGAGAGATGTCCTTCGAGGGGGCCAGGCTCAGCATGAGGAACAGAAGGAACGGCACGC
 61 ---------+---------+---------+---------+---------+---------+  120
      GGCCTCTCTACAGGAAGCTCCCCCGGTCCGAGTCGTACTCCTTGTCTTCCTTGCCGTGCG
                                     M  S  F  E  G  A  R  L  S  M  R  N  R  R  N  G  T  L  -   SEQ2
      TGGACAGCACCCGGACCCTGTACTCCAGCACGTCTCGGAGCACCGACGTGTCCTACAGCG
121 ---------+---------+---------+---------+---------+---------+ 180
      ACCTGTCGTGGGCCTGGGACATGAGGTCGTGCAGAGCCTCGTGGCTGCACAGGATGTCGC
       D  S  T  R  T  L  Y  S  S  T  S  R  S  T  D  V  S  Y  S  E  -
      AAAGCGACTTGGTGAATTTTATTCAAGCAAATTTTAAGAAACGAGAATGTGTCTTCTTCA
181 ---------+---------+---------+---------+---------+---------+ 240
      TTTCGCTGAACCACTTAAAATAAGTTCGTTTAAAATTCTTTGCTCTTACACAGAAGAAGT
       S  D  L  V  N  F  I  Q  A  N  F  K  K  R  E  C  V  F  F  T  -
      CCAAAGATTCCAAGGCCACGGAAAATGTGTGCAAGTGTGGCTATGCCCAGAGCCAGCACA
241 ---------+---------+---------+---------+---------+---------+ 300
      GGTTTCTAAGGTTCCGGTGCCTTTTACACACGTTCACACCGATACGGGTCTCGGTCGTGT
       K  D  S  K  A  T  E  N  V  C  K  C  G  Y  A  Q  S  Q  H  I  -
      TAGAAGGCACCCAGATCAACTCAAACGAGAAATGGAATTACAAGAAACACACCAAGGAAT
301 ---------+---------+---------+---------+---------+---------+ 360
      ATCTTCCGTGGGTCTAGTTGAGTTTGCTCTTTACCTTAATGTTCTTTGTGTGGTTCCTTA
       E  G  T  Q  I  N  S  N  E  K  W  N  Y  K  K  H  T  K  E  F  -
      TTCCGACTGACGCCTTTGGGGATATTCAGTTTGAGACTCTGGGGAAGAAAGGGAAGTATA
361 ---------+---------+---------+---------+---------+---------+ 420
      AAGGCTGACTGCGGAAACCCCTATAAGTCAAACTCTGAGACCCCTTCTTTCCCTTCATAT
       P  T  D  A  F  G  D  I  Q  F  E  T  L  G  K  K  G  K  Y  I  -
      TCCGCCTGTCCTGTGACACGGATGCGGAGACCCTCTATGAGCTGCTGACCCAGCACTGGC
421 ---------+---------+---------+---------+---------+---------+ 480
      AGGCGGACAGGACACTGTGCCTACGCCTCTGGGAGATACTCGACGACTGGGTCGTGACCG
       R  L  S  C  D  T  D  A  E  T  L  Y  E  L  L  T  Q  H  W  H  -
      ACCTGAAAACGCCCAACCTGGTCATATCTGTCACCGGCGGCGCCAAGAACTTCGCCCTGA
481 ---------+---------+---------+---------+---------+---------+ 540
      TGGACTTTTGCGGGTTGGACCAGTATAGACAGTGGCCGCCGCGGTTCTTGAAGCGGGACT
       L  K  T  P  N  L  V  I  S  V  T  G  G  A  K  N  F  A  L  K  -
      AGCCGAGGATGCGCAAGATCTTCAGCCGCCTCATCTACATCGCGCAGTCCAAAGGTGCTT
541 ---------+---------+---------+---------+---------+---------+ 600
      TCGGCTCCTACGCGTTCTAGAAGTCGGCGGAGTAGATGTAGCGCGTCAGGTTTCCACGAA
       P  R  M  R  K  I  F  S  R  L  I  Y  I  A  Q  S  K  G  A  W  -
      GGATTCTCACTGGAGGAACCCATTATGGCCTGATGAAGTACATCGGGGAGGTGGTGAGAG
601 ---------+---------+---------+---------+---------+---------+ 660
      CCTAAGAGTGACCTCCTTGGGTAATACCGGACTACTTCATGTAGCCCCTCCACCACTCTC
       I  L  T  G  G  T  H  Y  G  L  N  K  Y  I  G  E  V  V  R  D  -
      ACAACACCATCAGCAGGAATTCAGAGGAGAACATTGTGGCCATTGGCATAGCGGCTTGGG
661 ---------+---------+---------+---------+---------+---------+ 720
      TGTTGTGGTAGTCGTCCTTAAGTCTCCTCTTGTAACACCGGTAACCGTATCGCCGAACCC
       N  T  I  S  R  N  S  E  E  N  I  V  A  I  G  I  A  A  W  G  -
      GCATGGTCTCCAACAGGGACACTCTCCTCAGGAATTGCGATGCTGAGGGATATTTTTCAG
721 ---------+---------+---------+---------+---------+---------+ 780
      CGTACCAGAGGTTGTCCCTGTGAGAGGAGTCCTTAACGCTACGACTCCCTATAAAAAGTC
       M  V  S  N  R  D  T  L  L  R  N  C  D  A  E  G  Y  F  S  A  -
      CTCAGTACATAATGGATGACTTCAAGAGAGACCCTCTGTATATCTTGGACAACAACCACA
781 ---------+---------+---------+---------+---------+---------+ 840
      GAGTCATGTATTACCTACTGAAGTTCTCTCTGGGAGACATATAGAACCTGTTGTTGGTGT
       Q  Y  I  M  D  D  F  K  R  D  P  L  Y  I  L  D  N  N  H  T  -
      CCCATCTGCTGCTTGTGGACAACGGCTGCCATGGACATCCTACAGTTGAAGCAAAACTCC
841 ---------+---------+---------+---------+---------+---------+ 900
      GGGTAGACGACGAACACCTGTTGCCGACGGTACCTGTAGGATGTCAACTTCGTTTTGAGG
       H  L  L  V  D  N  G  C  H  G  H  P  T  V  E  A  K  L  R  -
      GGAATCAGCTGGAGAAGTACATCTCCGAGCGCACTATTCAAGATTCCAACTATGGTGGCA
901 ---------+---------+---------+---------+---------+---------+ 960
      CCTTAGTCGACCTCTTCATGTAGAGGCTCGCGTGATAAGTTCTAAGGTTGATACCACCGT
       N  Q  L  E  K  Y  I  S  E  R  T  I  Q  D  S  N  Y  G  G  K  -
      AGATCCCCATTGTGTGTTTTGCCCAAGGAGGTGGCAGAGAAACTTTGAAAGCCATCAACA
961 ---------+---------+---------+---------+---------+---------+ 1020
      TCTAGGGGTAACACACAAAACGGGTTCCTCCACCGTCTCTTTGAAACTTTCGGTAGTTGT
       I  P  I  V  C  F  A  Q  G  G  G  R  E  T  L  K  A  I  N  T  -
      CCTCCATCAAAAGCAAAATCCCCTGTGTGGTGGTGGAAGGCTCAGGGCAGATTGCAGACG
1021 ---------+---------+---------+---------+---------+---------+ 1080
      GGAGGTAGTTTTCGTTTTAGGGGACACACCACCACCTTCCGAGTCCCGTCTAACGTCTGC
       S  I  K  S  K  I  P  C  V  V  V  E  G  S  G  Q  I  A  D  V  -
      TGATCGCGAGCCTGGTGGAGGTGGAGGACGTCCTGACGTCATCTGTGGTCAAGGAGAAGT
```

TABLE 1-continued

```
1081 ---------+---------+---------+---------+---------+---------+ 1140
     ACTAGCGCTCGGACCACCTCCACCTCCTGCAGGACTGCAGTAGACACCAGTTCCTCTTCA
      I  A  S  L  V  E  V  E  D  V  L  T  S  S  V  V  K  E  K  L -
     TGGTGCGCTTCTTACCCCGCACAGTGTCCCGGCTGCCTGAGGAGGAGACCGAGAGTTGGA
1141 ---------+---------+---------+---------+---------+---------+ 1200
     ACCACGCGAAGAATGGGCGTGTCACAGGGCCGACGGACTCCTCCTCTGGCTCTCAACCT
      V  R  F  L  P  R  T  V  S  R  L  P  E  E  E  T  E  S  W  I -
     TCAAATGGCTCAAAGAAATTCTCGAAAGTTCTCACCTATTAACAGTTATTAAAATGGAAG
1201 ---------+---------+---------+---------+---------+---------+ 1260
     AGTTTACCGAGTTTCTTTAAGAGCTTTCAAGAGTGGATAATTGTCAATAATTTTACCTTC
      K  W  L  K  E  I  L  E  S  S  H  L  L  T  V  I  K  M  E  E -
     AAGCTGGAGACGAAATTGTGAGCAATGCTATTTCTTATGCTTTGTACAAAGCCTTTAGCA
1261 ---------+---------+---------+---------+---------+---------+ 1320
     TTCGACCTCTGCTTTAACACTCGTTACGATAAAGAATACGAAACATGTTTCGGAAATCGT
      A  G  D  E  I  V  S  N  A  I  S  Y  A  L  Y  K  A  F  S  T -
     CCAATGAACAAGATAAGGATAACTGGAATGGGCAGCTGAAGCTTCTGCTGGAATGGAACC
1321 ---------+---------+---------+---------+---------+---------+ 1380
     GGTTACTTGTTCTATTCCTATTGACCTTACCCGTCGACTTCGAAGACGACCTTACCTTGG
      N  E  Q  D  K  D  N  W  N  G  Q  L  K  L  L  E  W  N  Q   -
     AGCTGGACCTAGCCAATGAGGAGATATTCACCAACGACCGCCGATGGGGTCTGCTGATC
1381 ---------+---------+---------+---------+---------+---------+ 1440
     TCGACCTGGATCGGTTACTCCTCTATAAGTGGTTGCTGGCGGCTACCCCAGACGACTAG
      L  D  L  A  N  E  E  I  F  T  N  D  R  R  W  G  S  A  D  L -
     TGCAAGAGGTCATGTTTACAGCTCTCATAAAGGACAGACCCAAGTTTGTCCGCCTCTTCC
1441 ---------+---------+---------+---------+---------+---------+ 1500
     ACGTTCTCCAGTACAAATGTCGAGAGTATTCCTGTCTGGGTTCAAACAGGCGGAGAAGG
      Q  E  V  M  F  T  A  L  I  K  D  R  P  K  F  V  R  L  F  L -
     TGGAGAATGGGTTGAACCTGCGCAAGTTTCTCACCAATGACGTCCTCACTGAACTCTTCT
1501 ---------+---------+---------+---------+---------+---------+ 1560
     ACCTCTTACCCAACTTGGACGCGTTCAAAGAGTGGTTACTGCAGGAGTGACTTGAGAAGA
      E  N  G  L  N  L  R  K  F  L  T  N  D  V  L  T  E  L  F  S -
     CCAACCACTTCAGCACCCTTGTCTACCGGAACCTGCAGATTGCCAAGAATTCCTATAACG
1561 ---------+---------+---------+---------+---------+---------+ 1620
     GGTTGGTGAAGTCGTGGGAACAGATGGCCTTGGACGTCTAACGGTTCTTAAGGATATTGC
      N  H  F  S  T  L  V  Y  R  N  L  Q  I  A  K  N  S  Y  N  D -
     ATGCCCTCCTCACATTCGTCTGGAAACTGGTGGCCAACTTCCGGAGAGGCTTCCGAAAGG
1621 ---------+---------+---------+---------+---------+---------+ 1680
     TACGGGAGGAGTGTAAGCAGACCTTTGACCACCGGTTGAAGGCCTCTCCGAAGGCTTTCC
      A  L  L  T  F  V  W  K  L  V  A  N  F  R  R  G  F  R  K  E -
     AAGACAGAAGTAGCAGGGATGACATAGATGTAGAACTTCACGATGTGTCTCCTATCACTC
1681 ---------+---------+---------+---------+---------+---------+ 1740
     TTCTGTCTTCATCGTCCCTACTGTATCTACATCTTGAAGTGCTACACAGAGGATAGTGAG
      D  R  S  S  R  D  D  I  D  V  E  L  H  D  V  S  P  I  T  R -
     GGCACCCGCTGCAAGCACACTTCATCTGGGCCATTCTTCAGAACAAGAAGGAACTGTCCA
1741 ---------+---------+---------+---------+---------+---------+ 1800
     CCGTGGGCGACGTTCGTGTGAAGTAGACCCGGTAAGAAGTCTTGTTCTTCCTTGACAGGT
      H  P  L  Q  A  H  F  I  W  A  I  L  Q  N  K  K  E  L  S  K -
     AGGTCATTTGGGAGCAGACCAGGGGCTGCACGTTGGCAGCCCTGGGAGCCAGCAAGCTTC
1801 ---------+---------+---------+---------+---------+---------+ 1860
     TCCAGTAAACCCTCGTCTGGTCCCCGACGTGCAACCGTCGGGACCCTCGGTCGTTCGAAG
      V  I  W  E  Q  T  R  G  C  T  L  A  A  L  G  A  S  K  L  L -
     TGAAGACTCTGGCCAAGGTGAAGAATGACATCAATGCTGCAGGGGAGTCCGAGGAGCTGG
1861 ---------+---------+---------+---------+---------+---------+ 1920
     ACTTCTGAGACCGGTTCCACTTCTTACTGTAGTTACGACGTCCCCTCAGGCTCCTCGACC
      K  T  L  A  K  V  K  N  D  I  N  A  A  G  E  S  E  E  L  A -
     CAAATGAGTATGAGACCCGTGCAGTTGAGCTGTTCACGGAGTGCTACAGCAGCGACGAGG
1921 ---------+---------+---------+---------+---------+---------+ 1980
     GTTTACTCATACTCTGGGCACGTCAACTCGACAAGTGCCTCACGATGTCGTCGCTGCTCC
      N  E  Y  E  T  R  A  V  E  L  F  T  E  C  Y  S  S  D  E  D -
     ACCTGGCCGAGCAGCTGCTGGTGTACTCCTGCGAAGCCTGGGGCGGGAGCAACTGCTTGG
1981 ---------+---------+---------+---------+---------+---------+ 2040
     TGGACCGGCTCGTCGACGACCACATGAGGACGCTTCGGACCCCGCCCTCGTTGACGAACC
      L  A  E  Q  L  L  V  Y  S  C  E  A  W  G  G  S  N  C  L  E -
     AGCTGGCGGTGGAGGCCACGGACCAGCACTTCATCGCCCAGCCCGGGGTCCAGAATTTTC
2041 ---------+---------+---------+---------+---------+---------+ 2100
     TCGACCGCCACCTCCGGTGCCTGGTCGTGAAGTAGCGGGTCGGGCCCCAGGTCTTAAAAG
      L  A  V  E  A  T  D  Q  H  F  I  A  Q  P  G  V  Q  N  F  L -
     TTTCCAAGCAATGGTATGGAGAGATTTCCCGAGACACCAAGAACTGGAAGATTATCCTGT
2101 ---------+---------+---------+---------+---------+---------+ 2160
     AAAGGTTCGTTACCATACCTCTCTAAAGGGCTCTGTGGTTCTTGACCTTCTAATAGGACA
      S  K  Q  W  Y  G  E  I  S  R  D  T  K  N  W  K  I  I  L  C -
     GTTTGTTTATTATACCCTTGGTGGGCTGTGGCTTTGTATCCTTTAGGAAGAGGCCCATCG
2161 ---------+---------+---------+---------+---------+---------+ 2220
     CAAACAAATAATATGGGAACCACCCGACACCGAAACATAGGAAATCCTTCTCCGGGTAGC
      L  F  I  I  P  L  V  G  C  G  F  V  S  F  R  K  R  P  I  D -
     ACAAGCACAAGAAGATCCTGTGGTACTACGTGGCGTTCTTCACCTCCCCCTTTGTGGTCT
```

TABLE 1-continued

```
2221 ---------+---------+---------+---------+---------+---------+ 2280
     TGTTCGTGTTCTTCTAGGACACCATGATGCACCGCAAGAAGTGGAGGGGGAAACACCAGA
       K  H  K  K  I  L  W  Y  Y  V  A  F  F  T  S  P  F  V  V  F -
     TCGCCTGGAACGTGGTCTTCTACATCGCCTTCCTCCTGCTCTTTGCCTACGTGCTGCTCA
2281 ---------+---------+---------+---------+---------+---------+ 2340
     AGCGGACCTTGCACCAGAAGATGTAGCGGAAGGAGGACGAGAAACGGATGCACGACGAGT
       A  W  N  V  V  F  Y  I  A  F  L  L  L  F  A  Y  V  L  L  M -
     TGGATTTTCACTCAGTGCCACACTCCCCCGAGCTGGTCCTCTACGCACTGGTCTTTGTCC
2341 ---------+---------+---------+---------+---------+---------+ 2400
     ACCTAAAAGTGAGTCACGGTGTGAGGGGGCTCGACCAGGAGATGCGTGACCAGAAACAGG
       D  F  H  S  V  P  H  S  P  H  L  V  L  Y  A  L  V  F  V  L -
     TGTTCTGTGATGAAGTGAGACAGTGGTACATGAATGGGGTGAATTATTTTACCGACCTGT
2401 ---------+---------+---------+---------+---------+---------+ 2460
     ACAAGACACTACTTCACTCTGTCACCATGTACTTACCCCACTTAATAAAATGGCTGGACA
       F  C  D  E  V  R  Q  W  Y  M  N  G  V  N  Y  F  T  D  L  W -
     GGAATGTCATGGACACACTTGGGCTTTTTTACTTCATAGCAGGCATTGTGTTTCGGCTCC
2461 ---------+---------+---------+---------+---------+---------+ 2520
     CCTTACAGTACCTGTGTGAACCCGAAAAAATGAAGTATCGTCCGTAACACAAAGCCGAGG
       N  V  M  D  T  L  G  L  F  Y  F  I  A  G  I  V  F  R  L  H -
     ACCCTTCTAATAAAACCTCTTTGTATTCCGGACGAGTCATCTTTTGCCTGGATTACATTA
2521 ---------+---------+---------+---------+---------+---------+ 2580
     TGGGAAGATTATTTTGGAGAAACATAAGGCCTGCTCAGTAGAAAACGGACCTAATGTAAT
       P  S  N  K  T  S  L  Y  S  G  R  V  I  F  C  L  D  Y  I  I -
     TATTCACCCTAAGGTTGATCCACATTTTCACCGTAAGCAGAAATTTGGGACCGAAGATTA
2581 ---------+---------+---------+---------+---------+---------+ 2640
     ATAAGTGGGATTCCAACTAGGTGTAAAAGTGGCATTCGTCTTTAAACCCTGGCTTCTAAT
       F  T  L  R  L  I  H  I  F  T  V  S  R  N  L  G  P  K  I  I -
     TAATGTTGCAGAGGATGCTGATCGACGTGTTTTTCTTCCTGTTTCTGTTTGCCGTGTGGA
2641 ---------+---------+---------+---------+---------+---------+ 2700
     ATTACAACGTCTCCTACGACTAGCTGCACAAAAAGAAGGACAAAGACAAACGGCACACCT
       M  L  Q  R  M  L  I  D  V  F  F  F  L  F  L  F  A  V  W  M -
     TGGTGGCCTTCGGCGTGGCCAGGCAAGGGATCCTCAGGCAAAATGAGCATCGCTGGAGGT
2701 ---------+---------+---------+---------+---------+---------+ 2760
     ACCACCGGAAGCCGCACCGGTCCGTTCCCTAGGAGTCCGTTTTACTCGTAGCGACCTCCA
       V  A  F  G  V  A  R  Q  G  I  L  R  Q  N  E  H  R  W  R  W -
     GGATATTCCGCTCGGTTATCTACGAGCCCTACCTGGCCATGTTCGGCCAAGTGCCCAGCG
2761 ---------+---------+---------+---------+---------+---------+ 2820
     CCTATAAGGCGAGCCAATAGATGCTCGGGATGGACCGGTACAAGCCGGTTCACGGGTCGC
       I  F  R  S  V  I  Y  E  P  Y  L  A  M  F  G  Q  V  P  S  D -
     ACGTGGATGGTACCACATATGACTTTGCCCACTGCACTTTCACTGGGAATGAGTCCAAGC
2821 ---------+---------+---------+---------+---------+---------+ 2880
     TGCACCTACCATGGTGTATACTGAAACGGGTGACGTGAAAGTGACCCTTACTCAGGTTCG
       V  D  G  T  T  Y  D  F  A  H  C  T  F  T  G  N  E  S  K  P -
     CGCTGTGTGTGGAGCTGGATGAGCACAACCTCCCCCGGTTCCCCGAGTGGATCACCATCC
2881 ---------+---------+---------+---------+---------+---------+ 2940
     GCGACACACACCTCGACCTACTCGTGTTGGAGGGGGCCAAGGGGCTCACCTAGTGGTAGG
       L  C  V  E  L  D  E  H  N  L  P  R  F  P  E  W  I  T  I  P -
     CTCTGGTGTGCATCTACATGCTCTCCACCAACATCCTGCTGGTCAATCTGCTCGTTGCCA
2941 ---------+---------+---------+---------+---------+---------+ 3000
     GAGACCACACGTAGATGTACGAGAGGTGGTTGTAGGACGACCAGTTAGACGAGCAACGGT
       L  V  C  I  Y  M  L  S  T  N  I  L  L  V  N  L  L  V  A  M -
     TGTTTGGCTACACAGTGGGAACGGTCCAGGAGAACAACGATCAGGTCTGGAAGTTCCAGA
3001 ---------+---------+---------+---------+---------+---------+ 3060
     ACAAACCGATGTGTCACCCTTGCCAGGTCCTCTTGTTGCTAGTCCAGACCTTCAAGGTCT
       F  G  Y  T  V  G  T  V  Q  E  N  N  D  Q  V  W  K  F  Q  R -
     GGTACTTCTTGGTGCAGGAGTACTGCAACCGCCTGAACATCCCCTTCCCCTTTGTGGTCT
3061 ---------+---------+---------+---------+---------+---------+ 3120
     CCATGAAGAACCACGTCCTCATGACGTTGGCGGACTTGTAGGGGAAGGGGAAACACCAGA
       Y  F  L  V  Q  E  Y  C  N  R  L  N  I  P  F  P  F  V  V  F -
     TCGCCTACTTCTACATGGTGGTCAAGAAGTGCTTCGGATGCTGCTGCAGGGAGAAACACG
3121 ---------+---------+---------+---------+---------+---------+ 3180
     AGCGGATGAAGATGTACCACCAGTTCTTCACGAAGCCTACGACGACGTCCCTCTTTGTGC
       A  Y  F  Y  M  V  V  K  K  C  F  G  C  C  C  R  E  K  H  A -
     CCGAGCCTTCTGCCTGCTGTTTCAGAAATGAAGACAATGAGACTCTGGCATGGGAGGGTG
3181 ---------+---------+---------+---------+---------+---------+ 3240
     GGCTCGGAAGACGGACGACAAAGTCTTTACTTCTGTTACTCTGAGACCGTACCCTCCCAC
       E  P  S  A  C  C  F  R  N  E  D  N  E  T  L  A  W  E  G  V -
     TCATGAAAGAAATTACCTTGTCAAGATCAACACGGAGGCCAATGACACCTCACAGGAAA
3241 ---------+---------+---------+---------+---------+---------+ 3300
     AGTACTTTCTTTTAATGGAACAGTTCTAGTTGTGCCTCCGATTACTGTGGAGTGTCCTTT
       M  K  E  N  Y  L  V  K  I  N  T  E  A  N  D  T  S  Q  E  M -
     TGAGGCATCGGTTTAGACAGCTGGATACAAAGATTAATGATCTCAAGGGCCTTCTGAAAG
3301 ---------+---------+---------+---------+---------+---------+ 3360
     ACTCCGTAGCCAAATCTGTCGACCTATGTTTCTAATTACTAGAGTTCCCGGAAGACTTTC
       R  H  R  F  R  Q  L  D  T  K  I  N  D  L  K  G  L  L  K  E -
     AGATCGCTAATAAAAATCAAATAGAACTTCATGGACTGTACTGGAGAAAAACCTAATTATA
```

TABLE 1-continued

```
3361 ---------+---------+---------+---------+---------+---------+ 3420
     TCTAGCGATTATTTTAGTTTATCTTGAAGTACCTGACATGACCTCTTTTTGGATTAATAT
       I  A  N  K  I  K  * (SEQ ID NO: 2)
     GCAAGGTGACACCAGAAATCGAAGTGGGAACCAGTCAAGAAAAGCTGATGAACAGTTTTG
3421 ---------+---------+---------+---------+---------+---------+ 3480
     CGTTCCACTGTGGTCTTTAGCTTCACCCTTGGTCAGTTCTTTTCGACTACTTGTCAAAC
     TTACTGACTGCTCAGTAAGAACTGTTCAGGCCGTGGGTATTTAGCAGATGGCTTTCATCA
3481 ---------+---------+---------+---------+---------+---------+ 3540
     AATGACTGACGAGTCATTCTTGACAAGTCCGGCACCCATAAATCGTCTACCGAAAGTAGT
     CCCCAGTGTGCTCAAATCTGGGAAACAGACGTGTGATTGGTTTCCCCCGAGAAGATAGAC
3541 ---------+---------+---------+---------+---------+---------+ 3600
     GGGGTCACACGAGTTTAGACCCTTTGTCTGCACACTAACCAAAGGGGGCTCTTCTATCTG
     ACCCAGGAAGAGCTTCCCCTGAAGGCCACCCTGTTACTTCCTGAGTCTCCACCACTCATA
3601 ---------+---------+---------+---------+---------+---------+ 3660
     TGGGTCCTTCTCGAAGGGGACTTCCGGTGGGACAATGAAGGACTCAGAGGTGGTGAGTAT
     CCCACTGCGGGTCATCTTAGAGTGTGTTCCTGCACTCTTCTTCTTTCTTCACTTTTCCTA
3661 ---------+---------+---------+---------+---------+---------+ 3720
     GGGTGACGCCCAGTAGAATCTCACACAAGGACGTGAGAAGAAGAAAGAAGTGAAAAGGAT
     CTTCTAACTCTGTGCATATTACATCTCTCCTGCAAGGGGTCATGCCTTCCCTCCCATAA
3721 ---------+---------+---------+---------+---------+---------+ 3780
     GAAGATTGAGACACGTATAATGTAGAGAGGACGTTCCCCCAGTACGGAAGGGAGGGTATT
     AAAAGAAAAAAAAAAAAAAAAAAAAAAAAAAAAA (SEQ ID NO: 1)
3781 ---------+---------+---------+---         -  3815
     TTTTCTTTTTTTTTTTTTTTTTTTTTTTTTT
```

TABLE 2

```
C  MSFEGARLSM  RNRRNGTLDS  TRTLYSSTSR  STDVSYSESD  LVNFIQANFK  KRECVFFTKD    60
   |||..||||   ||||||.||   ||||||||.|  |||.||||||  ||||||||||  ||||||.||
H  MSFRAARLSM  RNRRNDTLDS  TRTLYSSASR  STDLSYSESD  LVNFIQANFK  KRECVFFIKD
   ||||||||||  |.||||..|   ||||||||.|  |||.||||||  ||||||||||  ||||||.||
M  MSFEGARLSM  RSRRNGTMGS  TRTLYSSVSR  STDVSYSDSD  LVNFIQANFK  KRECVFFTRD
   ||||||||||  |.||||..|   ||||||||||  ||||||||||  ||||||||||  ||||||||||
R  MSFEGARLSM  RSRRNGTLGS  TRTLYSSVSR  STDVSYSESD  LVNFIQANFK  KRECVFFTRD

C  SKATENVCKC  GYAQSQHIEG  TQINSNEKWN  YKKHTKEFPT  DAFGDIQFET  LGKKGKYIRL   120
   ||||||||||  ||||||.||   ||||.||||| ||||||||||  ||||||||||  |||||||||
H  SKATENVCKC  GYAQSQHMEG  TQINQSEKWN  YKKHTKEFPT  DAFGDIQFET  LGKKGKYIRL
   |||.||.|||  ||||||||||  ||||.|||||  ||||||||||  ||||||||||  ||||||.||
M  SKAMENICKC  GYAQSQHIEG  TQINQNEKWN  YKKHTKEFPT  DAFGDIQFET  LGKKGKYLRL
   |||.|..|||  ||||||||||  ||||||||||  ||||||||||  ||||||||||  ||||||.||
R  SKAMESICKC  GYAQSQHIEG  TQINQNEKWN  YKKHTKEFPT  DAFGDIQFET  LGKKGKYLRL

C  SCDTDAETLY  ELLTQHWHLK  TPNLVISVTG  GAKNFALKPR  MRKIFSRLIY  IAQSKGAWIL   180
   |||||||.||  ||||||||||  ||||||||||  ||||||||||  ||||||||||  ||||||||||
H  SCDTDAEILY  ELLTQHWHLK  TPNLVISVTG  GAKNFALKPR  MRKIFSRLIY  IAQSKGAWIL
   |||||.|||   ||||||||||  ||||||||||  ||||||||||  ||||||||||  ||||||||||
M  SCDTDSETLY  ELLTQHWHLK  TPNLVISVTG  GAKNFALKPR  MRKIFSRLIY  IAQSKGAWIL
   |||||.||||  ||||||||||  ||||||||||  ||||||||||  ||||||||||  ||||||||||
R  SCDTDSETLY  ELLTQHWHLK  TPNLVISVTG  GAKNFALKPR  MRKIFSRLIY  IAQSKGAWIL

C  TGGTHYGLMK  YIGEVVRDNT  ISRNSEENIV  AIGIAAWGMV  SNRDTLLRNC  DAEGYFSAQY   240
   ||||||||||  ||||||||||  |||.||||||  ||||||||||  ||||||.|||  ||||||.|||
H  TGGTHYGLMK  YIGEVVRDNT  ISRSSEENIV  AIGIAAWGMV  SNRDTLIRNC  DAEGYFLAQY
   ||||||||||  ||||||||||  ||||||||||  ||||||||||  ||||||.|.|  |.||.||||
M  TGGTHYGLMK  YIGEVVRDNT  ISRNSEENIV  AIGIAAWGMV  SNRDTLIRSC  DDEGHFSAQY
   ||||||||||  ||||||||||  ||||||||||  ||||||||||  ||||||.|||  ||.||.||||
R  TGGTHYGLMK  YIGEVVRDNT  ISRNSEENIV  AIGIAAWGMV  SNRDTLIRNC  DDEGHFSAQY

C  IMDDFKRDPL  YILDNNHTHL  LLVDNGCHGH  PTVEAKLRNQ  LEKYISERTI  QDSNYGGKIP   300
   .||||.||||  ||||||||||  ||||||||||  ||||||||||  ||||||||||  ||||||||||
H  LMDDFTRDPL  YILDNNHTHL  LLVDNGCHGH  PTVEAKLRNQ  LEKYISERTI  QDSNYGGKIP
   ||||||.|||  ||||||||||  ||||||||||  ||||||||||  |||||||||.  ||||||||||
M  IMDDFTRDPL  YILDNNHTHL  LLVDNGCHGH  PTVEAKLRNQ  LEKYISERTS  QDSNYGGKIP
   ||||||.|||  ||||||||||  ||||||||||  ||||||||||  |||||||||.  ||||||||||
R  IMDDFMRDPL  YILDNNHTHL  LLVDNGCHGH  PTVEAKLRNQ  LEKYISERTS  QDSNYGGKIP

C  IVCFAQGGGR  ETLKAINTSI  KSKIPCVVVE  GSGQIADVIA  SLVEVEDVLT  SSVVKEKLVR   360
   ||||||||||.  ||||||||||  |.||||||||  ||||||||||  ||||||||.||  ||.||||||
H  IVCFAQGGGK  ETLKAINTSI  KNKIPCVVVE  GSGQIADVIA  SLVEVEDALT  SSAVKEKLVR
   ||||||||||  |||.|||||.  ||||||||||  ||||||||||  ||||||||||  ||.||||||
M  IVCFAQGGGR  ETLDAINTSV  KSKIPCVVVE  GSGQIADVIA  SLVEVEDVLT  SSMVKEKLVR
   ||||||||||  |||.|||||.  ||||||||||  ||||||||||  ||||||||||  ||.||||||
R  IVCFAQGGGR  ETLKAINTSV  KSKIPCVVVE  GSGQIADVIA  SLVEVEDVLT  SSMVKEKLVR
```

TABLE 2-continued

```
C  FLPRTVSRLP  EEETESWIKW  LKEILESSHL  LTVIKMEEAG  DEIVSNAISY  ALYKAFSTNE  420
   ||||||||||  |||.||||||  ||||||.|||  ||||||||||  ||||||||||  |||||||.|
H  FLPRTVSRLP  EEETESWIKW  LKEILECSHL  LTVIKMEEAG  DEIVSNAISY  ALYKAFSTSE
   ||||||||||  |||.||||||  ||||||||||  ||||||||||  |.||.||||  ||||||||||
M  FLPRTVSRLP  EEEIESWIKW  LKEILESSHL  LTVIKMEEAG  DEIVSNAISY  ALYKAFSTNE
   ||||||||||  |||.||||||  ||||||.|||  ||||||||||  |.||.||||  ||||.|||||
R  FLPRTVSRLP  EEEIESWIKW  LKEILESPHL  LTVIKMEEAG  DEVVSSAISY  ALYDAFSTNE

C  QDKDNWNGQL  KLLLEWNQLD  LANEEIFTND  RRWGSADLQE  VMFTALIKDR  PKFVRLFLEN  480
   ||||||||||  ||||||||||  |||.||||||  |||.||||||  ||||||||||  ||||||||||
H  QDKDNWNGQL  KLLLEWNQLD  LANDEIFTND  RRWESADLQE  VMFTALIKDR  PKFVRLFLEN
   ||||||||||  ||||||||||  ||..||||.|  ||||||||||  ||||||||||  ||||||||||
M  QDKDNWNGQL  KLLLEWNQLD  LASDEIFTND  RRWESADLQE  VMFTALIKDR  PKFVRLFLEN
   ||||||||||  ||||||||||  ||||||||.|  ||||||||||  ||||||||||  ||||||||||
R  QDKDNWNGQL  KLLLEWNQLD  LASDEIFTHD  RRWESADLQE  VMFTALIKDR  PKFVRLFLEN

C  GLNLRKFLTN  DVLTELFSNH  FSTLVYRNLQ  IAKNSYNDAL  LTFVWKLVAN  FRRGFRKEDR  540
   |||||||||.  ||||||||||  ||||||||||  ||||||||||  ||||||||||  ||||||||||
H  GLNLRKFLTH  DVLTELFSNH  FSTLVYRNLQ  IAKNSYNDAL  LTFVWKLVAN  FRRGFRKEDR
   ||||.||||.  .|||||||.|  ||||||||||  ||||||||||  ||||||||||  |||.|.||||
M  GLNLQKFLTN  EVLTELFSTH  FSTLVYRNLQ  IAKNSYNDAL  LTFVWKLVAN  FRRSFWKEDR
   ||||.||||.  .|||||||.|  ||||||||||  ||||||||||  ||||||||||  |||.|.||||
R  GLNLQKFLTN  EVLTELFSTH  FSTLVYRNLQ  IAKNSYNDAL  LTFVWKLVAN  FRRSFWKEDR

C  SSRDDIDVEL  HDVSPITRHP  LQAHFIWAIL  QNKKELSKVI  WEQTRGCTLA  ALGASKLLKT  600
   ..||..|.||  ||||||||||  |||.||||||  ||||||||||  ||||||||||  ||||||||||
H  NGRDEMDIEL  HDVSPITRHP  LQALFIWAIL  QNKKELSKVI  WEQTRGCTLA  ALGASKLLKT
   |||.|.||||  ||.|..||||  |||.||||||  ||||||||||  ||||.|||||  ||||||||||
M  SSREDLDVEL  HDASLTTRHP  LQALFIWAIL  QNKKELSKVI  WEQTKGCTLA  ALGASKLLKT
   |||.|.||||  ||.|..||||  |||.||||||  ||||||||||  ||||.|||||  ||||||||||
R  SSREDLDVEL  HDASLTTRHP  LQALFIWAIL  QNKKELSKVI  WEQTKGCTLA  ALGASKLLKT

C  LAKVKNDINA  AGESEELANE  YETRAVELFT  ECYSSDEDLA  EQLLVYSCEA  WGGSNCLELA  660
   ||||||||||  ||||||||||  ||||||||||  ||||||||||  ||||||||||  ||||||||||
H  LAKVKNDINA  AGESEELANE  YETRAVELFT  ECYSSDEDLA  EQLLVYSCEA  WGGSNCLELA
   ||||||||||  ||||||||||  ||||||||||  ||||.|||||  ||||||||||  ||||||||||
M  LAKVKNDINA  AGESEELANE  YETRAVELFT  ECYSNDEDLA  EQLLVYSCEA  WGGSNCLELA
   ||||||||||  ||||||||||  ||||||||||  ||||||||||  ||||||||||  ||||||||||
R  LAKVKNDINA  AGESEELANE  YETRAVELFT  ECYSSDEDLA  EQLLVYSCEA  WGGSNCLELA

C  VEATDQHFIA  QPGVQNFLSK  QWYGEISRDT  KNWKIILCLF  IIPLVGCGFV  SFRKRPIDKH  720
   ||||||||||  ||||||||||  ||||||||||  ||||||||||  |||||||||.  ||||.|.|||
H  VEATDQHFIA  QPGVQNFLSK  QWYGEISRDT  KNWKIILCLF  IIPLVGCGFV  SFRKKPVDKH
   ||||||||||  ||||||||||  ||||||||||  ||||||||||  |||||||||.  ||||.||||
M  VEATDQHFIA  QPGVQNFLSK  QWYGEISRDT  KNWKIILCLF  IIPLVGCGLV  SFRKKPIDKH
   ||||||||||  ||||||||||  ||||||||||  ||||||||||  |||||||||.  ||||.||||
R  VEATDQHFIA  QPGVQNFLSK  QWYGEISRDT  KNWKIILCLF  IIPLVGCGLV  SFRKKPIDKH

C  KKILWYYVAF  FTSPFVVFAW  NVVFYIAFLL  LFAYVLLMDF  HSVPHSPELV  LYALVFVLFC  780
   ||.|||||||  ||||||||.|  ||||||||||  ||||||||||  |||||.||||  ||.|||||||
H  KKLLWYYVAF  FTSPFVVFSW  NVVFYIAFLL  LFAYVLLMDF  HSVPHPPELV  LYSLVFVLFC
   ||.|||||||  ||||||||.|  ||||||||||  ||||||||||  |||||.|||.  ||||||||||
M  KKLLWYYVAF  FTSPFVVFSW  NVVFYIAFLL  LFAYVLLMDF  HSVPHTPELI  LYALVFVLFC
   ||.|||||||  ||||||||.|  ||||||||||  ||||||||||  |||||.|||.  ||||||||||
R  KKLLWYYVAF  FTSPFVVFSW  NVVFYIAFLL  LFAYVLLMDF  HSVPHTPELI  LYALVFVLFC

C  DEVRQWYMNG  VNYFTDLWNV  MDTLGLFYFI  AGIVFRLHPS  NKTSLYSGRV  IFCLDYIIFT  840
   ||||||.|||  ||||||||||  ||||||||||  ||||||||.|  ||.|||||||  ||||||||||
H  DEVRQWYVNG  VNYFTDLWNV  MDTLGLFYFI  AGIVFRLHSS  NKSSLYSGRV  IFCLDYIIFT
   ||||||||||  ||||||||||  ||||||||||  ||||||||.|  ||.|||||||  ||||||||||
M  DEVRQWYMNG  VNYFTDLWNV  MDTLGLFYFI  AGIVFRLHSS  NKSSLYSGRV  IFCLDYIIFT
   ||||||||||  ||||||||||  ||||||||||  ||||||||.|  ||.|||||||  ||||||||||
R  DEVRQWYMNG  VNYFTDLWNV  MDTLGLFYFI  AGIVFRLHSS  NKSSLYSGRV  IFCLDYIIFT

C  LRLIHIFTVS  RNLGPKIIML  QRMLIDVFFF  LFLFAVWMVA  FGVARQGILR  QNEHRWRWIF  900
   ||||||||||  ||||||||||  ||||||||||  ||||||||||  ||||||||||  |||.||||||
H  LRLIHIFTVS  RNLGPKIIML  QRMLIDVFFF  LFLFAVWMVA  FGVARQGILR  QNEQRWRWIF
   ||||||||||  ||||||||||  ||||||||||  ||||||||||  ||||||||||  |||.||||||
M  LRLIHIFTVS  RNLGPKIIML  QRMLIDVFFF  LFLFAVWMVA  FGVARQGILR  QNEQRWRWIF
   ||||||||||  ||||||||||  ||||||||||  ||||||||||  ||||||||||  |||.||||||
R  LRLIHIFTVS  RNLGPKIIML  QRMLIDVFFF  LFLFAVWMVA  FGVARQGILR  QNEQRWRWIF

C  RSVIYEPYLA  MFGQVPSDVD  GTTYDFAHCT  FTGNESKPLC  VELDEHNLPR  FPEWITIPLV  960
   ||||||||||  ||||||||||  ||||||||||  ||||||||||  ||||||||||  ||||||||||
H  RSVIYEPYLA  MFGQVPSDVD  GTTYDFAHCT  FTGNESKPLC  VELDEHNLPR  FPEWITIPLV
   ||||||||||  ||||||||||  .||||.||||  |.|||||||||  |||||.||||  ||||||||||
M  RSVIYEPYLA  MFGQVPSDVD  STTYDFSHCT  FSGNESKPLC  VELDEHNLPR  FPEWITIPLV
   ||||||||||  ||||||||||  .||||.||||  |.|||||||||  |||||.||||  ||||||||||
R  RSVIYEPYLA  MFGQVPSDVD  STTYDFSHCT  FSGNESKPLC  VELDEYNLPR  FPEWITIPLV
```

TABLE 2-continued

```
C CIYMLSTNIL LVNLLVAMFG YTVGTVQENN DQVWKFQRYF LVQEYCNRLN IPFPFVVFAY 1020
  |||||||||| |||||||||| |||||||||| |||||||||| ||||||.||| |||||.||||
H CIYMLSTNIL LVNLLVAMFG YTVGTVQENN DQVWKFQRYF LVQEYCSRLN IPFPFIVFAY
  |||||||||| |||||||||| ||||.||||| |||||||||| |||||||||| ||||||||||
M CIYMLSTNIL LVNLLVAMFG YTVGIVQENN DQVWKFQRYF LVQEYCNRLN IPFPFVVFAY
  |||||||||| |||||||||| ||||.||||| |||||||||| |||||||||| ||||||||||
R CIYMLSTNIL LVNLLVAMFG YTVGIVQENN DQVWKFQRYF LVQEYCNRLN IPFPFVVFAY

C FYMVVKKCFG CCCREKHAEP SACCFRNEDN ETLAWEGVMK ENYLVKINTE ANDTSQEMRH 1080
  |||||||||. |||.||..|. |.|||.|||| |||||||||| ||||||||.| ||||.|||||
H FYMVVKKCFK CCCKEKNMES SVCCFKNEDN ETLAWEGVMK ENYLVKINTK ANDTSEEMRH
  |||||||||. |||.||..|. .||||||||| |||||||||| |||||||||| |||.|.||||
M FYMVVKKCFK CCCKEKNMES NACCFRNEDN ETLAWEGVMK ENYLVKINTK ANDNSEEMRH
  |||||||||. |||.||..|. |||||||||| |||||||||| |||||||||| |||...||||
R FYMVVKKCFK CCCKEKNTES SACCFRNEDN ETLAWEGVMK ENYLVKINTK ANDNAEEMRH

C RFRQLDTKIN DLKGLLKEIA NKIK  (SEQ ID NO: 2)  1104
  ||||||||.| |||||||||| ||||
H RFRQLDTKLN DLKGLLKEIA NKIK  (SEQ ID NO: 11)
  ||||||.|.| |||.|||||| |.||
M RFRQLDSKLN DLKSLLKEIA NNIK  (SEQ ID NO: 12)
  ||||||||.| |||||||||| |.||
R RFRQLDTKLN DLKGLLKEIA NKIK  (SEQ ID NO: 13)
```

TABLE 3

| Position | cCMR1 residue | Variant | Position | cCMR1 residue | Variant |
|---|---|---|---|---|---|
| 4 | E | R | 353 | V | Hydrophobic (e.g., A, M) |
| 5 | G | A | 374 | T | I |
| 12 | N | S | 387 | S | C |
| 16 | G | D | 388 | S | P |
| 18 | L | Hydrophobic (e.g., M) | 403 | I | Hydrophobic (e.g., V) |
| 19 | D | G | 406 | N | S |
| 28 | T | A, V | 419 | N | S |
| 34 | V | Hydrophobic (e.g., L) | 443 | N | S |
| 38 | E | D | 444 | E | D |
| 58 | T | I | 449 | N | (Amine-containing, E.g. H) |
| 59 | K | Basic (e.g., R) | 454 | G | E |
| 64 | T | M | 485 | R | (Amine-containing, E.g. Q) |
| 66 | N | S | 490 | N | (Amine-containing, E.g. H) |
| 67 | V | Hydrophobic (e.g., I) | 491 | D | E |
| 78 | I | Hydrophobic (e.g., M) | 499 | N | T |
| 85 | S | Q | 534 | G | S |
| 86 | N | S | 536 | R | W |
| 118 | I | Hydrophobic (e.g., L) | 541 | S | N |
| 126 | A | S | 542 | S | G |
| 128 | T | I | 544 | D | E |
| 204 | N | S | 545 | D | E |
| 227 | L | Hydrophobic (e.g., I) | 546 | I | Hydrophobic (e.g., M, L) |
| 229 | N | S | 548 | V | Hydrophobic (e.g., I) |
| 232 | A | D | 553 | V | Hydrophobic (e.g., A) |
| 235 | Y | H | 555 | P | Hydrophobic (e.g., L) |
| 237 | S | L | 556 | I | T |
| 241 | I | L | 564 | H | L |
| 246 | K | T, M | 585 | R | (Basic, e.g., K) |
| 290 | I | S | 635 | S | N |
| 310 | R | (Basic, e.g., K) | 709 | F | L |
| 320 | I | Hydrophobic (e.g., V) | 715 | R | (Basic, e.g., K) |
| 322 | S | N | 717 | I | Hydrophobic (e.g., V) |
| 348 | V | Hydrophobic (e.g., A) | 723 | I | Hydrophobic (e.g., L) |
| 739 | A | S | | | |
| 766 | S | (Nucleophillic, e.g., T or P) | | | |
| 770 | V | Hydrophobic (e.g., I) | | | |
| 773 | A | S | | | |
| 788 | M | Hydrophobic (e.g., V) | | | |
| 819 | P | S | | | |
| 823 | T | (Nucleophillic, e.g., S) | | | |
| 894 | H | (Amine-containing, eg., Q) | | | |
| 921 | G | S | | | |
| 927 | A | S | | | |
| 932 | T | (Nucleophillic, e.g., S) | | | |
| 946 | H | Y | | | |
| 985 | T | I | | | |
| 1007 | N | S | | | |

TABLE 3-continued

| Position | cCMR1 residue | Variant | Position | cCMR1 residue | Variant |
|---|---|---|---|---|---|
| 1016 | V | Hydrophobic (e.g., I) | | | |
| 1030 | G | K | | | |
| 1034 | R | (Basic, e.g., K) | | | |
| 1037 | H | (Amine-containing, eg., N) | | | |
| 1038 | A | M, T | | | |
| 1040 | P | S | | | |
| 1041 | S | N | | | |
| 1042 | A | Hydrophobic (e.g., V) | | | |
| 1046 | R | (Basic, e.g., K) | | | |
| 1070 | E | K | | | |
| 1074 | T | N | | | |
| 1075 | S | A | | | |
| 1076 | Q | E | | | |
| 1087 | T | (Nucleophillic, e.g., S) | | | |
| 1089 | I | Hydrophobic (e.g., L) | | | |
| 1094 | G | S | | | |
| 1102 | K | (Basic, e.g., N) | | | |

TABLE 4

| SEQ ID NO | Description | Sequence |
|---|---|---|
| SEQ ID NO 3 | Upstream primer (cmr1-23) | ttcatctgggccattcttcag |
| SEQ ID NO 4 | Downstream primer (cmr1-26) | cacagtggcttggactcatt |
| SEQ ID NO 5 | Forward primer for 3' RACE-PCR (dcmr1-3) | gcccatcgacaagcacaagaagatc |
| SEQ ID NO 6 | Reverse primer for 5'-RACE-PCR (dcmr1-1) | gatcttcttgtgcttgtcgatgggc |
| SEQ ID NO 7 | Universal Primer | ccatcctaatacgactcactatagggc |
| SEQ ID NO 8 | Forward primer (dcmr1-7) | aagcttcatatgtccttcgaggggccaggctcagcatgaggaa |
| SEQ ID NO 9 | Reverse primer (dcmr1-8) | ctcgagctatttgattttattagcgatctctttcagaaggccc |

EXAMPLE 1

Cloning of CMR1 from Dog DRG Neurons

A. Isolation of poly($A^+$) RNA

As a first step in the cloning of cCMR1, poly($A^+$) RNA was isolated from 100 μg of total RNA from canine DRG [(Custom made by Analytical Biological Service Inc. DE)] using an Oligotex™ spin column (Qiagen Inc., CA). Briefly, 150 μl of RNase-free water, 250 μl of buffer OBB [20 mM Tris, pH7.5, 1M NaCl, 2 mM EDTA and 0.2% SDS] and 15 μl of a suspension of Oligotex beads were added to 100 μl of total RNA solution (1 μg/μl). The RNA/Oligotex bead mixture was then heated at 70° C. for 3 min to disrupt any secondary structure of the RNA followed by incubation at room temperature for 10 min. The poly($A^+$) RNA/Oligotex particle complex was centrifuged and washed twice with 400 μl of buffer OW2 [10 mM Tris, pH7.5, 150 nM NaCl, and 1 mM EDTA] and then transferred to a spin column for the elution step. The poly($A^+$) RNA was eluted from Oligotex bead using 200 μl of prewarmed (70° C.) Buffer OEB [5 mM Tris, pH 7.5]. Finally, canine DRG poly($A^+$) RNA was precipitated by ethanol in the presence of 20 μg of glycogen and 150 mM sodium acetate and resuspended in 10 μl of RNase free water.

B. Synthesis of Double-stranded cDNA

4 μl (1 μg) of canine DRG poly($A^+$) RNA and 1 μl of cDNA synthesis primer, a 52-mer oligo with sequence of 5'-TTCTAGAATTCAGCGGCGC(T)$_{30}$N$_{-1}$N-3', N$_{-1}$=G, A or C; and N=G, A, C or T (Clontech, CA SEQ ID NO:10) were mixed, incubated at 70° C. for 2 min and then cooled on ice for 2 min. The first strand cDNA synthesis (reverse transcription) was performed at 42° C. for 1 hour using 20 units of AMV reverse transcriptase in the presence of 1 mM dNTP mixture and first strand synthesis buffer (50 mM Tris, pH 8.5, 8 mM MgCl$_2$, 30 mM KCl and 1 mM DTT) in 10 μl. The second strand cDNA synthesis was performed by adding an enzyme cocktail consisting of 24 units of E. coli DNA polymerase I, 5 units of E. coli DNA ligase I unit of E. coli RNase H, 0.25 mM of dNTP mixture (0.25 mM of each dATP, dCTP, dGTP, and dTTP), and second strand buffer (100 mM KCl, 10 mM ammonium sulfate, 5 mM MgCl$_2$, 0.15 mM β-NAD, 20 mM Tris pH 7.5, and 50 μM/ml bovine serum albumin) in 80 μl. The reaction was first carried out at 16° C. for 90 min followed by addition of 20 units of T4 DNA polymerase with continued incubation at the same temperature for 45 min. The reaction was terminated by adding 10 mM EDTA and 8 μg of glycogen. Phenol and chloroform extractions were performed, followed by ethanol precipitation. Double-stranded cDNA was then suspended in 200 μl of TE buffer and stored at −20° C.

C. PCR Amplification of Near Carboxyl Terminus of Dog CMR1

A portion of the cCMR1 sequence was successfully amplified by PCR using two primers designated cmr1-23 (5'-ttcatctgggccattcttcag-3' (SEQ ID NO: 3), which hybridizes to nucleotides 1761-1781 of SEQ ID NO 1 and cmr1-26 (5'-cacagtggcttggactcatt-3' (SEQ ID NO: 4), which hybridizes to nucleotides 2868-2886 of SEQ ID NO: 1. The PCR reaction was performed in final volume of 50 μl, containing 5 μl of canine DRG double-stranded cDNA, 5 μl of 10× reaction buffer provided with Advantage2 DNA polymerase, 200 μM dNTPs, 200 nM forward primer cmr1-23, 200 nM reverse primer cmr1-26 and 1 μl of 50× Advantage™-HF2 DNA polymerase mixture (Clontech, CA). PCR was performed by an initial denaturing step at 94° C. for 1 min, followed by 30 cycles of: (a) denaturing at 94° C. for 30 sec, (b) annealing at 55° C. for 30 sec and (c) extension at 72° C. for 60 sec.

Agarose gel electrophoresis was performed, which revealed that the PCR product was approximately 1.1 kb. After PCR, the 1.1 kb PCR fragment was purified and subcloned into pPCRscript (Stratagene) following the vendor's protocol. Two independent clones were picked and subjected to DNA sequencing analysis.

The sequence results revealed that the PCR amplified fragment was 83% 84%, and 87% identical to the near the carboxyl termini of mouse, rat and human CMR1, respectively.

D. RACE-PCR of 5' and 3' Ends of cCMR1 Sequence

To obtain the complete 5' and 3' cDNA sequences of the cCMR1 gene, RACE-PCR technology was performed. First, both 5'- and 3'-RACE-Ready cDNAs were synthesized separately with SMART™ RACE DNA Amplification Kit (BD Clontech, CA), according to the manufacturer's instructions. To prepare cDNA for 5' RACE, in one 0.5 ml tube, 3 μl of dog DRG poly(A$^+$) RNA obtained in A. was mixed with 1 μl of 5'-CDS primer and 1 ml of SMART II A oligo. To prepare cDNA for 3' RACE, 3 μl of dog DRG poly(A$^+$) RNA was mixed with 1 μl 3'-CDS primer and 1 μl RNase free water in another 0.5 ml tube and then incubated at 70° C. for 2 min followed by cooling on ice for 2 min. Next, 2 μl of 5× First Strand buffer, 1 μl 20 mM DTT, 1 μl of 10 mM dNTP mix and 1 μl PowerScript Reverse Transcriptase were added to each tube, and synthesis was performed at 42° C. for 90 min. The reactions were stopped by adding 200 μl of TE buffer and heating the sample to 72° C. for 7 min. The reaction products were stored at −20° C.

For RACE-PCR, two primers were synthesized based on the 1.1 kb cDNA sequence proximal to the 5' portion of the cCMR1 cDNA. The forward primer for 3' RACE-PCR was named dcmr1-3 and had the following sequence: 5'-GCCCATCGACAAG CACAAGAAGATC-3' (SEQ ID NO: 5), which hybridizes to nucleotides 2213-2237 of SEQ ID NO: 1 (complementary strand); the reverse primer for 5'-RACE-PCR was named dcmr1-1 and had the following sequence: 5'-GATCTTCTTGTGCTTGTCGATGGGC-3' (SEQ ID NO: 6), which hybridizes to nucleotides 2213-2237 of SEQ ID NO: 1. Both 5' and 3'-RACE PCRs were performed in a final volume of 50 μl containing 5 μl of cDNA template (either 5'- or 3'-RACE-Ready cDNA, as described above), 5 μl of 10× reaction buffer, 200 μM dNTPs, 200 nM Universal Primer Mix (UPM) (Clontech), SEQ ID NO: 7 (5'-CCATCC TAA TAC GAC TCA CTA TAG GGC-3'), 200 nM cCMR1 specific primer (dcmr1-1 for 5'-RACE PCR or dcmr1-3 for 3'-RACE PCR) and 1 μl of 50× Advantage™-HF2 DNA polymerase mixture (Clontech). The thermal cycler parameters for the RACE-PCR were: a) initial denaturing at 94° C. for 2 min; b) 5 cycles of: 94° C. for 30 sec, 72° C. for 3 min; c) 5 cycles of: 94° C. for 30 sec, 70° C. for 30 sec, 72° C. for 3 min; and d) 25 cycles of 94° C. for 5 sec, 68° C. for 30 sec, 72° C. for 3 min. After the reaction, the RACE-PCR products were purified, polished and directly subcloned into pPCRscript. Four independent clones from either 5'-RACE or 3'-RACE were picked and subjected to DNA sequencing analysis.

E. Sequence of Full-length cCMR1 cDNA:

The sequence of the full-length canine CMR1 cDNA was confirmed by synthesizing PCR primers based on the sequence of the 5' and 3' ends obtained by RACE-PCR. Full length cCMR1 cDNA was amplified from canine DRG double-stranded cDNAs prepared in B. by high-fidelity DNA polymerase with forward primer dcmr1-7, which had the following sequence: 5'-AAGCTTCAT ATG TCC TTC GAG GGG GCC AGG CTC AGC ATG AGG AA-3' (SEQ ID NO: 8) and reverse primer dcmr1-8, which had the following sequence: 5'-CTCGAG CTA TTT GAT TTT ATT AGC GAT CTC TTT CAG AAG GCCC-3' (SEQ ID NO: 9). The PCR was performed in a final volume of 50 μl containing 5 μl of above dog DRG double-stranded cDNAs, 5 μl of 10× reaction buffer, 200 μM dNTP, 200 nM forward primer dcmr1-7, 200 nM reverse primer dcmr1-8, and 1 μl of 50× Advantage™-HF2 DNA polymerase mixture (Clontech, CA). The PCR reaction parameters were: 1 cycle: initial denaturing at 94° C. for 2 min; 35 cycles: a) denaturing at 94° C. for 30 sec, b) annealing and extension at 70° C. for 5 min. After PCR, the 3.4 kb PCR fragment was purified and subcloned into pPCRscript following the same cloning protocol as in C. Four independent clones were picked and subjected to DNA sequencing analysis. The clone NQC562 was used for further subcloning and studying. The sequence results revealed that the nucleic acid sequence of cCMR1 cDNA (nucleotides 69-3380 of SEQ ID NO: 1) was 86.2%, 86.6%, and 90.9% identical to the cDNA sequences of mouse (Accession number: AY095352), rat (Accession number: AY072788) and human (Accession number: NM_024080) CMR1, respectively.

F. Sequence Analysis

5'- and 3'-RACE-PCR allowed for the determination of the 68 nucleotide sequence of the 5' untranslated region; 3'-RACE-PCR allowed for the determination of the 431 bp of the 3' untranslated region including the 37-mer poly(A$^+$) tail. No in-frame stop codon was identified.

The predicted cCMR1 open reading frame consists of a 3315 bp sequence that is predicted to encode a polypeptide of 1104 amino acids (SEQ ID NO: 2) having a calculated molecular mass of 127.6 kDa (see Table 1). A Kyte-Doolitle hydrophilicity analysis (not shown) of primary sequence predicts the presence of eight putative hydrophobic domains clustered near the carboxyl terminus. A high probability of coiled-coil domain located at the very carboxyl terminal from residue 1070 to the end, which may be implicated in oligomerization of the channel, was identified. Further, the primary sequence analysis with GCG SeqWeb revealed that cCMR1 contained multiple N-glycosylation sites located at residues 15, 256, 317, 812, 934, 1050 and 1072, respectively. cCMR1 also contains one putative PKA (protein kinase A) phosphorylation sites at residue 92, three tyrosine phosporylation sites at residues 30, 228 and 288, and 17 PKC (protein kinase C) phosphorylation sites.

The cCMR1 amino acid sequence was aligned with the human (GenBank Acc. No.: NP_076985), rat (GenBank Acc. No.: NP_599198), and mouse (GenBank Acc. No.: AAM23261) sequences which revealed a 95.1%, 94.1%, and 93.9% identity, respectively, using the Gap program from Seqweb version 2 of Accelrys. The Gap program uses the algorithm of Needleman and Wunsch (J. Mol. Biol., 48:443 (1970)) to find the alignment of two complete sequences. It maximizes the number matches and minimizes the number of gaps.

EXAMPLE 2

Recombinant Expression of CMR1

A. Cloning of cCMR1 into a Mammalian Expression Vector

For expression of cCMR 1 in mammalian cell lines, the full-length cDNA of cCMR1 was subcloned into pcDNA3.1 by performing a three-way ligation. First, the full-length cCMR1 clone NQC562 was digested with HindIII and NcoI to yield a 0.8 kb 5' fragment. Next, in an independent restriction reaction, NQC562 was digested with NcoI and SalI to yield a 2.5 kb 3' fragment. The 0.8 kb 5' and 2.5 kb 3' cCMR1 fragments were purified and ligated with pcDNA3.1 that was predigested with HindIII and SalI, creating vector pcDNA3.1-cCMR1.

For in vitro translational analysis, full-length cCMR1 cDNA was subcloned into pAGA4 vectors (modified from pGEM3 of Promega, Sanford 1991 and Qin, et al 1997). Briefly, 0.8 kb N-terminal fragment was obtained by digestion of NQC562 with NdeI and NcoI and a 2.5 kb C-terminal fragment was obtained by digestion of NQC562 with NcoI and XhoI. The two purified fragments were ligated together with vector pAGA4 predigested with NdeI and SalI, creating construct cCMR1/pAGA4. All the final constructs were confirmed by DNA sequencing.

B. In Vitro Translation of cCMR1

In vitro translation of the canine CMR1 was done with TnT™ T7 Quick Coupled Transcription/Translation System (Promega), according to the vendor-recommended protocol. Briefly, 1 μl of 0.1 μg/μl cCMR1/pAGA4 was added to 9 μl of TNT Quick Master Mix with 0.2 μl of [$^{35}$S]-methionine (1000 Ci/mmol at 10 mCi/ml). The reaction mixture was incubated at 30° C. for 90 min. The reaction was stopped by adding an equal volume of 2×SDS/PAGE loading buffer, and then, the samples were subjected to 4-20% gradient SDS-PAGE analysis. After electrophoresis, the gel was stained with Commassie Blue R250, dried and exposed to X-ray film. The in vitro translated cCMR1 migrated to an approximate molecular weight of 135 kDa as predicted by faithful translation of the amino acid sequences from the corresponding nucleic acid sequences.

The in vitro translated cCMR1 protein was also analyzed by Western blot. 5 μl of in vitro translated cCMR1 protein was subjected to 4-20% gradient SDS-PAGE. The proteins on the gel were then transferred to nitrocellulose. The blot was then blocked with 5% dry milk in TTBS (0.5% Tween 20, 100 mM Tris-HCl, and 0.9% NaCl at pH=7.5) at room temperature for 1 hour and then incubated with anti-cCMR1 polyclonal antibody (1:500) at 4° C. overnight. The next day, the blot was washed three times with 100 ml TTBS, and incubated with goat anti-rabbit IgG antibody conjugated with horseradish peroxidase (Pierce) at room temperature for 1 hour. The blot was washed three times with 100 ml TTBS and visualized with ECL-Plus luminescent reagents (Amersham-Pharamacial Biotech) according to the manufacturer's instructions.

The pcDNA3.1-cCMR1 construct was transfected into HEK293 (human embryonic kidney cells (ATCC CRL-1573) using the GeneJammer™ kit (Stratagene, CA), according to manufacturer's protocol. Stable cell clones were selected by growth in the presence of G418. Single G418 resistant clones were isolated and purified. Clones containing the cCMR1 cDNA were analyzed using a calcium influx assay.

EXAMPLE 3

Calcium Influx Functional Assay of cCMR1

FLIPR assay was performed to study the properties of cCMR1 channels within a population of cells.

To demonstrate functionality of the cCMR1 expressed in recombinant cells, CMR1/HEK293 stably transfected cells were seeded in a 384-well plate at a concentration of $6.7 \times 10^5$ cells/well and incubated overnight at 37° C. The following day, the cells were loaded with buffer and calcium dye (Molecular Devices, Sunnyvale, Calif.) in a final volume of 40 μl and incubated for 30 minutes at room temperature. The fluorescence intensity was measured by FLIPR before and after the addition of menthol or icilin, which were added to the cells at a concentration of 100 μM or 10 μM each, respectively. The results are shown in FIG. 1.

EXAMPLE 4

CMR1 Functional Assay with Reduced $Ca^{++}$ Loading Concentrations

CMR1 opens in response to agonists, such as menthol or icilin, and also to mildly cold temperatures (15° C. to 25° C.). Therefore, at room temperature (22-24° C.) CMR1 could be active and induce $Ca^{2+}$ influx. However, $Ca^{2+}$ influx will also induce $Ca^{2+}$-dependent inactivation, resulting in negative feedback regulation of CMR1. In this case, CMR1 will be inactivated after activation by room temperature and will not be reactivated until the temperature is increased above about 25° C. Therefore, under normal test conditions (room temperature and in the presence of buffer containing 2 mM Ca 2), CMR1 from certain species, such as rat CMR1, is not responsive to any agonist. To prepare a system wherein CMR1 would be used to screen antagonist at room temperature, a $Ca^{2+}$ influx assay was developed by removing $Ca^{2+}$ from the dye loading buffer and then challenging the CMR1-continaing system with 4 mM $Ca^{2+}$. Under this condition, although CMR1 is active (at room temperature), no calcium will enter the cell through the channel and inactivation will not occur. Under these assay conditions CMR1 is constitutively active and primed to permit $Ca^{2+}$ influx as soon as $Ca^{2+}$ is added into the extracellular solution.

Figure 2:
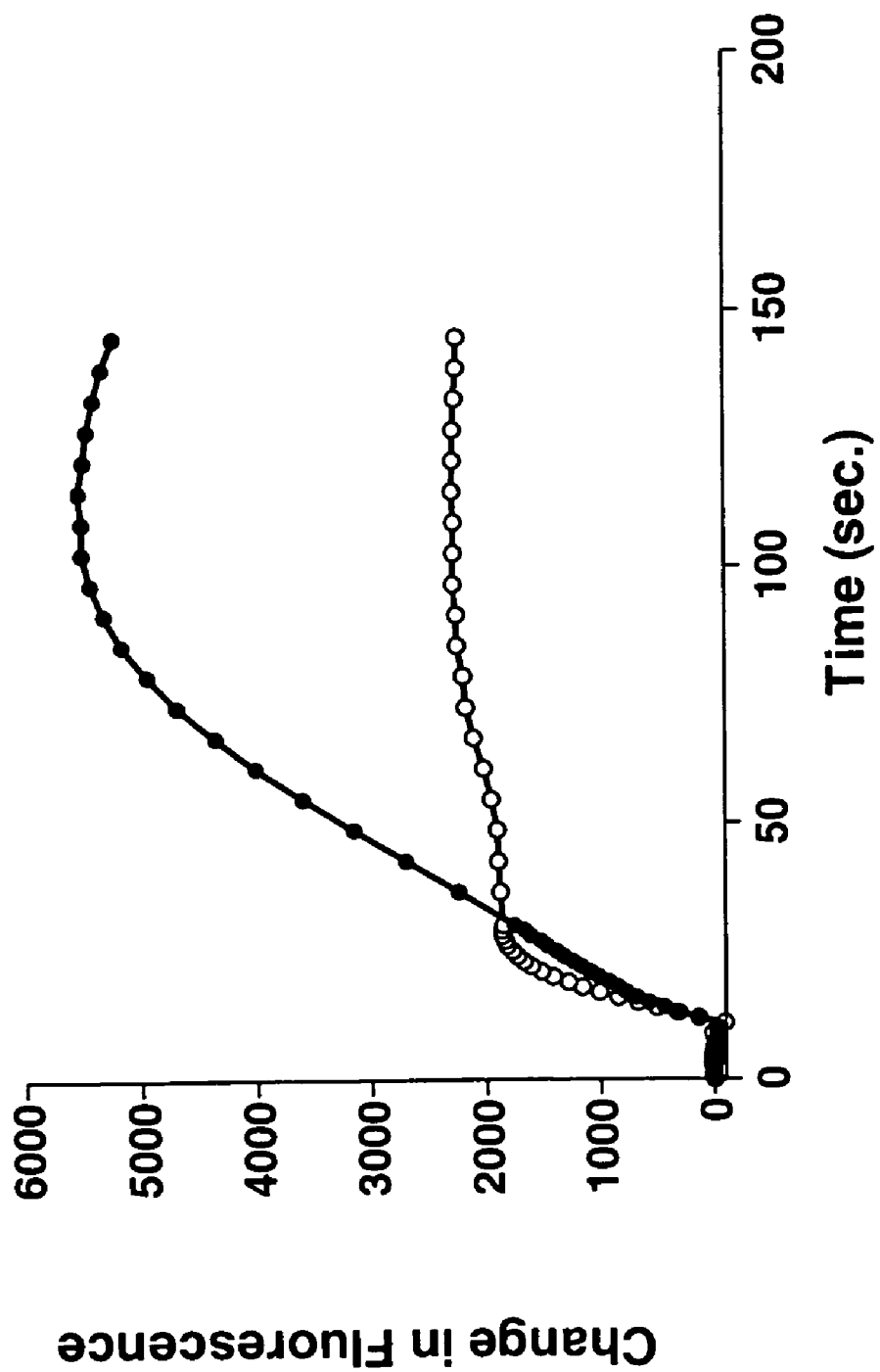
FIG. 2 illustrates results of a cell-based calcium influx assay using a loading buffer that is substantially free of calcium. Recombinant cells stably transfected with a rat CMR1 expression vector (filled circle) showed an increase in calcium-mediated fluorescence upon the addition of 4 mM $Ca^{2+}$. The non-transformed cell (open circle) had less $Ca^{2+}$ influx upon the addition of 4 mM $Ca^{2+}$. The $Ca^{2+}$ was added to the cells at time point 10 seconds.

Human Embryonic Kidney cells (HEK293) transfected with rat CMR1 were seeded in a 384-well plate ($6.7 \times 10^5$ cells/well). The following day, the culture media was removed and the cells were rinsed with complete Hank's buffer. Cells were then loaded with buffers and calcium dye (Mol. Dev.) in a final volume of 40 μl and incubated for 30 minutes at room temperature. The plates were then transferred to a FLIPR apparatus wherein compounds tested for antagonist activity were added to a final concentration of 4.2 μM at time zero. Calcium was added to a final concentration of 4 mM at about time 10 second, and fluorescence intensity was measure by FLIPR. A representative result is shown in FIG. 2 wherein no test compound was added at time zero.

EXAMPLE 5

A Screening Assay for a Desensitizer or Inactivator of a CMR1 Channel

Generally, upon prolonged exposure of an ion channel to an activating stimulus (e.g., an agonist) or in response to a direct desensitizing or inactivating stimulus, the channel may assume alternate conformations that are variably less activatable in response to an activating stimulus. These less activatable or inactivatable conformations may be referred to functionally as being desensitized or inactivated, and compounds that produce these states as being desensitizers or inactivators, respectively. Such conformations may be induced or stabilized by or in the presence of these so-called desensitizers or inactivators, and may arise by the preferential action of the desensitizer or inactivator upon an open or upon a closed channel. In addition, such conformations may be reversible, across variable time courses and conditions, or may be irreversible, pending de novo synthesis of nascent channels. Compounds that are identified as desensitizers or inactivators, either being reversible or irreversible, may be useful in the treatment of certain conditions, including pain conditions, in which decreased CMR1 activity would be therapeutic.

Therefore, in another embodiment, the invention provides a method of identifying reversible and irreversible desensitizers or inactivators of CMR1 activity. The first method is designed to identify compounds that induce and/or stabilize the channel in a desensitized or inactivated state from a closed state and comprises the steps of: (a) providing a recombinant cell comprising a nucleic acid encoding a cCMR1 protein, (b) contacting the recombinant cell at a temperature above the threshold for activation (typically above about 28° C.) with a test compound for varying lengths of time, (c) extensively washing out the test compound and (d) at varying time points, determining the extent to which the test compound diminishes CMR1 activity in response to a subsequent exposure to a CMR1-activating stimulus. The second method is designed to identify compounds that induce and/or stabilize the channel in a desensitized or inactivated state from an open state and comprises EITHER the steps of: (a) providing a recombinant cell comprising a nucleic acid encoding a cCMR1 protein, (b) contacting the recombinant cell at a temperature above the threshold for activation (typically above about 28° C.) with a CMR1 agonist, (c) contacting the recombinant cell with a test compound for varying lengths of time, (d) extensively washing out the test compound and agonist and (e) at varying time points, determining the extent to which the test compound diminishes CMR1 activity in response to a subsequent exposure to a CMR1-activating stimulus OR the steps of: (a) providing a recombinant cell comprising a nucleic acid encoding a cCMR1 protein, (b) incubating the recombinant cell at a temperature below the threshold for activation (typically below about 28° C.), (c) contacting the recombinant cell with a test compound for varying lengths of time, (d) extensively washing out the test compound and (e) at varying time points, determining the extent to which the test compound diminishes CMR1 activity in response to a subsequent exposure to a CMR1-activating stimulus.

EXAMPLE 6

Activation of cCMR1 by Mustard Oil

Mustard oil is a nature product that elicits pain and inflammation when applied to the skin. Recently, TRPA1, a novel member of TRP family, has been proposed as one of the cellular and molecular targets for the pungent action of mustard oils (Jordt, et al. 2004, Nature, 427: 260-265). We demonstrated that Mustard oil also activates cCMR1.

Figure 3:
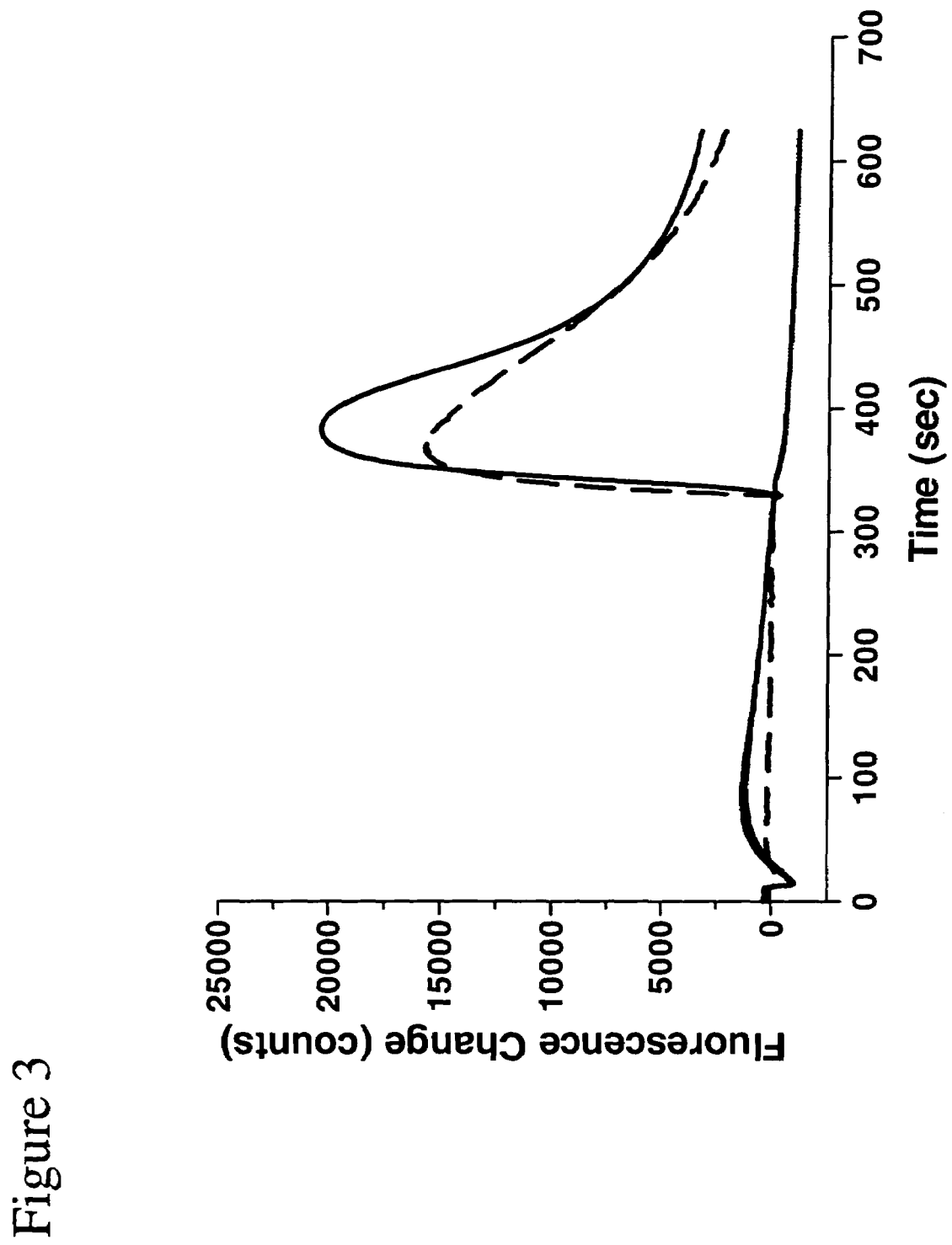
FIG. 3 illustrates that cCMR1 is activated by mustard oil, a pungent compound. Recombinant cells stably transfected with cCMR1 showed an increase in calcium-mediated fluorescence upon the addition of 1 mM mustard oil (dash line) or 100 nM icilin as the positive control (solid line). Buffer alone was used as the negative control (dot line).

HEK293 cells stably transfected with cCMR1 were seeded in a 384 will plate at a concentration of $6.7 \times 10^5$ cells/well and incubated overnight at 37° C./5% $CO_2$. The following day the cells were loaded with calcium dye and incubated for 30 minutes at room temperature. The calcium-mediated fluorescence intensity was measured by FLIPR before and after the compound was administered to the cells. As shown in FIG. 3, cCMR1 is not only sensitive to cooling compounds such as 100 nM icilin (solid line), but also is activated by the pungent compound, 1 mM mustard oil (dash line).

EXAMPLE 7

Whole-cell Patch Clamp Studies

Patch clamp experiments were performed to study the properties of cCMR1 channels expressed in a single cell.

HEK293 cells stably transfected with canine cCMR1 were cultured in DMEM supplemented with 10% fetal bovine serum, 100 units/ml penicillin, 100 μg/ml streptomycin and 1 mg/ml G418. Cells were maintained at 37° C. and in 5% $CO_2$.

Unless otherwise indicated, the standard extracellular solution used for recording contained (in mM): NaCl, 132; EGTA, 1; KCl, 5.4; $MgCl_2$, 0.8; HEPES, 10; glucose, 10; pH=7.4. In experiments where the extracellular solution contained $Ca^{2+}$, the extracellular solution used was one of the following (in mM), depending on the $Ca^{2+}$ concentration used: (1) NaCl, 132; $CaCl_2$, 0.1 or 1.8; KCl, 5.4; $MgCl_2$, 0.8; HEPES, 10; glucose, 10; pH=7.4; (2) NaCl, 116; $CaCl_2$, 10; KCl, 5.4; $MgCl_2$, 0.8; HEPES, 10; glucose, 10; pH=7.4. The intracellular solution used to fill recording pipettes contained (in mM): CsCl, 145; EGTA, 5; HEPES, 10; glucose, 5; pH=7.4.

Recordings were performed using the conventional whole-cell patch clamp technique, 1-2 days after plating cells onto glass coverslips at densities appropriate for single cell recording. Currents were amplified by a patch clamp amplifier and filtered at 2 kHz (Axopatch 200B, Axon Instruments). Menthol (100 μM) or icilin (1 μM) was applied to the cell at 0.5 ml/min via a gravity-fed perfusion system. Recordings involving agonist stimulations were performed at 22° C.

In experiments where temperatures were varied, temperature ramps were generated by heating/cooling the perfusate in a dual in-line heater/cooler (Model SC-20, Warner Instruments, Hamden, Conn.) controlled by a bipolar temperature controller (Model CL-100, Warner Instruments). The temperature in the vicinity of the recorded cell was measured with a custom-made miniature thermo-microprobe connected to a monitoring thermometer (Model TH-8, Physitemp, Clifton, N.J.), and sampled using Digidata 1322A and pClamp 9.0 (Axon Instruments, Union City, Calif.), as were the currents concurrently measured in the whole-cell patch clamp mode. Two voltage protocols were used in these studies. The first involved a 600 ms voltage ramp from −100 mV to +60 mV at a sampling rate of 10 kHz. This voltage pulse was repeated once every 5 seconds. The cell was held at −100 mV between voltage pulses. In the second protocol, the cell was held at −80 mV and the current was continuously sampled (at 100 Hz) at this holding potential.

Figure 4:
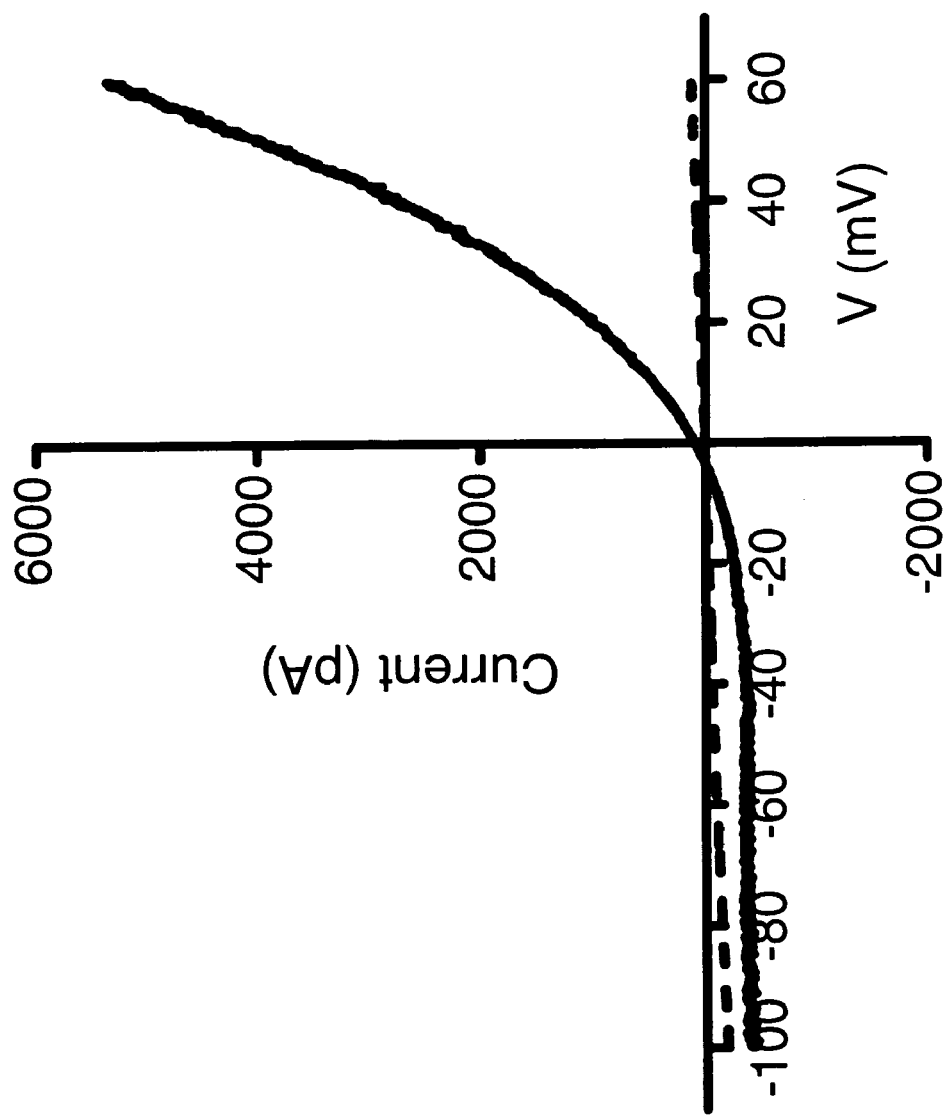
FIG. 4 illustrates that cCMR1 is strongly outwardly rectifying and non-selective to cations. The solid line represents the whole-cell patch clamp recording of cCMR1 performed in the presence of 100 µM menthol, whereas the dashed line represents the buffer control.

FIG. 4 illustrates that cCMR1 is strongly outwardly rectifying and non-selective to cations. Whole-cell patch clamp recording of cCMR1 was performed using the voltage ramp protocol described above. Upon application of 100 µM menthol, a cooling agent, there was a large increase of the whole-cell current amplitude (solid line) compared to control (dashed line) at both hyperpolarized and depolarized membrane potentials. This increase was much more pronounced at depolarized potentials than at hyperpolarized potentials. Hence, the channel is strongly outwardly rectifying. In addition, the menthol-activated current had a reversal potential near 0 mV, indicating the relatively unselective (at least to the cations used in these experiments) nature of the channel. Qualitatively similar results have also been obtained for another cooling agent, icilin.

Figure 5:
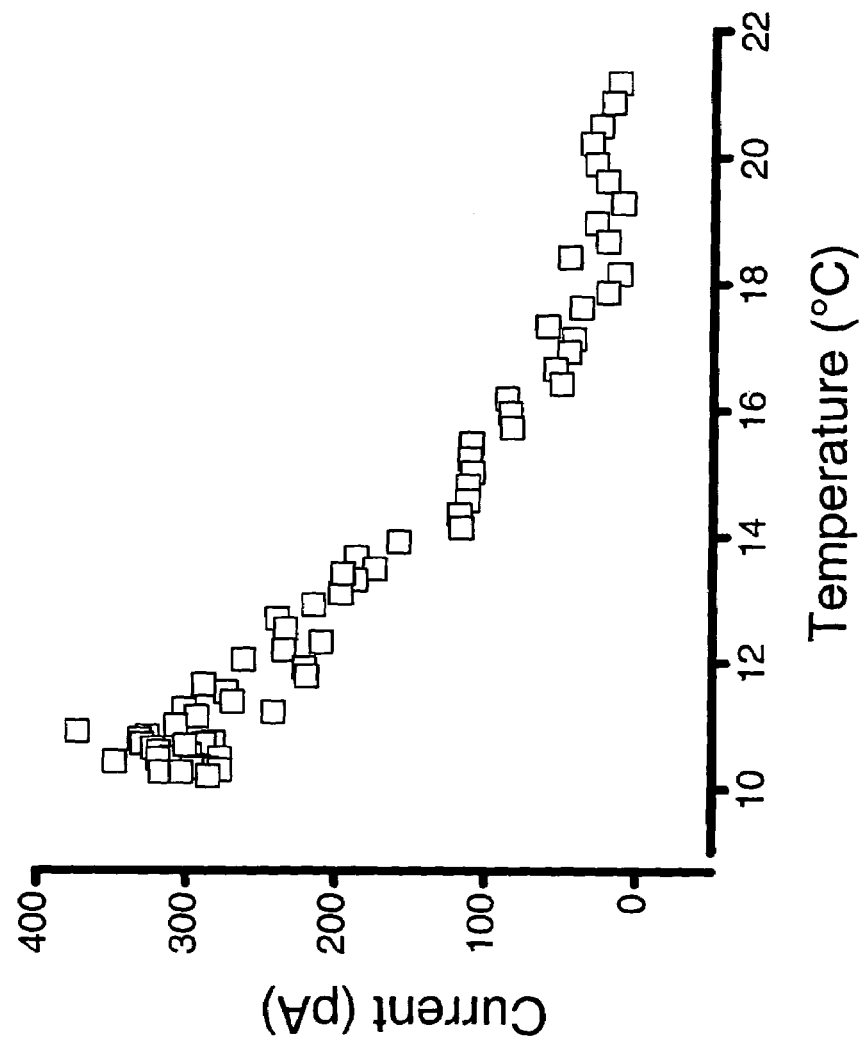
FIG. 5 illustrates the temperature sensitivity of cCMR1. The current passing through the cell was significantly increased as the temperature of the solution perfusing the cCMR1-expressing cell was lowered, demonstrating an activation threshold of about 17° C.

The temperature sensitivity of cCMR1 is illustrated in FIG. 5. As the temperature of the solution perfusing the cCMR1-expressing cell was lowered, the current passing through the cell at +60 mV was significantly increased with an activation threshold of ~17° C. The cCMR1 channel was not open at room temperature, but was activated by cool temperatures below about 17° C.

Figure 6:
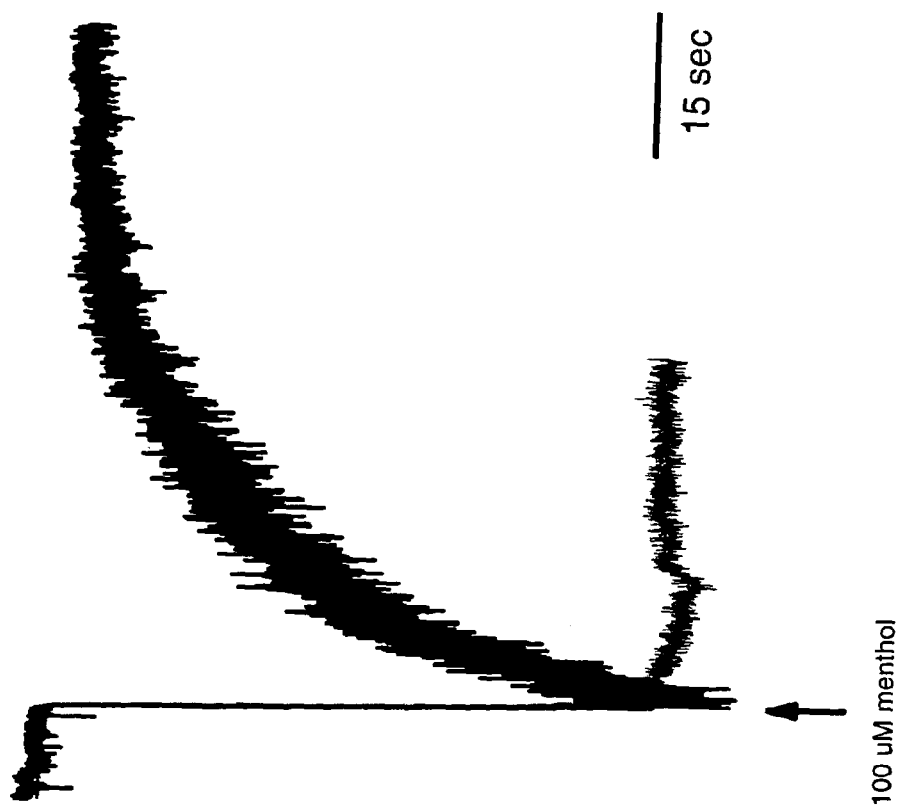
FIG. 6 illustrates that extracellular $Ca^{2+}$ desensitizes the cCMR1 channel. The lowest trace represents the whole-cell patch clamp recording of cCMR1 in the presence of 100 µM menthol and in the absence of extracellular $Ca^{2+}$, whereas the upper most, black trace, normalized to the $Ca^{2+}$-free trace for display clarity, represents current activated by 100 µM menthol in the presence of 1.8 mM extracellular $Ca^{2+}$.

FIG. 6 demonstrates that extracellular $Ca^{2+}$ desensitizes the cCMR1 channel. Menthol at 100 µM activated a non-desensitizing current in the absence of extracellular $Ca^{2+}$ (−80 mV; gray trace). In contrast, desensitization readily occurred in the presence of 1.8 mM extracellular $Ca^{2+}$ under otherwise identical recording conditions (black trace; normalized to the $Ca^{2+}$-free trace for display clarity).

Figure 7:
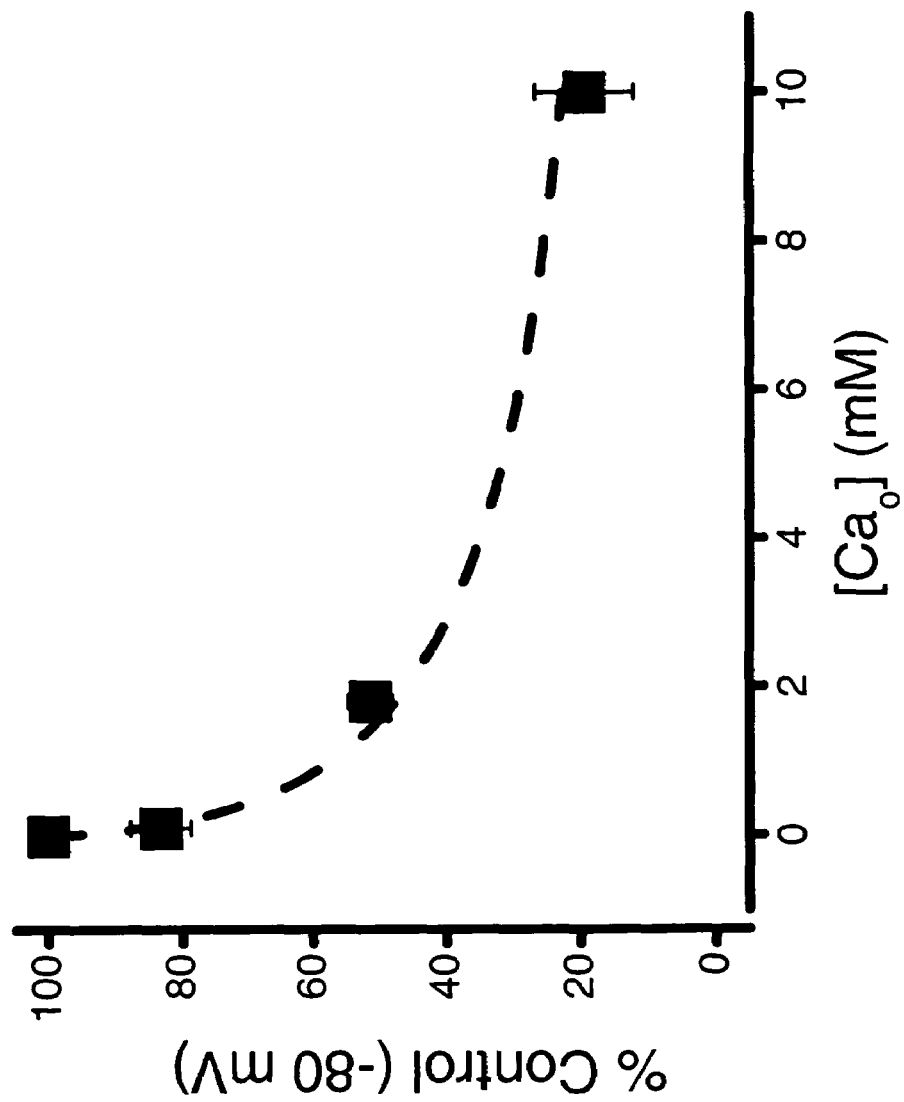
FIG. 7 illustrates the concentration dependence of the inhibition of the current amplitude of cCMR1 channel by extracellular $Ca^{2+}$. The channel was voltage-clamped at −80 mV and activated by 1 mM menthol. The dashed line is a logistic function representing the best fit to the data, with an $IC_{50}$ value of 1.6 mM.
Figure 8:
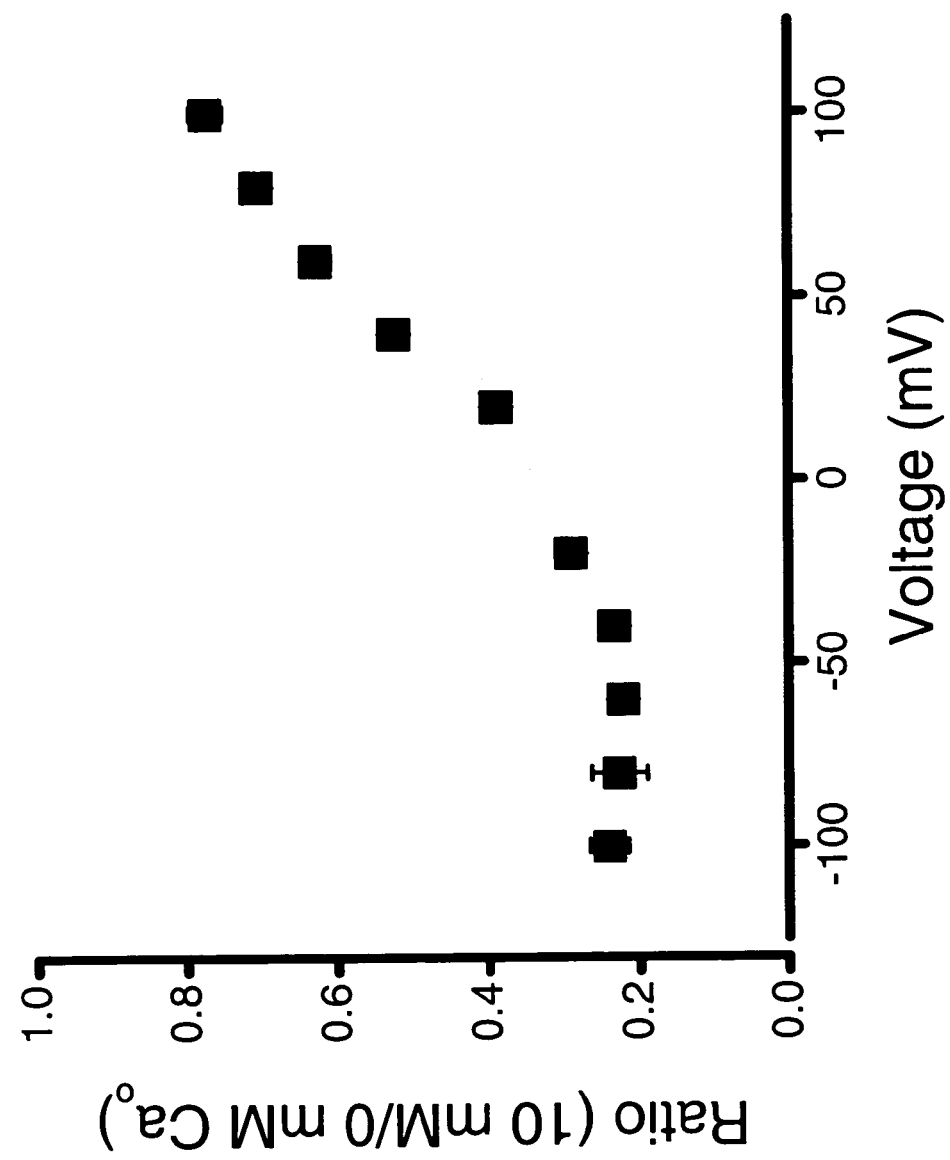
FIG. 8 illustrates the voltage dependence of the inhibition of the current amplitude of cCMR1 channel by extracellular $Ca^{2+}$. The channel was activated by 1 mM menthol.

Extracellular $Ca^{2+}$ decreased the current amplitude of cCMR1 when the channel was activated by menthol, for example at 1 mM. This apparent inhibition by extracellular $Ca^{2+}$ was concentration dependent (FIG. 7). The higher concentration of extracellular $Ca^{2+}$, the stronger the inhibition of the current amplitude. The dashed line in FIG. 7 is a logistic function representing the best fit to the data. An $IC_{50}$ value of 1.6 mM extracellular $Ca^{2+}$ was derived from the best fit analyses. In addition, the apparent inhibition by extracellular $Ca^{2+}$ was voltage-dependent (FIG. 8). Extracellular $Ca^{2+}$ (10 mM) strongly inhibited the current amplitude at hyperpolarized potentials. The inhibition was lessened at more depolarized potentials.

---

What is claimed is:

1. An isolated nucleic acid molecule comprising a nucleotide sequence that encodes a polypeptide capable of detecting and transducing cold stimuli and having at least 98% sequence identity to SEQ ID NO: 2.

2. The isolated nucleic acid molecule of claim 1 that encodes a polypeptide of SEQ ID NO: 2.

3. The isolated nucleic acid molecule of claim 1 comprising nucleotide 69 to 3380 of SEQ ID NO: 1.

4. An expression vector comprising the isolated nucleic acid sequence of claim 1.

5. A recombinant host cell comprising the isolated nucleic acid sequence of claim 1.

6. A method for expressing a polypeptide having at least 98% sequence identity to SEQ ID NO: 2 comprising the steps of:
   (a) introducing an expression vector capable of encoding a polypeptide having at least 98% sequence identity to SEQ ID NO: 2 into a cell; and
   (b) culturing the cell under conditions that allow expression of the polypeptide from the expression vector.

* * * * *